(12) United States Patent
Kishi et al.

(10) Patent No.: US 9,938,288 B1
(45) Date of Patent: Apr. 10, 2018

(54) MACROCYCLIC COMPOUND AND USES THEREOF

(71) Applicants: President and Fellows of Harvard College, Cambridge, MA (US); Eisai R&D Management Co., Ltd., Tokyo (JP)

(72) Inventors: Yoshito Kishi, Cambridge, MA (US); Kazunobu Kira, Tsukuba (JP); Ken Ito, Tsukuba (JP)

(73) Assignees: President and Fellows of Harvard College, Cambridge, MA (US); Eisai R&D Management Co., LTD., Tokyo (JP)

( * ) Notice: Subject to any disclaimer, the term of this patent is extended or adjusted under 35 U.S.C. 154(b) by 0 days.

(21) Appl. No.: 15/814,105

(22) Filed: Nov. 15, 2017

Related U.S. Application Data

(60) Provisional application No. 62/526,677, filed on Jun. 29, 2017, provisional application No. 62/482,030, filed on Apr. 5, 2017.

(51) Int. Cl.
C07D 498/22 (2006.01)
A61K 31/357 (2006.01)
C07D 493/22 (2006.01)
A61K 39/395 (2006.01)

(52) U.S. Cl.
CPC .......... *C07D 493/22* (2013.01); *A61K 31/357* (2013.01); *A61K 39/3955* (2013.01); *A61K 2300/00* (2013.01)

(58) Field of Classification Search
CPC C07D 498/22; A61K 31/357; A61K 39/3955; A61K 2300/00
See application file for complete search history.

(56) References Cited

U.S. PATENT DOCUMENTS

| | | | |
|---|---|---|---|
| 5,338,865 | A | 8/1994 | Kishi et al. |
| 5,436,238 | A | 7/1995 | Kishi et al. |
| 5,786,492 | A | 7/1998 | Gravalos et al. |
| 6,214,865 | B1 | 4/2001 | Littlefield et al. |
| 6,469,182 | B1 | 10/2002 | Littlefield et al. |
| 6,653,341 | B1 | 11/2003 | Littlefield et al. |
| 7,470,720 | B2 | 12/2008 | Littlefield et al. |
| 7,982,060 | B2 | 7/2011 | Austad et al. |
| 8,093,410 | B2 | 1/2012 | Chase et al. |
| 8,097,648 | B2 | 1/2012 | Littlefield et al. |
| 8,203,010 | B2 | 6/2012 | Endo et al. |
| 8,350,067 | B2 | 1/2013 | Endo et al. |
| 8,445,701 | B2 | 5/2013 | Austad et al. |
| 8,598,373 | B2 | 12/2013 | Hu |
| 8,618,313 | B2 | 12/2013 | Benayoud et al. |
| 8,884,031 | B2 | 11/2014 | Chase et al. |
| RE45,324 | E | 1/2015 | Austad et al. |
| 8,927,597 | B2 | 1/2015 | Endo et al. |
| 8,975,422 | B2 | 3/2015 | Fang et al. |
| 8,987,479 | B2 | 3/2015 | Chase et al. |
| 9,206,194 | B2 | 12/2015 | Hu |
| 9,278,979 | B2 | 3/2016 | Souza et al. |
| 9,303,039 | B2 | 4/2016 | Zhang et al. |
| 9,303,050 | B2 | 4/2016 | Benayoud et al. |
| 9,382,262 | B2 | 7/2016 | Endo et al. |
| 9,469,651 | B2 | 10/2016 | Hu |

(Continued)

FOREIGN PATENT DOCUMENTS

| | | |
|---|---|---|
| JP | 2003-261447 A | 9/2003 |
| WO | WO 1993/017690 A1 | 9/1993 |

(Continued)

OTHER PUBLICATIONS

US 9,029,573, 05/2015, Hu (withdrawn)
Extended European Search Report for EP 15814059.0, dated Nov. 24, 2017.
International Search Report and Written Opinion for PCT/US2015/038439, dated Sep. 29, 2015.
International Preliminary Report on Patentability for PCT/US2015/038439, dated Jan. 12, 2017.
International Search Report and Written Opinion for PCT/US2016/030064, dated Aug. 8, 2016.
International Preliminary Report on Patentability for PCT/US2016/030064, dated Nov. 9, 2017.
[No Author Listed] Application for Product Designation Under the SAKIGAKE Designation System. Generic name E7130. Eisai Co., Ltd. Nov. 22, 2017.

(Continued)

*Primary Examiner* — Timothy R Rozof
(74) *Attorney, Agent, or Firm* — Wolf, Greenfield & Sacks, P.C.

(57) ABSTRACT

The present invention provides novel Compound (1) having tumor vascular remodeling effect and/or anti-CAF (Cancer Associated Fibroblasts) activity, or a pharmaceutically acceptable salt thereof, optionally in a pharmaceutically acceptable carrier, and a medical uses thereof.

29 Claims, 20 Drawing Sheets

(56) References Cited

U.S. PATENT DOCUMENTS

| | | | |
|---|---|---|---|
| 2004/0198806 | A1 | 10/2004 | Eisai et al. |
| 2006/0154312 | A1 | 7/2006 | Agoulnik et al. |
| 2007/0244187 | A1 | 10/2007 | Austad et al. |
| 2009/0198074 | A1 | 8/2009 | Chase et al. |
| 2009/0203771 | A1 | 8/2009 | Inanaga et al. |
| 2010/0254996 | A1 | 10/2010 | Brantley-Sieders et al. |
| 2011/0054194 | A1 | 3/2011 | Hu et al. |
| 2011/0184190 | A1 | 7/2011 | Endo et al. |
| 2013/0336974 | A1 | 12/2013 | Collier et al. |
| 2014/0198806 | A1 | 7/2014 | Pani et al. |
| 2017/0137437 | A1* | 5/2017 | Kishi .................. C07D 493/22 |

FOREIGN PATENT DOCUMENTS

| | | | |
|---|---|---|---|
| WO | WO 1999/065894 A1 | 12/1999 | |
| WO | WO 2005/118565 A1 | 12/2005 | |
| WO | WO 2006/076100 A2 | 7/2006 | |
| WO | WO 2007/139149 A1 | 12/2007 | |
| WO | WO 2009/046308 A1 | 4/2009 | |
| WO | WO 2009/064029 A1 | 5/2009 | |
| WO | WO 2009/124237 A1 | 10/2009 | |
| WO | WO 2011/094339 A1 | 8/2011 | |
| WO | WO 2012/147900 A1 | 11/2012 | |
| WO | WO 2013/097042 A1 | 4/2013 | |
| WO | WO 2013/086634 A1 | 6/2013 | |
| WO | WO 2013/142999 A1 | 10/2013 | |
| WO | WO 2015/000070 A1 | 1/2015 | |
| WO | WO 2015/066729 A1 | 5/2015 | |
| WO | WO 2015/085193 A1 | 6/2015 | |
| WO | WO 2016/003975 A1 | 1/2016 | |
| WO | WO 2016/038624 A1 | 3/2016 | |
| WO | WO 2016/176560 A1 | 11/2016 | |
| WO | WO 2016/179607 A1 | 11/2016 | |

OTHER PUBLICATIONS

[No Author Listed] Evidentiary Document for Applicability of E7130 to Designation Requirements. Eisai Co., Ltd. Prepared on Nov. 22, 2017.

[No Author Listed] Overview Relating to the Suitability for Designation Requirements Under the Sakigake Designation System. Generic name E7130. Eisai Co., Ltd.

Aicher et al., Synthetic studies towards halichondrins. Tetrahedron Lett. 1987;28(30):3463-66.

Aicher et al., Synthetic Studies towards Halichondrins: Synthesis of the C.27-C.38 Segment. Tetrahedron Lett. 1992;33(12):1549-52.

Aicher et al., Total synthesis of halichondrin B and norhalichondrin B. J. Am. Chem. Soc., 1992, 114 (8), pp. 3162-3164.

Austed et al., Commercial Manufacture of Halaven®: Chemoselective Transformations En Route to Structurally Complex Macrocyclic Ketones. Synlett 2013; 24(3): 333-337. doi: 10.1055/s-0032-1318026.

Berge et al., Pharmaceutical Salts. J. Pharmaceutical Sciences 1977;66(1):1-19.

Bringans, Studies on natural product derivatives : HIV therapies incorporating marine natural products. Dissertation. University of Canterbury, 2001.

Buszek et al., Synthetic Studies Towards Halichondrins: Synthesis of the Left Half of Halichondrins. Tetrahedron Lett. 1992;33:1553.

Chen et al., Ni(II)/Cr(II)-mediated coupling reaction: an asymmetric process. J. Org. Chem., 1995, 60 (17), pp. 5386-5387.

Choi et al., Asymmetric Ni(II)/Cr(II)-Mediated Coupling Reaction: Catalytic Process. Org. Lett., 2002, 4 (25), pp. 4435-4438. doi: 10.1021/o1026981x.

Choi et al., Synthetic studies on the marine natural product halichondrins. Pure Appl. Chem., 2003, vol. 75, No. 1, pp. 1-17.

Dong et al., New syntheses of E7389 C14-C35 and halichondrin C14-C38 building blocks: reductive cyclization and oxy-Michael cyclization approaches. J Am Chem Soc. Nov. 4, 2009;131(43):15642-6. doi: 10.1021/ja9058487.

Fang et al., Synthetic Studies Towards Halichondrins: Synthesis of the Left Halves of Norhalichondrins and Homohalichondrins. Tetrahedron Lett. 1992;33(12):1557-60.

Fukuyama et al., Application of a Rotor—Stator High-Shear System for Cr/Mn-Mediated Reactions in Eribulin Mesylate Synthesis. Org. Process Res. Dev., 2016, 20 (1), pp. 100-104. doi: 10.1021/acs.oprd.5b00383.

Fukuyama et al., Application of Continuous Flow for DIBAL-H Reduction and n-BuLi Mediated Coupling Reaction in the Synthesis of Eribulin Mesylate. Org. Process Res. Dev., 2016, 20 (2), pp. 503-509. doi: 10.1021/acs.oprd.5b00353.

Guo et al., Toolbox approach to the search for effective ligands for catalytic asymmetric Cr-mediated coupling reactions. J Am Chem Soc. Oct. 28, 2009;131(42):15387-93. doi: 10.1021/ja905843e.

Hirata et al., Halichondrins—antitumor polyether macrolides from a marine sponge. Pure Appl. Chem., 1986, vol. 58, No. 5, pp. 701-710.

Kaburagi et al., Effective procedure for se ective ammonolysis of monosubstituted oxiranes: application to E7389 synthesis. Tetrahedron Lett. 2007;48(51):8967-71.

Kim et al., New syntheses of E7389 C14-C35 and halichondrin C14-C38 building blocks: double-inversion approach. J Am Chem Soc. Nov. 4, 2009;131(43):15636-41. doi: 10.1021rja9058475.

Kress et al., Investigations of the intramolecular Ni(II)/Cr(II)-mediated coupling reaction: Application to the taxane ring system. Tetrahedron Letters 1993;34(38);6003-6.

Li et al., Unified Synthesis of C1-C19 Building Blocks of Halichondrins via Selective Activation/Coupling of Polyhalogenated Nucleophiles in (Ni)/Cr-Mediated Reactions. J Am Chem Soc. May 20, 2015;137(19):6226-31. doi: 10.1021/jacs.5b03499. Epub May 11, 2015.

Lill, Studies on New Zealand marine natural products. Dissertation. University of Canterbury, 1999.

Liu et al., Catalytic enantioselective Cr-mediated propargylation: application to halichondrin synthesis. Org Lett. Oct. 15, 2009;11(20):4520-3. doi: 10.1021/o19016595.

Liu et al., Dramatic improvement in catalyst loadings and molar ratios of coupling partners for Ni/Cr-mediated coupling reactions: heterobimetallic catalysts. J Am Chem Soc. Nov. 25, 2009;131(46):16678-80. doi: 10.1021/ja9079308.

Liu et al., Synthesis of Alcohols from m-Fluorophenylsulfones and Dialkylboranes: Application to the C14-C35 Building Block of E7389. Org. Lett., 2012, 14 (9), pp. 2262-2265. doi: 10.1021/o1300672q.

Namba et al., New catalytic cycle for couplings of aldehydes with organochromium reagents. Org Lett. Dec. 23, 2004;6(26):5031-3.

Shan et al., Concise and Highly Stereoselective Synthesis of the C20-C26 Building Block of Halichondrins and Eribulin. Org. Lett., 2012, 14 (2), pp. 660-663. doi: 10.1021/o1203373d.

Stamos et al., Ni(II)/Cr(II)-Mediated Coupling Reaction: Beneficial Effects of 4-tert-Butylpyridine as an Additive and Development of New and Improved Workup Procedures. Tetrahedron Lett. 1997;38(36):6355-8.

Ueda et al., Total synthesis of halichondrin a, the missing member in the halichondrin class of natural products. J Am Chem Soc. Apr. 2, 2014;136(13):5171-6. doi: 10.1021/ja5013307. Epub Mar. 19, 2014.

Uemura et al., Norhalichondrin A: an antitumor polyether macrolide from a marine sponge. J. Am. Chem. Soc., 1985, 107 (16), pp. 4796-4798. doi: 10.1021/ja00302a042.

Uemura, Exploratory research on bioactive natural products with a focus on biological phenomena. Proc Jpn Acad Ser B Phys Bial Sci. 2010;86(3):190-201.

Wan et al., Asymmetric Ni(II)/Cr(II)-mediated coupling reaction: stoichiometric process. Org Lett. Dec. 12, 2002;4(25):4431-4.

Yamamoto et al., Total synthesis of halichondrin C. J Am Chem Soc. Jan. 18, 2012;134(2):8936. doi: 10.1021/ja2108307. Epub Dec. 23, 2011.

Yan et al., Selective Activation/Coupling of Polyhalogenated Nucleophiles in Ni/Cr-Mediated Reactions: Synthesis of C1-C19 Building Block of Halichondrin Bs. J. Am. Chem. Soc., 2015, 137 (19), pp. 6219-6225.

(56) References Cited

OTHER PUBLICATIONS

Zheng et al., Macrocyclic ketone analogues of halichondrin B. Bioorg Med Chem Lett. Nov. 15, 2004;14(22):5551-4.

* cited by examiner

| Compound | *in vitro* cell growth inhibition IC$_{50}$ (nM) | | | | | P-gp susceptibility |
|---|---|---|---|---|---|---|
| | Esophageal cancer | | | Uterine sarcoma | | |
| | OE21 | OE33 | TE-8 | MES-SA | MES-SA/Dx5-Rx1 | |
| Compound (I) | 0.061 | 0.29 | 0.095 | 0.070 | 8.7 | 123 |

MACROCYCLIC COMPOUND AND USES THEREOF

RELATED APPLICATIONS

This application claims priority under 35 U.S.C. § 119(e) to U.S. Provisional Patent Applications, U.S. Ser. No. 62/482,030, filed Apr. 5, 2017, and U.S. Ser. No. 62/526,677, filed Jun. 29, 2017; the entire contents of each of which is incorporated herein by reference.

TECHNICAL FIELD

The present invention provides a novel macrocyclic compound having tumor vascular remodeling effects and anti-CAF (Cancer Associated Fibroblast) activity. The compound can be used for treating cancer or inhibiting tumor growth in a subject.

BACKGROUND

Halichondrins, such as Halichondrin B, are anticancer agents originally isolated from the marine sponge *Halichondria okadai* (See, e.g., D. Uemura et al. "Norhalichondrin A: An Antitumor Polyether Macrolide from a Marine Sponge" J. Am. Chem. Soc., 107, 4796 (1985)), and subsequently found in *Axinella* sp., *Phakellia carteri*, and *Lissondendryx* sp. A total synthesis of Halichondrin B was published in 1992 (See, e.g., Y. Kishi et al. "Total Synthesis of Halichondrin B and Norhalichondrin B" J. Am. Chem. Soc., 114, 3162 (1992)). Halichondrin B has demonstrated in vitro inhibition of tubulin polymerization, microtubule assembly, beta 5-tubulin crosslinking, GTP and vinblastine binding to tubulin, and tubulin-dependent GTP hydrolysis, and has shown in vitro and in vivo anti-cancer properties (See, e.g., Y. Hirata et al. "Halichondrins-antitumor polyether macrolides from a marine sponge" Pure Appl. Chem., 58, 701 (1986); Fodstad et al. "Comparative antitumor activities of halichondrins and vinblastine against human tumor xenografts" J. of Experimental Therapeutics & Oncology 1996; 1: 119, 125).

Eribulin mesylate (Halaven™), which was developed based on Halichondrin B (See, e.g., International Publication No. WO 1999/065894, published Dec. 23, 1999; International Publication No. WO 2005/118565, published Dec. 15, 2005; and W. Zheng et al. "Macrocyclic ketone analogues of halichondrin B" Bioorganic & Medicinal Chemistry Letters 14, 5551-5554 (2004)), is currently in clinical use in many countries for the treatment of, e.g., metastatic breast cancer and advanced liposarcoma.

Additional patent publications describing Halichondrins include U.S. Pat. No. 5,436,238 to Kishi, et al., issued Jul. 25, 1995; U.S. Pat. No. 5,338,865 to Kishi, et al., issued Aug. 16, 1994; and WO 2016/003975 filed by Kishi, et al., all of which are assigned to the President and Fellows of Harvard College.

See also, e.g., U.S. Pat. No. 5,786,492; U.S. Pat. No. 8,598,373; U.S. Pat. No. 9,206,194; U.S. Pat. No. 9,469,651; WO/2009/124237A1; WO/1993/017690A1; WO/2012/147900A1; U.S. Pat. No. 7,982,060; U.S. Pat. No. 8,618,313; U.S. Pat. No. 9,303,050; U.S. Pat. No. 8,093,410; U.S. Pat. No. 8,350,067; U.S. Pat. No. 8,975,422; U.S. Pat. No. 8,987,479; U.S. Pat. No. 8,203,010; U.S. Pat. No. 8,445,701; U.S. Pat. No. 8,884,031; U.S. Pat. No. RE45,324; U.S. Pat. No. 8,927,597; U.S. Pat. No. 9,382,262; U.S. Pat. No. 9,303,039; WO/2009/046308A1; WO/2006/076100A3; WO/2006/076100A2; WO/2015/085193A1; WO/2016/176560A1; U.S. Pat. No. 9,278,979; U.S. Pat. No. 9,029,573; WO/2011/094339A1; WO/2016/179607A1; WO/2009/064029A1; WO/2013/142999A1; WO/2015/066729A1; WO/2016/038624A1; and WO/2015/000070A1.

Cancer associated fibroblasts (CAFs), which are widely found in a variety of solid tumors, are stromal cells. It is well known that CAFs play an important role in angiogenesis, invasion, and metastasis. It is reported that there is a close correlation between the amounts of CAFs and clinical prognosis in, for example, invasive breast cancer (See, e.g., M. Yamashita et al. "Role of stromal myofibroblasts in invasive breast cancer: stromal expression of alpha-smooth muscle actin correlates with worse clinical outcome" Breast Cancer 19, 170, 2012) and esophageal adenocarcinoma (See, e.g., T. J. Underwood et al. "Cancer-associated fibroblasts predict poor outcome and promote periostin-dependent invasion in esophageal adenocarcinoma" Journal of Pathol., 235, 466, 2015). It has also been reported that CAFs correlate to resistance in a variety of tumors such as, for example, breast cancer (See, e.g., P. Farmer et al. "A stroma-related gene signature predicts resistance to neoadjuvant chemotherapy in breast cancer" Nature Medicine., 15(1), 68, 2009), and head and neck cancer (See, e.g., S. Schmitz et al. "Cetuximab promotes epithelial to mesenchymal transition and cancer associated fibroblasts in patients with head and neck cancer" Oncotarget, 6 (33), 34288, 2015; Y. Matsuoka et al. "The tumor stromal features are associated with resistance to 5-FU-based chemoradiotherapy and a poor prognosis in patients with oral squamous cell carcinoma" APMIS 123(3), 205, 2015).

It has thus been observed that tumor vascular remodeling effects and anti-CAF activity result in the improvement of the cancer microenvironment, which assists tumor treatment. Blood vessels are essential for the growth of tumors. Reconstructed blood vessels in tumors can deliver anticancer agents to the tumors, in addition to achieving alleviation of hypoxia. It is reported that eribulin-induced remodeling of abnormal tumor vasculature leads to a more functional microenvironment that may reduce the aggressiveness of tumors due to elimination of inner tumor hypoxia. Because abnormal tumor microenvironments enhance both drug resistance and metastasis, the apparent ability of eribulin to reverse these aggressive characteristics may contribute to its clinical benefits (See, e.g., Y. Funahashi et al. "Eribulin mesylate reduces tumor microenvironment abnormality by vascular remodeling in preclinical human breast cancer models" Cancer Sci. 105 (2014), 1334-1342). Anti-cancer drugs having tumor vascular remodeling effects and anti-CAF activities have not been reported as of today.

Despite the progress made, additional compounds are needed to progress research and medical care of tumors and cancer.

SUMMARY OF THE INVENTION

The present invention relates to a macrocyclic compound (e.g., Compound (1)) having tumor vascular remodeling effects and anti-CAF activity, and pharmaceutically acceptable salts thereof, and isotopically labeled derivatives thereof, and pharmaceutical compositions thereof.

The invention also includes methods of using Compound (1) for treating cancer, methods for reversibly or irreversibly inhibiting mitosis in a cell, and methods for inhibiting tumor growth in vitro, in vivo, or in a subject. In another aspect, the present invention provides kits comprising Compound (1), or a pharmaceutically acceptable salt thereof, or a pharmaceutical composition thereof.

In one aspect, the invention features a compound which is Compound (1):

Compound (1)

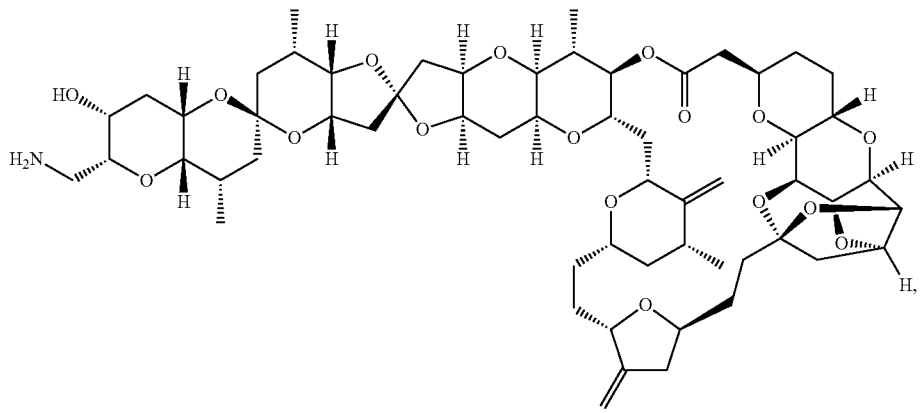

and pharmaceutically acceptable salts thereof; and isotopically labeled derivatives thereof.

In one aspect, the invention provides pharmaceutical compositions comprising Compound (1), or a pharmaceutically acceptable salt or isotopically labeled derivative thereof. The pharmaceutical compositions may comprise one or more pharmaceutically acceptable excipients or carriers. The pharmaceutical compositions may further comprise one or more additional therapeutic agents in combination, alternation, or other kind of synchronized therapy, to achieve the desired goal of treatment.

The invention also features methods of making Compound (1) or its intermediates. The synthetic intermediates are also provided herein as part of the invention.

It has been discovered that Compound (1) has an advantageous effect on tumor vascular remodeling and has anti-CAF activity, as demonstrated in the Figures and Examples. Accordingly, the Compound (1) has potential use in the treatment of cancer (e.g., squamous cell carcinoma of the head and neck (SCCHN), breast cancer, esophageal cancer, uterine cancer, ovarian cancer, or colorectal cancer).

In another aspect, the present invention provides methods for inhibiting any tumor growth or cancer that will respond to a compound with tumor vascular remodeling effects and/or anti-CAF activity, in a subject, typically a human, with Compound (1) or a pharmaceutically acceptable salt, or isotopically labeled derivative thereof.

Compound (1), or a pharmaceutically acceptable salt, or isotopically labeled derivative thereof, or a composition thereof, may be administered in combination with any other active agent that provides beneficial results for the patient. In one embodiment, Compound (1) is used in combination, alternation, or other synchronized therapy with an immunotherapy, such as an anti-EGFR (epidermal growth factor receptor) antibody, an anti-HER2 (human epidermal growth factor receptor) antibody, an anti-PD-1 antibody, or an anti-PD-L1 antibody, as described in more detail below.

For example, a method is provided to treat squamous cell carcinoma of the head and neck (SCCHN) in a subject, typically a human, in need thereof comprising administering to the subject an effective amount of Compound (1), or a pharmaceutically acceptable salt, or isotopically labeled derivative thereof, or a composition thereof, in combination with an anti-EGFR (epidermal growth factor receptor) mAb therapy. In certain embodiments, the anti-EGFR (epidermal growth factor receptor) mAb is cetuximab.

As another example, a method to treat breast cancer in a subject, typically a human, in need thereof comprising administering to said subject an effective amount of Compound (1), or a pharmaceutically acceptable salt, or isotopically labeled derivative thereof, or a composition thereof, in combination with an HER2 (human epidermal growth factor receptor) mAb therapy. In certain embodiments, the HER2 (human epidermal growth factor receptor) mAb is trastuzumab. In other embodiments, the Compound (1) may be used to treat breast cancer in combination with traditional chemotherapy such as adriamycin, cyclophosphamide, taxol, etc., or an anti-estrogen such as a selective estrogen modulator (SERM), a selective estrogen degrader (SERD), a partial or total estrogen inhibitor (such as fulvestrant) or a CDK 4/6 inhibitor such as palbociclib (Pfizer).

Another aspect of the present invention provides Compound (1), or a pharmaceutically acceptable salt, or isotopically labeled derivative thereof, which may be in the form of a hydrate, solvate, polymorph, or a composition thereof, in a kit, which may be a dosage form package. The kits described herein may include a single dose or multiple doses of the compound or pharmaceutical composition thereof. A kit of the invention may include instructions for using the provided therapeutic dosage forms (e.g., instructions for using the compound or pharmaceutical composition included in the kit).

The present invention thus includes at least the following features:

(i) Compound (1), or its pharmaceutically acceptable salt or isotopically labeled derivative, which may be optionally be in the form of a hydrate, solvate, or polymorph;

(ii) A method for treatment that includes administering an effective amount to a subject such as a human of Compound (1), or its pharmaceutically acceptable salt or isotopically labeled derivative, which may be optionally be in the form of a hydrate, solvate or polymorph, to treat head and neck cancer (e.g., squamous cell carcinoma of the head and neck (SCCHN)), breast cancer, esophageal cancer (e.g., esophageal adenocarcinoma), uterine cancer (e.g., uterine sarcoma), ovarian cancer, colorectal cancer, or sarcoma;

(iii) A method for treatment that includes administering an effective amount to a subject such as a human of Compound (1), or its pharmaceutically acceptable salt or isotopically labeled derivative, which may be optionally be in the form of a hydrate, solvate or polymorph, for use in treating a medical disorder such as a cancer or tumor that responds to vascular remodeling effects and/or anti-CAF activity;

(iv) Compound (1), or its pharmaceutically acceptable salt or isotopically labeled derivative, which may be optionally be in the form of a hydrate, solvate or polymorph, for use to treat squamous cell carcinoma of the head and neck (SCCHN), breast cancer, esophageal cancer, uterine cancer, ovarian cancer, colorectal cancer, or a sarcoma;

(v) Compound (1), or its pharmaceutically acceptable salt or isotopically labeled derivative, which may be optionally be in the form of a hydrate, solvate or polymorph, for use in treating a medical disorder such as a cancer or tumor that responds to vascular remodeling effects and/or anti-CAF activity;

(vi) A deuterated derivative of Compound (1);

(vii) A process for manufacturing a medicament intended for the therapeutic use for treating or preventing disorders such as a cancer or tumor that responds to vascular remodeling effects and/or anti-CAF activity, characterized in that Compound (1), or its pharmaceutically acceptable salt or isotopically labeled derivative, which may be optionally be in the form of a hydrate, solvate or polymorph described above, or an embodiment of the active compound, is used in the manufacture;

(viii) Compound (1), or its pharmaceutically acceptable salt or isotopically labeled derivative, in substantially pure form (e.g., at least 90 or 95%);

(ix) A pharmaceutically acceptable composition of Compound (1), or its pharmaceutically acceptable salt or isotopically labeled derivative, which may be optionally be in the form of a hydrate, solvate or polymorph, in a pharmaceutically acceptable carrier or excipient;

(x) A pharmaceutically acceptable dosage form of Compound (1), or its pharmaceutically acceptable salt or isotopically labeled derivative, which may be optionally be in the form of a hydrate, solvate or polymorph, optionally in a pharmaceutically acceptable carrier or excipient;

(xi) Compound (1), or its pharmaceutically acceptable salt or isotopically labeled derivative, to treat a disorder described herein whereby it acts through a mechanism other than vascular remodeling effects and/or anti-CAF activity of action; and (xii) Methods for the manufacture of the compounds described herein, and intermediates in the synthesis.

BRIEF DESCRIPTION OF THE DRAWINGS

The accompanying drawings, which are incorporated in and constitute a part of this specification, illustrate several embodiments of the invention and together with the description, provide non-limiting examples of the invention.

FIG. 6A. Nude mice were implanted with luciferase-transduced HSC-2 ($1 \times 10^6$ cells/spot) in tongue. The amount of luciferase-transduced HSC-2 was analyzed using In Vivo Imaging System (IVIS). Data show the bioluminescence levels in tongue in each mouse. FIG. 6B. Representative bioluminescence image of 16 mice. CDDP, CTX, CDDP+CTX were used for as comparators, which are currently used in treatment of SCCHN cancer patient treatment. CDDP=cisplatin, CTX=cetuximab.

FIG. 7A. Nude mice were implanted with luciferase-transduced HSC-2 ($1 \times 10^6$ cells/spot) in tongue. Data show the survival curve until Day 100 after treatment of drugs (n=16). *P<0.0001 versus Compound (1) or CTX alone (Log-rank (Mantel-Cox) test). FIG. 7B. The amount of luciferase-transduced HSC-2 was analyzed using In Vivo Imaging System (IVIS). Bioluminescence images of 10 survived mice of Compound (1)+CTX combination group on Day 100. RBW=relative body weight. CDDP=cisplatin, CTX=cetuximab.

FIG. 8A. Nude mice were subcutaneously implanted with luciferase-transduced FaDu ($5 \times 10^6$ cells/spot) in the right thighs. Thirteen days after the inoculation, mice were randomly assigned (n=6), and intravenously injected with Compound (1) at 90 µg/kg on Day 1 and Day 8 with or without RT of 18 Gy on Day 4 and Day 11. The amount of luciferase-transduced FaDu was analyzed using In Vivo Imaging System (IVIS). Data show the mean relative bioluminescence level to Day 1 and SEM (n=6). SEM=standard error of the mean. *P<0.05 versus non-treated on Day 29 (unpaired t-test). FIG. 8B. Representative bioluminescence images of 6 mice each group on Day 29. RT=radiation therapy.

DEFINITIONS

Figure 1:
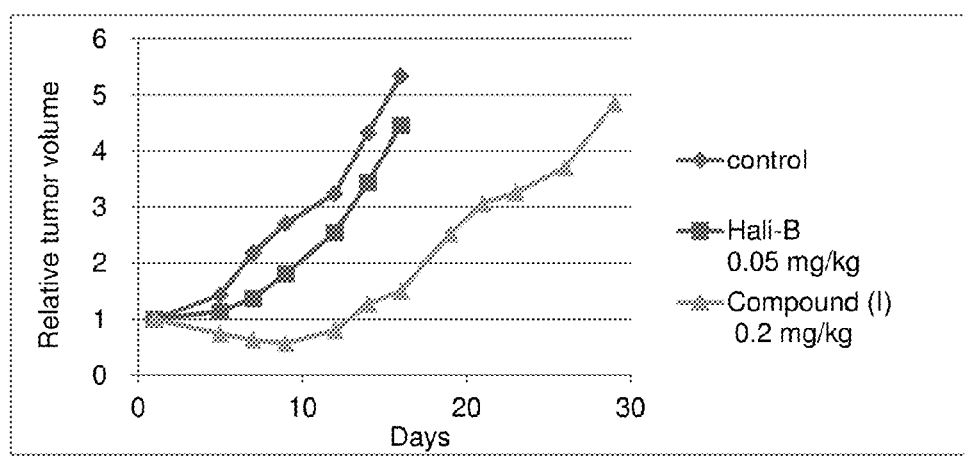
FIG. 1 shows antitumor effects of Compound (1) in FaDu subcutaneous xenograft model (head and neck cancer) in mice as monotherapy as described in Pharmacological Test Example 4.
Figure 2:
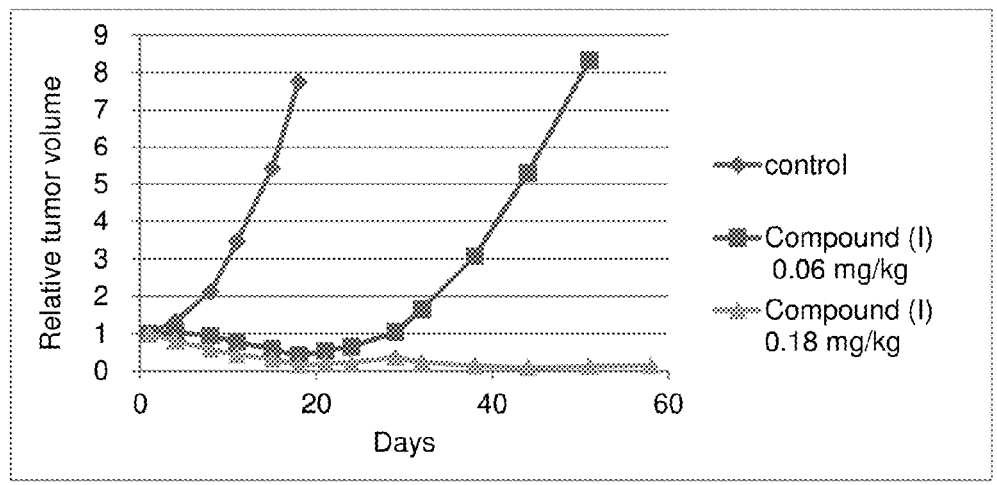
FIG. 2 shows antitumor activity of Compound (1) against OSC-19 subcutaneous xenograft model (head and neck cancer) in mice as monotherapy as described in Pharmacological Test Example 5.
Figure 3:
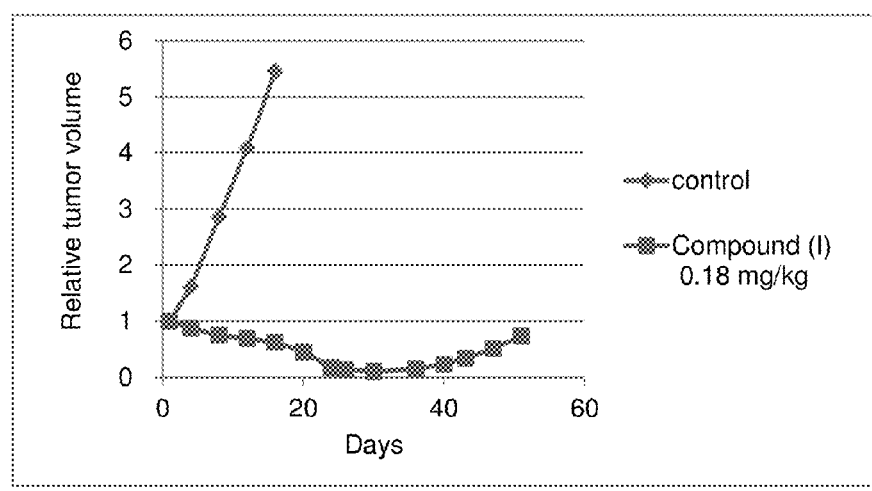
FIG. 3 shows antitumor activity of Compound (1) against HCC-1806 subcutaneous xenograft (breast cancer) model in mice as monotherapy as described in Pharmacological Test Example 6.
Figure 4:
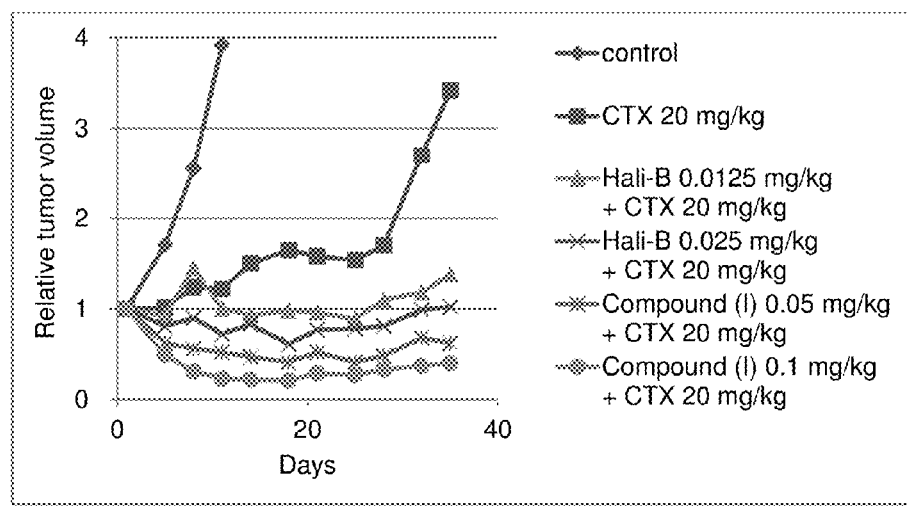
FIG. 4 shows antitumor effects of Compound (1) in FaDu subcutaneous xenograft model in combination with cetuximab in mice as described in Pharmacological Test Example 7.
Figure 5:
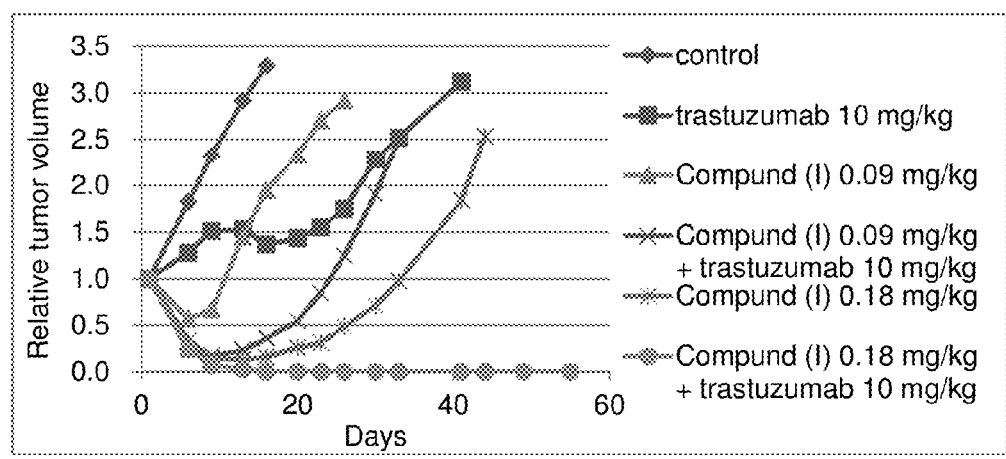
FIG. 5 shows antitumor activity of Compound (1) in KPL-4 subcutaneous xenograft model (breast cancer) in combination with trastuzumab in mice as described in Pharmacological Test Example 8.

As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Compound (1) is also provided, and can be administered, as a free base.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms. Treatment may also be continued after symptoms have resolved, for example, to delay or prevent recurrence.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. Alternatively, in a separate method or use, the invention may be used, where indicated and effective, as a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for treating in any disease or condition described.

As used herein, "inhibition", "inhibiting", "inhibit" and "inhibitor", and the like, refer to the ability of a compound to reduce, slow, halt, or prevent the activity of a biological process (e.g., tumor growth). In certain embodiments, the inhibition is about 45% to 50%. In certain embodiments, the inhibition is about 5%, 10%, 15%, 20%, 25%, 30%, 35%, 40%, 45%, 50%, 55%, 60%, 65%, 70%, 75%, 80%, 85%, 90%, 95%, 99.9%, or 100%.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located.

The term "cancer" refers to a class of diseases characterized by the development of abnormal cells that proliferate uncontrollably and have the ability to infiltrate and destroy normal body tissues.

DETAILED DESCRIPTION OF CERTAIN EMBODIMENTS

The present invention is described in detail below with reference to embodiments and the like of the present invention. The invention provides compounds (e.g., Compound (1)), and pharmaceutically acceptable salts or isotopically labeled derivatives thereof, and pharmaceutical compositions thereof. The invention also provides methods of inhibiting tumor growth and/or treating cancer in a subject comprising administering an effective amount to the subject of a compound or composition provided herein. The compound or composition may be administered as a monotherapy or in combination with another therapy, as described herein. In yet another aspect, the present invention provides methods of preparing Compound (1), and synthetic intermediates useful to that end.

The invention includes a compound of the structure:

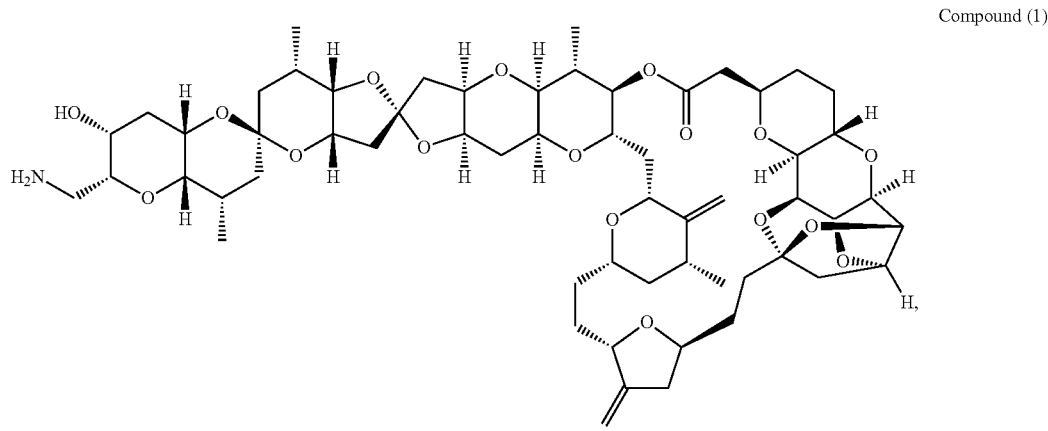

Compound (1)

or its pharmaceutically acceptable salt or isotopically labeled derivative, which may be optionally be in the form of a hydrate, solvate or polymorph, optionally in a pharmaceutically acceptable carrier or excipient.

Compound (1) may exist as a crystal polymorph, and the compound of the present invention may be in any of single crystal forms or a mixture of two or more crystal forms. Compound (1) can be in an amorphous form, or can be an anhydride or a solvate, such as a hydrate.

The present invention includes isotopically labeled derivatives of Compound (1) and pharmaceutically acceptable salts thereof. The isotopically labeled compound is equivalent to Compound (1) except that one or more of atom(s) are replaced by atom(s) having an atomic mass or a mass number different from those usually found in nature. Examples of an isotope that can be incorporated into the compound of the present invention include isotopes of hydrogen, carbon, nitrogen, oxygen, phosphorus, fluorine, iodine, bromine and chlorine, such as $^{2}$H, $^{3}$H, $^{11}$C, $^{13}$C $^{14}$C $^{18}$F, $^{35}$S, $^{123}$I, and $^{125}$I.

The isotopically labeled compound, such as a compound into which a radioactive isotope of, for example, $^{3}$H and/or $^{14}$C is incorporated, is useful for a tissue distribution assay for a medicine and/or a matrix. The isotopes $^{3}$H and $^{14}$C are regarded to be useful because these isotopes can be easily prepared and detected. The isotopes $^{11}$C and $^{18}$F are useful in PET (positron emission tomography). The isotope $^{125}$I is regarded to be useful in SPECT (single photon emission computed tomography), and can be useful in brain imaging. Replacement by a heavier isotope such as $^2$H causes, because of its higher metabolic stability, some advantages, in a treatment, of, for example, extension of half-life in vivo or reduction of a necessary dose, and therefore, is regarded useful under given circumstances. The isotopically labeled compound can be similarly prepared by using a readily available isotopically labeled reagent instead of a non-isotopically labeled reagent and by performing processes disclosed in schemes and/or examples described below.

Compound (1) can be used as a chemical probe for capturing a target protein of a biologically active low molecular weight compound. Specifically, the compound of the present invention can be transformed into an affinity chromatography probe, a photoaffinity probe or the like by introducing a labeling group, a linker or the like into a moiety other than a structural moiety indispensable to activity expression of the compound by a method described in *J. Mass Spectrum. Soc. Jpn.* Vol. 51, No. 5, 2003, p. 492-498, WO2007/139149, or the like.

Examples of the labeling group, the linker or the like used in such a chemical probe include groups belonging to the following groups (1) to (5). (1) Protein labeling groups such as photoaffinity labeling groups (such as a benzoyl group, a benzophenone group, an azide group, a carbonyl azide group, a diaziridine group, an enone group, a diazo group and a nitro group), and chemical affinity groups (such as a ketone group in which an alpha carbon atom is substituted by a halogen atom, a carbamoyl group, an ester group, an alkylthio group, a Michael acceptor of α,β-unsaturated ketone, ester, or the like, and an oxirane group); (2) cleavable linkers such as S—S, O—Si—O, a monosaccharide (such as a glucose group or a galactose group) and a disaccharide (such as lactose), and oligopeptide linkers that can be cleaved by an enzyme reaction; (3) fishing tag groups such as biotin and a 3-(4, 4-difluoro-5,7-dimethyl-4H-3a, 4a-diaza-4-bora-s-indacene-3-yl)propionyl group; (4) radioactive labeling groups such as $^{125}$I, $^{32}$P $^3$H and $^{14}$C; fluorescence labeling groups such as fluorescein, rhodamine, dansyl, umbelliferone, 7-nitrofurazanyl, and a 3-(4,4-difluoro-5,7-dimethyl-4H-3a,4a-diaza-4-bora-s-indacene-3-yl) propionyl group; chemiluminescent groups such as luciferin and luminol; and markers capable of detecting heavy metal ions such as lanthanoid metal ions and radium ions; and (5) groups to be bonded to a solid phase carrier such as glass beads, a glass bed, a microliter plate, agarose beads, an agarose bed, polystyrene beads, a polystyrene bed, nylon beads and a nylon bed.

A probe prepared by introducing, into the compound of the present invention, a labeling group or the like selected from the above-described groups (1) to (5) by the method described in any of the aforementioned literatures or the like can be used as a chemical probe for identifying a marker protein useful for research of a novel potential drug target.

Examples of a "salt" used herein include salts with inorganic acids, salts with organic acids, and salts with acidic amino acids, and in particular, pharmaceutically acceptable salts are preferred. Besides, a salt of the compound of the present invention embraces an anhydride of a pharmaceutically acceptable salt thereof and a solvate, such as a hydrate, of the pharmaceutically acceptable salt. Preferable examples of a salt with an inorganic acid include salts with hydrochloric acid, hydrobromic acid, sulfuric acid, nitric acid, phosphoric acid and the like, and preferable examples of a salt with an organic acid include salts with acetic acid, succinic acid, famaric acid, maleic acid, tartaric acid, citric acid, lactic acid, stearic acid, benzoic acid, methanesulfonic acid, ethanesulfonic acid, benzenesulfonic acid, p-toluenesulfonic acid and the like. Preferable examples of a salt with an acidic amino acid include salts with aspartic acid and glutamic acid and the like.

In the case where the compound (1) according to the present invention is obtained as a salt of the compound (1) or a hydrate of the compound (1), the salt and the hydrate can be converted to a free body of the compound (1) by a conventional method.

Pharmaceutical Compositions, Kits, and Administration

The present invention provides pharmaceutical compositions comprising Compound (1), or a pharmaceutically acceptable salt or isotopically labeled derivative thereof, and a pharmaceutically acceptable excipient. In certain embodiments, the compound described herein, or pharmaceutically acceptable salt or isotopically labeled derivative thereof, is provided in an effective amount in the pharmaceutical composition (e.g., a therapeutically effective amount).

Pharmaceutical compositions described herein can be prepared by any method known in the art of pharmacology. In general, such preparatory methods include bringing Compound (1) (i.e., the "active ingredient") into association with a carrier or excipient, and/or one or more other accessory ingredients, and then, if necessary and/or desirable, shaping, and/or packaging the product into a desired single- or multi-dose unit. A pharmaceutical composition of the invention could be prepared according to the known method such as a method described in the general rules for preparations of the *Japanese Pharmacopoeia*, 16$^{th}$ edition, *the United States Pharmacopoeia*, and the *European Pharmacopoeia*, 9$^{th}$ edition. A pharmaceutical composition of the invention could be administered to patients appropriately depending on the dosage form.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

The compound provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compound of the present invention (Compound (1)) and compositions thereof provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of Compound (1) required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell may be, in non-limiting examples, three doses a day, two doses a day, one dose a day, one dose every other day, one dose every third day, one dose every week, one dose every two weeks, one dose every three weeks, or one dose every four weeks, or even slow dose controlled delivery over a selected period of time using a drug delivery device. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is about or at least one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is about or at least three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.001 mg/kg and 0.01 mg/kg, between 0.01 mg/kg and 0.1 mg/kg, between 0.1 mg/kg and 1 mg/kg, inclusive of Compound (1). Examples are dosage forms with at least about 0.05, 0.1, 0.5, 1, 1.5, 2, 2.5, 3, 3.5, 4, 4.5, 5, 10, 5, 20, 25, 50 mg of active compound, or its salt in a dosage form.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Also encompassed by the disclosure are kits (e.g., pharmaceutical packs). The kits provided may comprise a pharmaceutical composition or Compound (1) and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or Compound (1). In some embodiments, the pharmaceutical composition or Compound (1) provided in the first container and the second container are combined to form one unit dosage form. A kit described herein may include one or more additional pharmaceutical agents described herein as a separate composition.

Methods of Treatment and Uses

As shown herein, Compound (1) has significant tumor vascular remodeling effects and anti-CAF activity, and therefore, it has potential use for the treatment of cancer and/or the inhibition of tumor growth.

Provided herein is a method of treating cancer in a subject, the method comprising administering to the subject an effective amount of a Compound (1), or a pharmaceutically acceptable salt or isotopically labeled derivative thereof, or a pharmaceutical composition thereof. The present invention also provides Compound (1), or a pharmaceutically acceptable salt or isotopically labeled derivative thereof, or a pharmaceutical composition thereof, for use in treating cancer in a subject. The present invention also provides the use of Compound (1), or a pharmaceutically acceptable salt or isotopically labeled derivative thereof, or a pharmaceutical composition thereof, for the manufacture of a medicament for the treating cancer.

Also provided herein is a method of inhibiting tumor growth in a subject, the method comprising administering to the subject Compound (1), or a pharmaceutically acceptable salt or isotopically labeled derivative thereof, or a pharmaceutical composition thereof. Also provided herein is Compound (1), or a pharmaceutically acceptable salt or isotopically labeled derivative thereof, or a pharmaceutical composition thereof, for use in inhibiting tumor growth in a subject. The present invention also provides the use of Compound (1), or a pharmaceutically acceptable salt or isotopically labeled derivative thereof, or a pharmaceutical composition thereof, for the manufacture of a medicament for inhibiting tumor growth.

In certain embodiments of the methods provided herein, the cancer is head and neck cancer (e.g., head and neck squamous cell carcinoma, oral cancer, throat cancer, salivary gland cancer, tongue cancer). In certain embodiments, the cancer is breast cancer (e.g., HER2-positive breast cancer, triple negative breast cancer). In certain embodiments, the cancer is colorectal cancer (e.g., colon carcinoma). In certain embodiments, the cancer is esophageal cancer (e.g., esophageal adenocarcinoma). In certain embodiments, the cancer is uterine cancer (e.g., uterine sarcoma). In certain embodiments, the cancer is ovarian cancer. In certain embodiments, the cancer is a sarcoma (e.g., uterine sarcoma, fibrosarcoma, angiosarcoma).

Combination Therapy

Besides administration as monotherapy, Compound (1) can be administered in combination with other therapeutic agents or treatment modalities. The compound of the present invention can be administered in combination with another therapeutic agent, such as anti-EGFR therapy, anti-HER2 therapy, anti-PD-1 therapy, anti-PD-L1 therapy, or irradiation therapy.

In certain embodiments, Compound (1), or a pharmaceutically acceptable salt or isotopically labeled derivative thereof, or a pharmaceutical composition thereof, is administered in combination with an anti-EGFR therapy (e.g., anti-EGFR monoclonal antibody (mAb), such as cetuximab). For example, provided herein is a method of treating squamous cell carcinoma of the head and neck (SCCHN) in a subject comprising administering to said subject Compound (1), or a pharmaceutically acceptable salt or isotopically labeled derivative thereof, or a pharmaceutical composition thereof, in combination with an anti-EGFR (epidermal growth factor receptor) mAb therapy. In certain embodiments, the anti-EGFR mAb is cetuximab (CTX).

In certain embodiments, Compound (1), or a pharmaceutically acceptable salt or isotopically labeled derivative thereof, or a pharmaceutical composition thereof, is administered in combination with an anti-HER2 therapy (e.g., anti-HER2 monoclonal antibody (mAb) such as trastuzumab). For example, provided herein is a method of treating breast cancer in a subject in need thereof comprising administering to said subject Compound (1), or a pharmaceutically acceptable salt or isotopically labeled derivative thereof, or a composition thereof, in combination with an HER2 (human epidermal growth factor receptor) mAb therapy. In certain embodiments, the anti-HER2 mAb is trastuzumab.

In certain embodiments, Compound (1), or a pharmaceutically acceptable salt or isotopically labeled derivative thereof, or a pharmaceutical composition thereof, is administered in combination with an anti-PD-1 or anti-PD-L1 therapy (e.g., anti-PD-1 or anti-PD-L1 monoclonal antibody). For example, provided herein is a method of treating colorectal cancer in a subject in need thereof comprising administering to said subject Compound (1), or a pharmaceutically acceptable salt or isotopically labeled derivative thereof, or a composition thereof, in combination with an anti-PD-1 or anti-PD-L1 therapy (e.g., mAb therapy). In certain embodiments, Compound (1), or a pharmaceutically acceptable salt or isotopically labeled derivative thereof, or a pharmaceutical composition thereof, is used in combination with radiation therapy (RT). In certain embodiments, the compound is administered in combination with surgery.

EXAMPLES

Synthesis of Compound (1)
General Procedures and Methods

The compound according to the present invention can be produced by the methods described in Examples below. However, these examples are only for illustrative purposes, and the compound according to the present invention is not limited to the specific examples mentioned below in any way.

In the Examples, unless specifically mentioned otherwise, the silica gel for purification by using silica gel column chromatography was Hi-Flash™ Column (Silica Gel, 30 µm 60 Å or 40 µm 60 Å, Yamazen Corporation), the silica gel for purification by using NH silica gel column chromatography was Chromatorex NH silica gel (Fuji Silysia Chemical LTD). Analytical thin layer chromatography (TLC) was performed with TLC silica gel 60 $F_{254}$, layer thickness 0.25 mm (Merck KGaA) or Chromatorex TLC NH silica gel $F_{254}$, layer thickness 0.25 mm (Fuji Silysia Chemical LTD). TLC plates were visualized by staining with p-anisaldehyde stain, phosphomolybdic acid stain or Hanessian's Stain.

All moisture sensitive reactions were conducted under an inert atmosphere. Reagents and solvents were commercial grade and were used as supplied, unless otherwise noted.

NMR spectra were recorded on a JEOL ECZ500R (500 MHz), JEOL ECZ400S (400 MHz), Varian Inova 500 (500 MHz), Varian Mercury 400 (400 MHz) or Bruker Avance (600 MHz) spectrometer. Chemical shifts are reported in parts per million (ppm). For $^1$H NMR spectra (CDCl$_3$, C$_6$D$_6$, and/or CD$_3$OD), the residual solvent peak was used as the internal reference (7.27 ppm in CDCl$_3$; 7.16 ppm in C$_6$D$_6$; 3.31 ppm in CD$_3$OD).

Analytical mass spectra (MS) results were obtained using a Waters Acquity UPLC equipped with a single quadrapole detector (SQ Detector 2) or LTQ Orbitrap XL™ (Thermoscientific).

High performance liquid chromatography (HPLC) was carried out with Shimadzu LC-10AD on a UV spectrophotometric detector (200 nm, Shimadzu SPD-10A).

The abbreviations used herein are as follows: AIBN: 2,2'-azobis(isobutyronitrile); 9-BBN: 9-borabicyclo[3.3.1]nonane; Bu$_3$SnH: tri-normal-butyltin hydride; (+)-CSA: (1S)-(+)-10-Camphorsulfonic acid; DMAP: 4-dimethylaminopyridine; DCM: dichloromethane; DDQ: 2,3-dichloro-5,6-dicyano-1,4-benzoquinone; DIBAL: diisobutylaluminium hydride; DMF: N, N-dimethylformamide; DMSO: dimethyl sulfoxide Et$_3$N: triethylamine; EtOAc: ethyl acetate; HF-Pyridine: hydrogen fluoride pyridine; HPLC: high performance liquid chromatography; IPA: isopropyl alcohol; MeCN: acetonitrile; MeOH: methanol; MPM: para-methoxybenzyl; PPh$_3$: triphenylphosphine; t-BuOH: tertiary-butyl alcohol; tBuLi: tertiary-butyl lithium; TBME: methyl tertiary-butyl ether; TBAF: tetrabutylammonium fluoride; TBS: tertiary-butyldimethylsilyl; THF: tetrahydrofuran; TMS: trimethylsilyl; Ts: para-toluenesulfonyl.

The synthetic intermediates disclosed herein are considered part of the present invention.

Scheme A; Preparation of Compound A-7

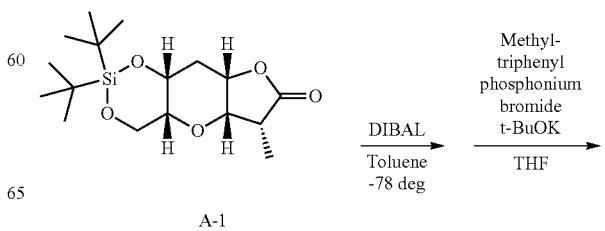

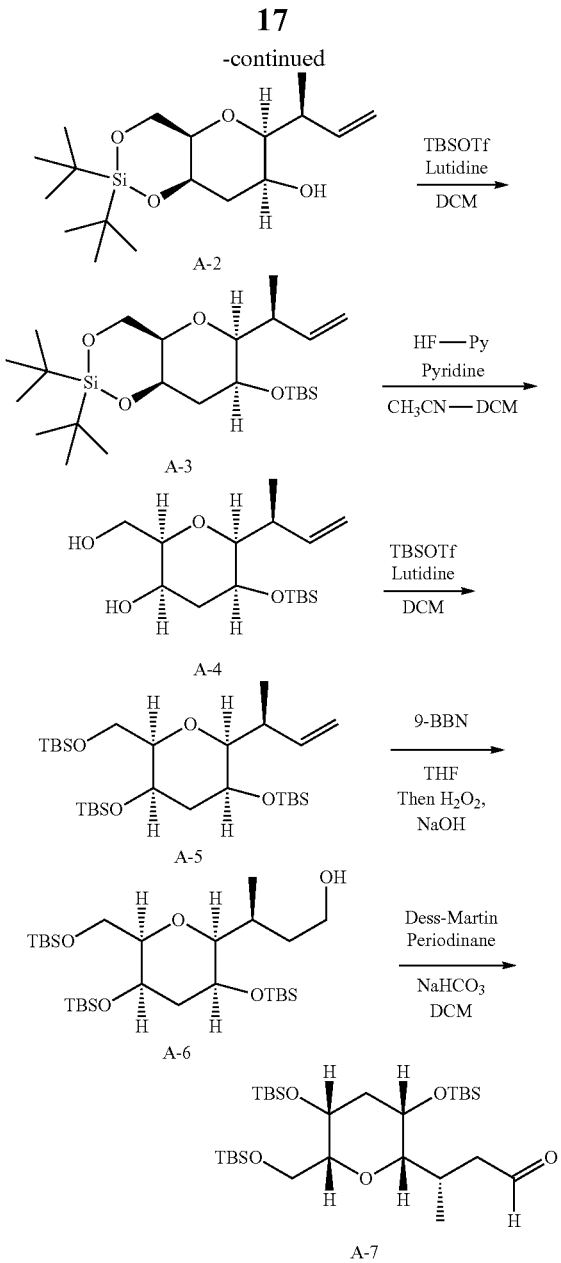

Example 1

(4aR,5aS,6R,8aS,9aR)-2,2-di-tert-butyl-6-methyloctahydrofuro[2',3':5,6]pyrano[3,2-d][1,3,2]dioxasilin-7-ol

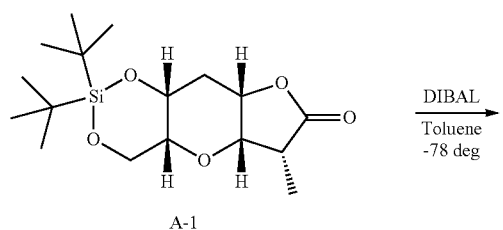

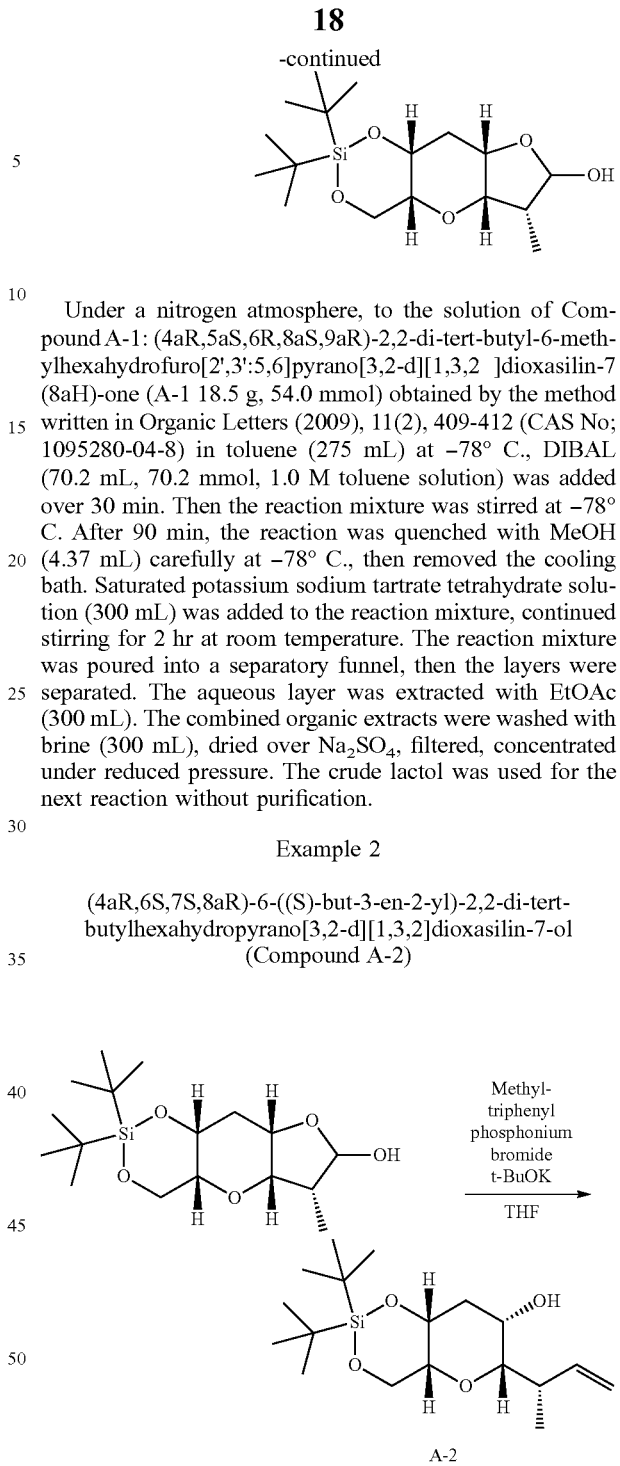

Under a nitrogen atmosphere, to the solution of Compound A-1: (4aR,5aS,6R,8aS,9aR)-2,2-di-tert-butyl-6-methylhexahydrofuro[2',3':5,6]pyrano[3,2-d][1,3,2]dioxasilin-7(8aH)-one (A-1 18.5 g, 54.0 mmol) obtained by the method written in Organic Letters (2009), 11(2), 409-412 (CAS No; 1095280-04-8) in toluene (275 mL) at −78° C., DIBAL (70.2 mL, 70.2 mmol, 1.0 M toluene solution) was added over 30 min. Then the reaction mixture was stirred at −78° C. After 90 min, the reaction was quenched with MeOH (4.37 mL) carefully at −78° C., then removed the cooling bath. Saturated potassium sodium tartrate tetrahydrate solution (300 mL) was added to the reaction mixture, continued stirring for 2 hr at room temperature. The reaction mixture was poured into a separatory funnel, then the layers were separated. The aqueous layer was extracted with EtOAc (300 mL). The combined organic extracts were washed with brine (300 mL), dried over Na₂SO₄, filtered, concentrated under reduced pressure. The crude lactol was used for the next reaction without purification.

Example 2

(4aR,6S,7S,8aR)-6-((S)-but-3-en-2-yl)-2,2-di-tert-butylhexahydropyrano[3,2-d][1,3,2]dioxasilin-7-ol (Compound A-2)

Under a nitrogen atmosphere, to the suspension of methyltriphenylphosphonium bromide (73.30 g, 205.2 mmol) in THF (200 mL), potassium tert-butoxide (17.27 g, 153.9 mmol) was added at −5° C. over 10 min, and then stirred for 60 min at −5° C. Solution of the crude lactol described in Example 1 in THF (40 mL) was transferred to the reaction mixture at −5° C. over 10 min, then stirred at −5° C. for 1 hr, at room temperature for 1 hr. The reaction mixture was quenched with ice-water (400 mL), then diluted with TBME (400 mL) and then the layers were separated. The aqueous layer was extracted with TBME (400 mL). The combined organic extracts were washed with brine (400 mL), dried over Na$_2$SO$_4$, filtered and concentrated under reduced pressure. The residue was suspended with Heptane/EtOAc=1/1 (100 mL). The resulting suspension was filtered, rinsed with Heptane/EtOAc=1/1 (100 mL) to remove triphenylphosphine derived material. Then filtrate was concentrated under reduced pressure. Flash chromatography of the residue on silica gel (400 g, Silica Gel 60, spherical, 40-50 μm, Kanto Chemical) using 0% to 20% EtOAc/Heptane gave the title compound (Compound A-2, 16.7 g, 90% yield).

$^1$H NMR (400 MHz, CHLOROFORM-d) δ ppm 1.03 (d, J=6.8 Hz, 3H) 1.05 (s, 9H) 1.07 (s, 9H) 1.75 (dt, J=14.5, 3.0 Hz, 1H) 2.37 (dt, J=14.5, 2.9 Hz, 1H) 2.65-2.76 (m, 1H) 3.03 (dd, J=9.8, 1.0 Hz, 1H) 3.31 (m, 1H) 3.69 (d, J=15.0 Hz, 1H) 3.75-3.79 (m, 1H) 4.16-4.31 (m, 2H) 4.41 (t, J=2.9 Hz, 1H) 4.95-5.09 (m, 2H) 6.02 (ddd, J=17.3, 10.5, 6.3 Hz, 1H).

Example 3

(4aR,6S,7S,8aR)-6-((S)-but-3-en-2-yl)-2,2-di-tert-butyl-7-((tert-butyldimethylsilyl)oxy)hexahydropyrano[3,2-d][1,3,2]dioxasiline (Compound A-3)

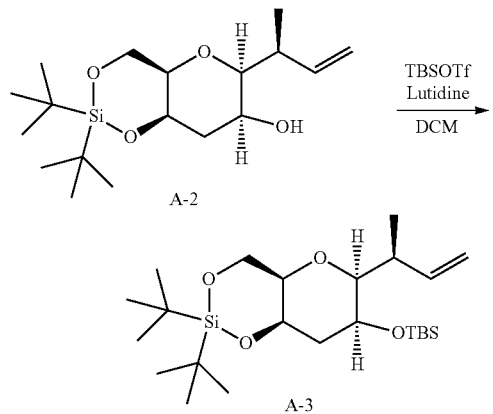

Under a nitrogen atmosphere, to a solution of Compound A-2: (4aR,6S,7S,8aR)-6-((S)-but-3-en-2-yl)-2,2-di-tert-butylhexahydropyrano[3,2-d][1,3,2]dioxasilin-7-ol (9.85 g, 28.8 mmol) described in Example 2 in DCM (150 mL) at 0° C. were added 2,6-lutidine (6.68 mL, 57.5 mmol) and tert-butyldimethylsilyl trifluoromethanesulfonate (9.25 mL, 40.3 mmol). The reaction mixture was stirred at 0° C. for 30 min, then at room temperature for 2 hr. The reaction mixture was diluted with diethyl ether. The organic layer was washed with 0.5 N HCl aq, sat.NaHCO$_3$ aq and then brine. The combined organic layers were dried over MgSO$_4$, filtered (small amount of SiO$_2$) and concentrated under reduced pressure. Flash chromatography of the residue on silica gel using 0% to 15% EtOAc/Heptane gave the title compound (Compound A-3, 12.0 g, 91% yield).

$^1$H NMR (500 MHz, CHLOROFORM-d) δ ppm 0.10 (s, 3H) 0.19 (s, 3H) 0.91 (s, 9H) 0.96 (d, J=6.3 Hz, 3H) 1.02 (s, 9H) 1.06 (s, 9H) 1.73 (dt, J=15.0, 4.0 Hz, 1H) 2.26 (dt, J=15.0, 2.5 Hz, 1H) 2.66-2.74 (m, 1H) 2.95 (dd, J=9.5, 2.2 Hz, 1H) 3.17 (m, 1H) 3.81-3.84 (m, 1H) 4.12-4.22 (m, 2H) 4.24 (t, J=2.7 Hz, 1H) 4.93-5.06 (m, 2H) 6.08 (ddd, J=17.3, 10.5, 6.3 Hz, 1H).

Example 4

(2R,3R,5S,6S)-6-((S)-but-3-en-2-yl)-5-((tert-butyldimethylsilyl)oxy)-2-(hydroxymethyl)tetrahydro-2H-pyran-3-ol (Compound A-4)

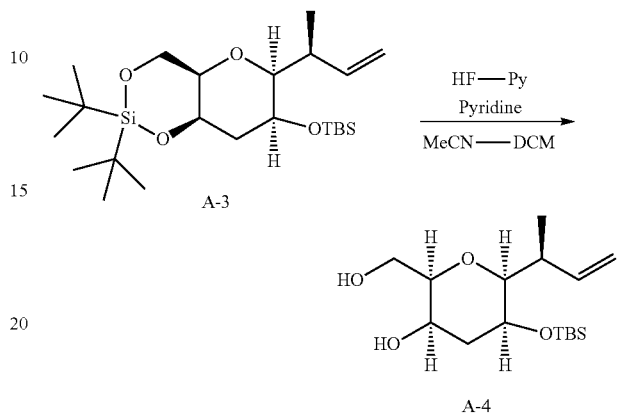

Under a nitrogen atmosphere, to a solution of Compound A-3: (4aR,6S,7S,8aR)-6-((S)-but-3-en-2-yl)-2,2-di-tert-butyl-7-((tert-butyldimethylsilyl)oxy)hexahydropyrano[3,2-d][1,3,2]dioxasiline (12 g, 26.3 mmol) described in Example 3 in MeCN (120 mL) and DCM (40 mL) at −10° C. was added pre-mixed solution of HF-Pyridine (4.0 mL) and pyridine (20 mL) in 20 mL of MeCN. The reaction mixture was stirred at −10° C. for 15 min, then at room temperature for 1 hr. The reaction mixture was quenched with sat.NaHCO$_3$ aq at 0° C. and diluted with DCM, then the layers were separated. The aqueous layer was extracted with DCM. The combined organic extracts were washed with brine. The combined organic layer was dried over MgSO$_4$, filtered and concentrated under reduced pressure. Flash chromatography of the residue on silica gel using 15% to 60% EtOAc/Heptane gave the title compound (Compound A-4, 8.4 g, Quant. yield).

$^1$H NMR (500 MHz, CHLOROFORM-d) δ ppm 0.13 (s, 3H) 0.19 (s, 3H) 0.94 (s, 9H) 0.96 (d, J=6.8 Hz, 3H) 1.72 (dt, J=14.6, 2.9 Hz, 1H) 2.15 (dd, J=9.8, 2.4 Hz, 1H) 2.23 (dt, J=14.6, 2.9 Hz, 1H) 2.55-2.65 (m, 1H) 3.03 (d, J=9.8 Hz, 1H) 3.41-3.46 (m, 1H) 3.49 (d, J=11.7 Hz, 1H) 3.62-3.72 (m, 2H) 3.92 (ddd, J=11.7, 8.3, 2.4 Hz, 1H) 4.02 (t, J=2.7 Hz, 1H) 5.01-5.12 (m, 2H) 5.93 (ddd, J=17.4, 10.4, 7.3 Hz, 1H).

Example 5

(((2S,3S,5R,6R)-2-((S)-but-3-en-2-yl)-6-(((tert-butyldimethylsilyl)oxy)methyl)tetrahydro-2H-pyran-3,5-diyl)bis(oxy))bis(tert-butyldimethylsilane) (Compound A-5)

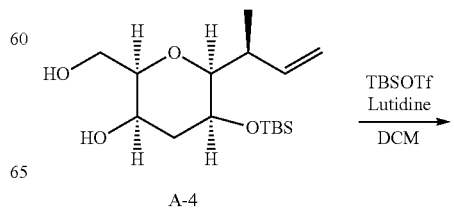

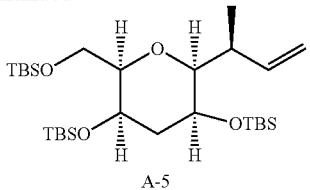

A-5

Under a nitrogen atmosphere, to a solution of Compound A-4: (2R,3R,5S,6S)-6-((S)-but-3-en-2-yl)-5-((tert-butyldimethylsilyl)oxy)-2-(hydroxymethyl)tetrahydro-2H-pyran-3-ol (997 mg, 3.15 mmol) described in Example 4 in DCM (10 mL) at 5° C. was added 2,6-lutidine (1.83 mL, 15.8 mmol) and tert-butyldimethylsilyl trifluoromethanesulfonate (2.17 mL, 9.45 mmol). The reaction mixture was stirred at room temperature for 5 hr. The reaction mixture was diluted with diethyl ether and quenched with sat. NaHCO$_3$ aq, then the layers were separated. The combined organic extracts were successively washed with 0.5 N HCl aq, sat.NaHCO$_3$ aq, and then brine. The organic layer was dried over MgSO$_4$, filtered and concentrated under reduced pressure. Flash chromatography of the residue on silica gel using 0% to 5% EtOAc/Heptane (containing 1% Et$_3$N) gave the title compound (Compound A-5, 1.69 g, 98% yield).

$^1$H NMR (500 MHz, CHLOROFORM-d) δ ppm 0.02-0.08 (m, 15H) 0.11 (s, 3H) 0.89 (s, 9H) 0.90-0.92 (m, 18H) 0.94 (d, J=6.8 Hz, 3H) 1.82 (dt, J=14.9, 4.8 Hz, 1H) 2.00 (dt, J=14.9, 2.9 Hz, 1H) 2.62-2.72 (m, 1H) 2.93 (dd, J=9.3, 2.0 Hz, 1H) 3.27-3.34 (m, 1H) 3.66-3.79 (m, 3H) 3.83-3.87 (m, 1H) 4.91-5.07 (m, 2H) 6.11 (ddd, J=17.3, 10.7, 6.1 Hz, 1H).

Example 6

(S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butan-1-ol (Compound A-6)

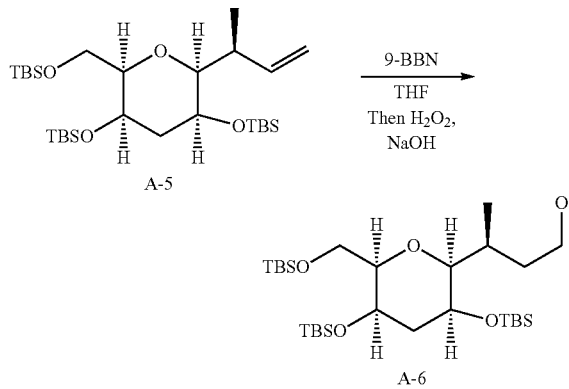

To a solution of Compound A-5: (((2S,3S,5R,6R)-2-((S)-but-3-en-2-yl)-6-(((tert-butyldimethylsilyl)oxy)methyl)tetrahydro-2H-pyran-3,5-diyl)bis(oxy))bis(tert-butyldimethylsilane) (1.32 g, 2.42 mmol) described in Example 5 in THF (10 mL) at 0° C. was added 9-BBN (9.69 mL, 0.5 M THF solution, 4.84 mmol). The reaction mixture was stirred at 0° C. for 1 hr and at room temperature for 1.5 hr. 3.0 M NaOH aq (3 mL, 9.00 mmol) and hydrogen peroxide (35% in water, 3 mL) were added to the reaction mixture at 0° C. The reaction mixture was stirred at 0° C. for 30 min, then at room temperature for 1 hr. The reaction mixture was quenched with sat. Na$_2$SO$_3$ aq and then the layers were separated. The aqueous layer was extracted with EtOAc (3 times). The combined organic extracts were washed with brine, dried over Na$_2$SO$_4$, filtered and concentrated under reduced pressure. Flash chromatography of the residue on silica gel using 0% to 20% EtOAc/Heptane gave the title compound (Compound A-6, 1.36 g, 100% yield).

$^1$H NMR (500 MHz, CHLOROFORM-d) δ ppm 0.03 (s, 3H) 0.05-0.08 (m, 12H) 0.10 (s, 3H) 0.88 (d, J=6.8 Hz, 3H) 0.89-0.93 (m, 27H) 1.55-1.65 (m, 1H) 1.82 (dt, J=15.4, 4.4 Hz, 1H) 1.87-1.96 (m, 1H) 1.97-2.03 (m, 1H) 2.17-2.26 (m, 1H) 2.67 (dd, J=7.8, 3.9 Hz, 1H) 2.98-3.10 (m, 1H) 3.34-3.40 (m, 1H) 3.59-3.86 (m, 6H) ESI-MS (m/z): 563.64 [M+H]$^+$, 585.62 [M+Na]$^+$ Example 7

(S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butanal (Compound A-7)

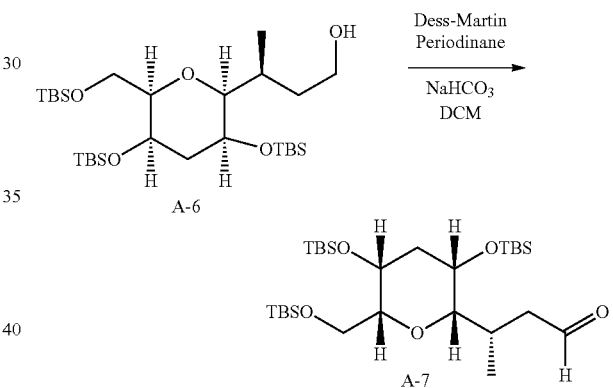

Under a nitrogen atmosphere, to a solution of Compound A-6: (S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butan-1-ol (1100 mg, 1.954 mmol) described in Example 6 in DCM (30 mL) at 5° C. were added NaHCO$_3$ (41.0 mg, 0.49 mmol) and Dess-Martin periodinane (1077 mg, 2.54 mmol). The reaction mixture was stirred at room temperature. After 3 hr, the reaction mixture was diluted with DCM and quenched with sat.NaHCO$_3$ aq and sat. Na$_2$SO$_3$ aq, then the layers were separated. The aqueous layer was extracted with DCM. The combined organic extracts were washed with brine, dried over MgSO$_4$, filtered and concentrated under reduced pressure. Flash chromatography of the residue on silica gel using 0% to 25% EtOAc/Heptane gave the title compound (Compound A-7, 950 mg, 87% yield).

$^1$H NMR (500 MHz, CHLOROFORM-d) δ ppm 0.00 (s, 3H) 0.03-0.08 (m, 12H) 0.11 (s, 3H) 0.88 (s, 9H) 0.91-0.92 (m, 21H) 1.82 (dt, J=15.0, 4.5 Hz, 1H) 2.01 (dt, J=15.0, 2.5 Hz, 1H) 2.28 (ddd, J=16.0, 7.3, 2.4 Hz, 1H) 2.53-2.58 (m, 1H) 2.74 (ddd, J=16.0, 5.5, 2.0 Hz, 1H) 2.94 (dd, J=9.0, 1.7 Hz, 1H) 3.29 (td, J=5.9, 2.0 Hz, 1H) 3.68 (d, J=5.9 Hz, 2H) 3.75-3.82 (m, 1H) 3.82-3.90 (m, 1H) 9.73 (t, J=2.4 Hz, 1H).

Scheme B: Preparation of Compound B-3

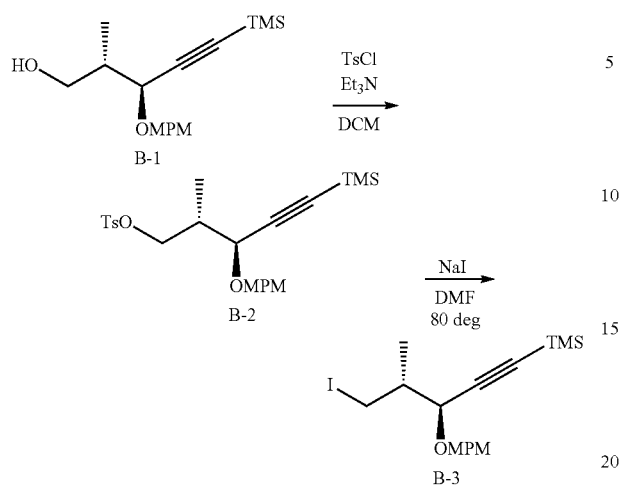

Example 8

(2S,3S)-3-((4-methoxybenzyl)oxy)-2-methyl-5-(trimethylsilyl)pent-4-yn-1-yl 4-methylbenzenesulfonate (Compound B-2)

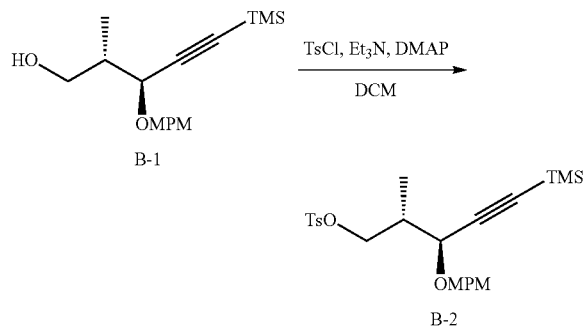

Under a nitrogen atmosphere, to the solution of Compound B-1: (2S,3S)-3-((4-methoxybenzyl)oxy)-2-methyl-5-(trimethylsilyl)pent-4-yn-1-ol (11.08 g, 36.15 mmol) obtained by the method written in WO 9317690 A1/U.S. Pat. No. 5,436,238 A (CAS No; 157323-41-6) in DCM (330 mL), Et$_3$N (12.6 mL, 90.4 mmol) and p-toluenesulfonyl chloride (8.27 g, 43.4 mmol) were added at room temperature. The reaction mixture was stirred at room temperature overnight. The mixture was washed with sat.NaHCO$_3$ and brine, dried over MgSO$_4$, filtered, then concentrated under reduced pressure. Flash chromatography of the residue on silica gel (Silica Gel 60, spherical, 40-50 μm, Kanto Chemical) using 0% to 10% EtOAc/Heptane gave the title compound (Compound B-2, 17.7 g, 93% yield).

$^1$H NMR (500 MHz, CHLOROFORM-d) δ ppm 0.17 (s, 9H) 1.02 (d, J=6.8 Hz, 3H) 2.10-2.18 (m, 1H) 2.44 (s, 3H) 3.82 (s, 3H) 3.99 (d, J=6.8 Hz, 1H) 4.04-4.07 (m, 2H) 4.33 (d, J=11.2 Hz, 1H) 4.66 (d, J=11.2 Hz, 1H) 6.87 (d, J=8.3 Hz, 2H) 7.21 (d, J=8.3 Hz, 2H) 7.33 (d, J=8.8 Hz, 2H) 7.77 (d, J=8.8 Hz, 2H).

Example 9

((3S,4R)-5-iodo-3-((4-methoxybenzyl)oxy)-4-methylpent-1-yn-1-yl)trimethylsilane (Compound B-3)

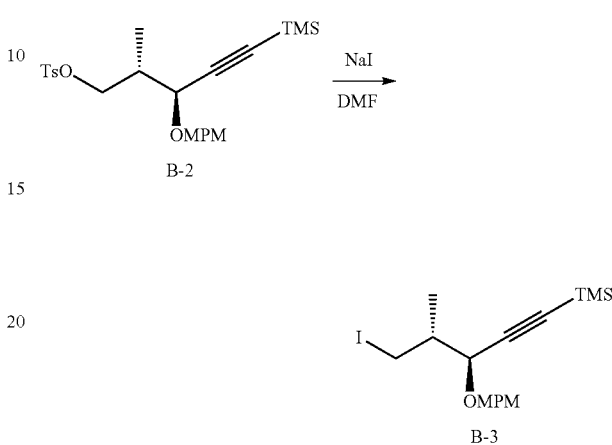

Under a nitrogen atmosphere, to the solution of Compound B-2: (2S,3 S)-3-((4-methoxybenzyl)oxy)-2-methyl-5-(trimethylsilyl)pent-4-yn-1-yl 4-methylbenzenesulfonate (17.7 g, 38.4 mmol) described in Example 8 in DMF (360 mL), NaI (7.49 g, 50.0 mmol) was added at room temperature. The reaction mixture was stirred at 80° C. for 2 hr. Another 2.0 g of NaI was added to the reaction mixture. The reaction was stirred for 1.5 hr at 80° C., then cooled to room temperature. The mixture was diluted with diethyl ether, washed with water and brine, dried over MgSO$_4$, filtered and concentrated under reduced pressure. Flash chromatography of the residue on silica gel (Silica Gel 60, spherical, 40-50 μm, Kanto Chemical) using 10% to 20% EtOAc/Heptane gave the title compound (Compound B-3, 14.3 g, 89% yield).

$^1$H NMR (500 MHz, CHLOROFORM-d) δ ppm 0.21 (s, 9H) 1.10 (d, J=6.8 Hz, 3H) 1.74-1.84 (m, 1H) 3.30-3.37 (m, 2H) 3.82 (s, 3H) 3.96 (d, J=7.3 Hz, 1H) 4.44 (d, J=11.2 Hz, 1H) 4.73 (d, J=11.2 Hz, 1H) 6.89 (d, J=8.8 Hz, 2H) 7.30 (d, J=8.8 Hz, 2H).

Scheme C; Preparation Compound C-8

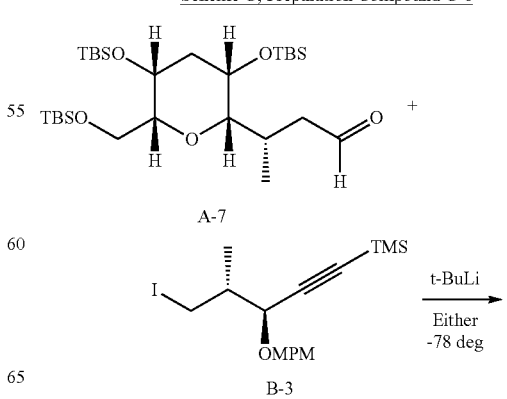

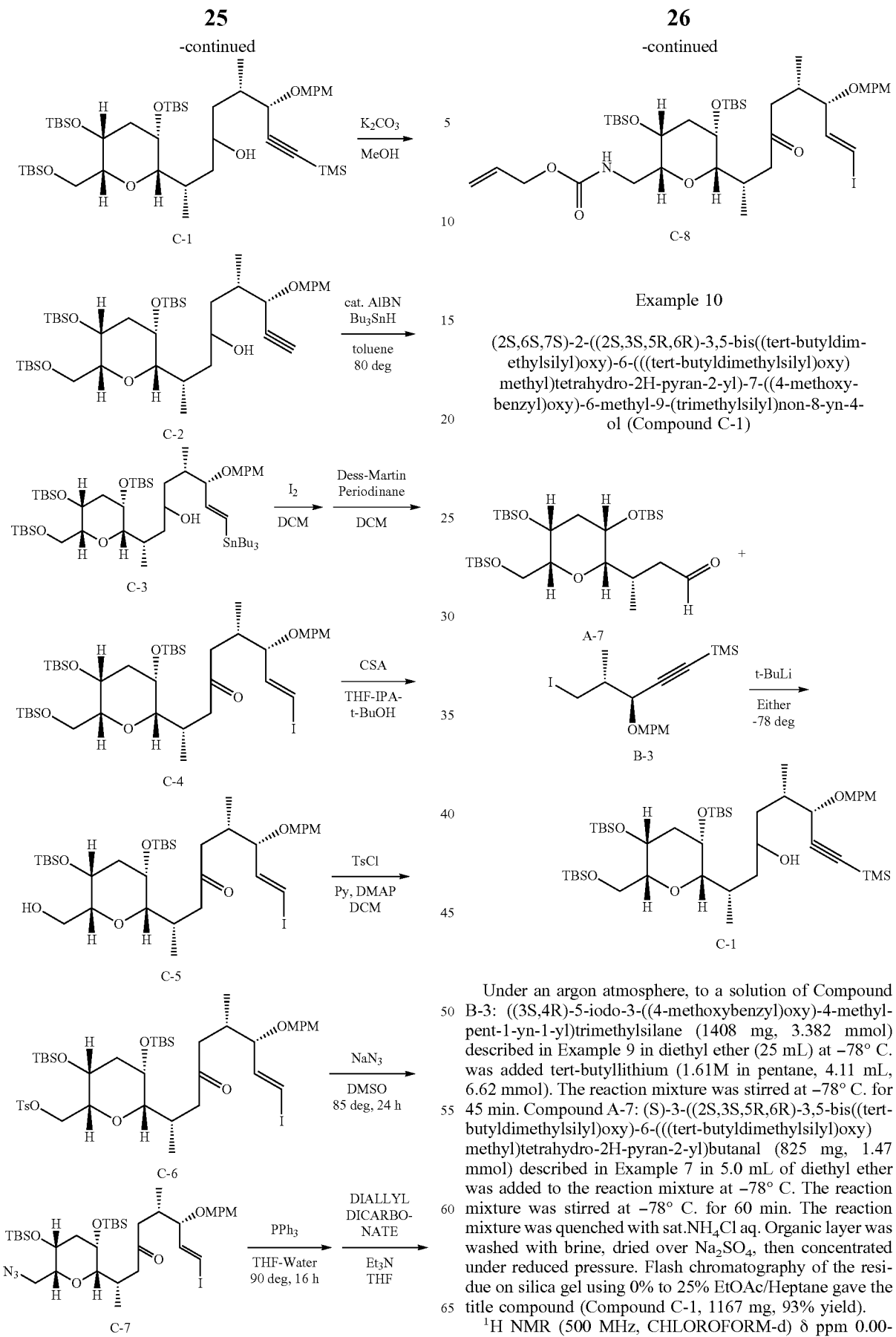

Example 10

(2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methyl-9-(trimethylsilyl)non-8-yn-4-ol (Compound C-1)

Under an argon atmosphere, to a solution of Compound B-3: ((3S,4R)-5-iodo-3-((4-methoxybenzyl)oxy)-4-methylpent-1-yn-1-yl)trimethylsilane (1408 mg, 3.382 mmol) described in Example 9 in diethyl ether (25 mL) at −78° C. was added tert-butyllithium (1.61M in pentane, 4.11 mL, 6.62 mmol). The reaction mixture was stirred at −78° C. for 45 min. Compound A-7: (S)-3-((2S,3S,5R,6R)-3,5-bis((tert-butyldimethylsilyl)oxy)-6-(((tert-butyldimethylsilyl)oxy)methyl)tetrahydro-2H-pyran-2-yl)butanal (825 mg, 1.47 mmol) described in Example 7 in 5.0 mL of diethyl ether was added to the reaction mixture at −78° C. The reaction mixture was stirred at −78° C. for 60 min. The reaction mixture was quenched with sat.NH$_4$Cl aq. Organic layer was washed with brine, dried over Na$_2$SO$_4$, then concentrated under reduced pressure. Flash chromatography of the residue on silica gel using 0% to 25% EtOAc/Heptane gave the title compound (Compound C-1, 1167 mg, 93% yield).

$^1$H NMR (500 MHz, CHLOROFORM-d) δ ppm 0.00-0.12 (m, 21H) 0.15-0.24 (m, 6H) 0.82-0.96 (m, 30H) 1.03 (d, J=6.3 Hz, 3H) 1.38-1.55 (m, 1H) 1.68-1.99 (m, 4H) 2.10-2.30 (m, 2H) 2.76-2.87 (m, 1H) 3.15 (d, J=9.75 Hz, 1H) 3.33-3.38 (m, 1H) 3.56-4.02 (m, 9H) 4.37-4.50 (m, 1H) 4.64-4.78 (m, 1H) 6.83-6.88 (m, 2H) 7.23-7.35 (m, 2H).

Example 11

(2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methyl-9-(tributylstannyl)non-8-en-4-ol (Compound C-3)

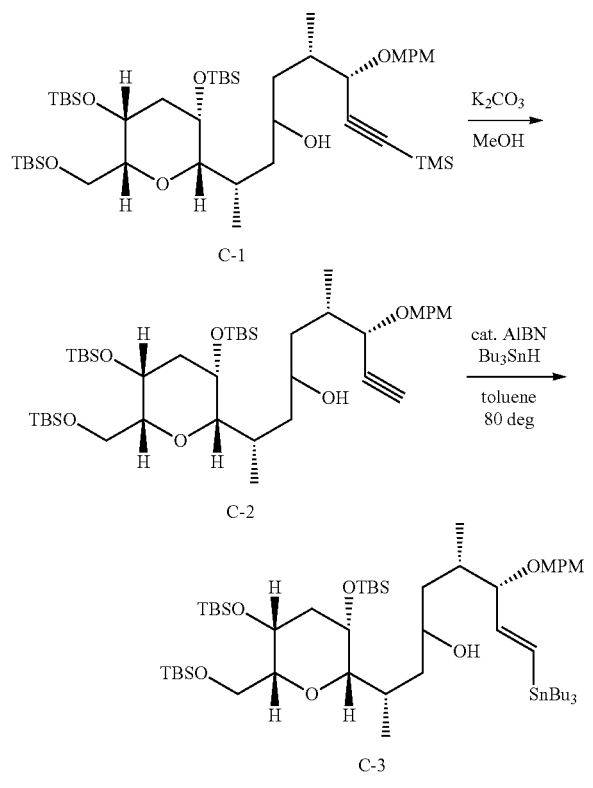

To a solution of Compound C-1: (2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methyl-9-(trimethylsilyl)non-8-yn-4-ol (1165 mg, 1.37 mmol) described in Example 10 in MeOH (20 mL) at 20° C. was added $K_2CO_3$ (189 mg, 1.37 mmol). The reaction mixture was stirred at 20° C. for 2 hr. The reaction mixture was diluted with EtOAc and quenched with sat.$NH_4Cl$ aq, then the layers were separated. The aqueous layer was extracted with EtOAc. The combined organic extracts were washed with brine, dried over $MgSO_4$, filtered and concentrated under reduced pressure. Flash chromatography of the residue on silica gel using 0% to 15% EtOAc/Heptane gave Compound C-2: (2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methylnon-8-yn-4-ol (1050 mg, 98% yield). ESI-MS (m/z): 801.50 [M+Na]$^+$ Under a nitrogen atmosphere, to a solution of Compound C-2: (2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methylnon-8-yn-4-ol (780 mg, 1.00 mmol) obtained above in toluene (15 mL) at 20° C. were added tri-n-butyltin hydride (2.5 mL, 9.36 mmol) and 2,2'-azobis(isobutyronitrile) (82 mg, 0.50 mmol). The reaction mixture was stirred at 90° C. for 15 min. The reaction mixture was concentrated under reduced pressure. Flash chromatography of the residue on silica gel using 0% to 15% EtOAc/Heptane gave the title compound (Compound C-3, 970 mg, 91% yield).

$^1$H NMR (500 MHz, CHLOROFORM-d) δ ppm 0.02-0.13 (m, 18H) 0.84-0.96 (m, 48H) 1.22-1.37 (m, 6H) 1.47-1.56 (m, 7H) 1.72-1.90 (m, 3H) 1.95-2.03 (m, 1H) 2.11-2.28 (m, 2H) 2.82-2.86 (m, 1H) 3.08-3.15 (m, 1H) 3.33-3.40 (m, 1H) 3.43-3.53 (m, 1H) 3.58-3.87 (m, 8H) 4.25-4.31 (m, 1H) 4.49-4.54 (m, 1H) 5.83 (dd, J=19.3, 7.6 Hz, 1H) 6.05-6.13 (m, 1H) 6.83-6.90 (m, 2H) 7.24 (d, J=8.8 Hz, 2H).

Example 12

(2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-one (Compound C-4)

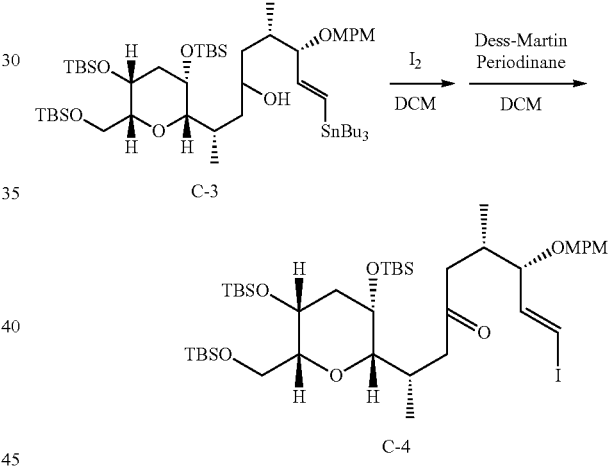

Under a nitrogen atmosphere, to a solution of Compound C-3: (2S,6S,7S)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-7-((4-methoxybenzyl)oxy)-6-methyl-9-(tributylstannyl)non-8-en-4-ol (970 mg, 0.91 mmol) described in Example 11 in 30 mL of DCM at 5° C. was added iodine (242 mg, 0.95 mmol) in DCM (6 mL) until it maintained the iodine color. The reaction mixture was quenched with sat.$Na_2SO_3$ aq and the layers were separated. The aqueous layer was extracted with DCM. The combined organic extracts were washed with brine. The combined organic layers were dried over $Na_2SO_4$, filtered and concentrated under reduced pressure. Flash chromatography of the residue on silica gel using 0% to 25% EtOAc/Heptane gave (2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-ol (768 mg, 93% yield).

Under a nitrogen atmosphere, to a solution of (2S,6S,7S,E)-2-((2S,3S,5R,6R)-3,5-bis((tert-butyldimethylsilyl)oxy)-6-(((tert-butyldimethylsilyl)oxy)methyl)tetrahydro-2H- pyran-2-yl)-9-iodo-7-((4-methoxybenzyl)oxy)-6-methylnon-8-en-4-ol (768 mg, 0.85 mmol) obtained above in DCM (25 mL) at room temperature was added NaHCO$_3$ (17.8 mg, 0.21 mmol) and Dess-Martin periodinane (485 mg, 1.14 mmol). The reaction mixture was stirred at room temperature for 4 hr. The reaction mixture was diluted with DCM and quenched with sat.NaHCO$_3$ aq and sat.Na$_2$SO$_3$ aq, and then the layers were separated. The aqueous layer was extracted with DCM. The combined organic extracts were washed with brine, dried over MgSO$_4$, filtered and concentrated under reduced pressure. Flash chromatography of the residue on silica gel using 0% to 20% EtOAc/Heptane gave the title compound (Compound C-4, 776 mg, Quant. yield).

$^1$H NMR (500 MHz, CHLOROFORM-d) δ ppm 0.00 (s, 3H) 0.03-0.07 (m, 12H) 0.10 (s, 3H) 0.81 (d, J=6.3 Hz, 3H) 0.84 (d, J=6.3 Hz, 3H) 0.89 (s, 9H) 0.91 (s, 9H) 0.92 (s, 9H) 1.80 (dt, J=15.0, 4.5 Hz, 1H) 1.99 (dt, J=15.0, 2.5 Hz, 1H) 2.17 (dd, J=16.6, 10.2 Hz, 1H) 2.20-2.29 (m, 2H) 2.43-2.48 (m, 1H) 2.54 (d, J=12.7 Hz, 1H) 2.87 (dd, J=9.0, 1.7 Hz, 1H) 2.99 (dd, J=16.6, 2.9 Hz, 1H) 3.27 (td, J=5.8, 2.4 Hz, 1H) 3.50-3.56 (m, 1H) 3.66-3.74 (m, 2H) 3.75-3.78 (m, 1H) 3.80 (s, 3H) 3.81-3.85 (m, 1H) 4.26 (d, J=11.7 Hz, 1H) 4.50 (d, J=11.7 Hz, 1H) 6.26 (d, J=14.6 Hz, 1H) 6.42 (dd, J=14.6, 7.8 Hz, 1H) 6.87 (d, J=8.3 Hz, 2H) 7.21 (d, J=8.3 Hz, 2H). ESI-MS (m/z): 927.39 [M+Na]$^+$ Example 13

(2S,6S,7S,E)-2-((2S,3S,5R,6R)-3,5-bis((tert-butyldimethylsilyl)oxy)-6-(hydroxymethyl)tetrahydro-2H-pyran-2-yl)-9-iodo-7-((4-methoxybenzyl)oxy)-6-methylnon-8-en-4-one (Compound C-5)

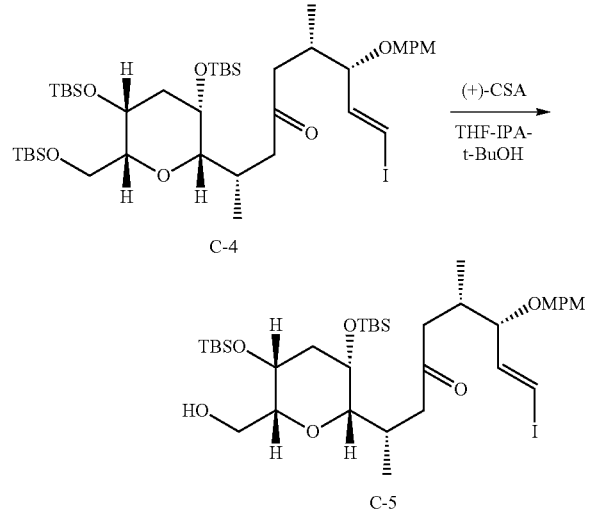

To a solution of Compound C-4: (2S,6S,7S,E)-2-((2S,3S,5R,6R)-3,5-bis((tert-butyldimethylsilyl)oxy)-6-(((tert-butyldimethylsilyl)oxy)methyl)tetrahydro-2H-pyran-2-yl)-9-iodo-7-((4-methoxybenzyl)oxy)-6-methylnon-8-en-4-one (600 mg, 0.66 mmol) described in Example 12 in THF (5.0 mL), IPA (5.0 mL) and t-BuOH (5.0 mL) at 4° C. was added (1S)-(+)-10-Camphorsulfonic acid (154 mg, 0.66 mmol). The reaction mixture was stirred at 4° C. for 20 hr. The reaction mixture was diluted with EtOAc and quenched with sat.NaHCO$_3$ aq, then the layers were separated. The aqueous layer was extracted with EtOAc. The combined organic extracts were washed with brine, dried over MgSO$_4$, filtered and concentrated under reduced pressure. Flash chromatography of the residue on silica gel using 0% to 35% EtOAc/Heptane gave the title compound (Compound C-5, 500 mg, 95% yield).

$^1$H NMR (500 MHz, CHLOROFORM-d) δ ppm 0.01 (s, 3H) 0.04 (s, 3H) 0.07 (s, 3H) 0.11 (s, 3H) 0.86-0.91 (m, 15H) 0.93 (s, 9H) 1.83 (dt, J=14.9, 4.8 Hz, 1H) 1.93-2.00 (dt, J=14.9, 4.8 Hz, 1H) 2.19-2.26 (m, 1H) 2.29 (dd, J=14.9, 5.6 Hz, 1H) 2.39 (dd, J=16.6, 8.3 Hz, 1H) 2.44-2.66 (m, 4H) 2.91 (dd, J=9.5, 1.7 Hz, 1H) 3.36-3.41 (m, 1H) 3.48 (td, J=11.3, 2.7 Hz, 1H) 3.59 (t, J=7.1 Hz, 1H) 3.74-3.78 (m, 2H) 3.80 (s, 3H) 3.85 (m, 1H) 4.25 (d, J=11.2 Hz, 1H) 4.46 (d, J=11.2 Hz, 1H) 6.28 (d, J=14.6 Hz, 1H) 6.43 (dd, J=14.6, 7.8 Hz, 1H) 6.87 (d, J=8.8 Hz, 2H) 7.21 (d, J=8.8 Hz, 2H). ESI-MS (m/z): 813.30 [M+Na]$^+$ Example 14

((2R,3R,5S,6S)-3,5-bis((tert-butyldimethylsilyl)oxy)-6-((2S,6S,7S,E)-9-iodo-7-((4-methoxybenzyl)oxy)-6-methyl-4-oxonon-8-en-2-yl)tetrahydro-2H-pyran-2-yl)methyl 4-methylbenzenesulfonate (Compound C-6)

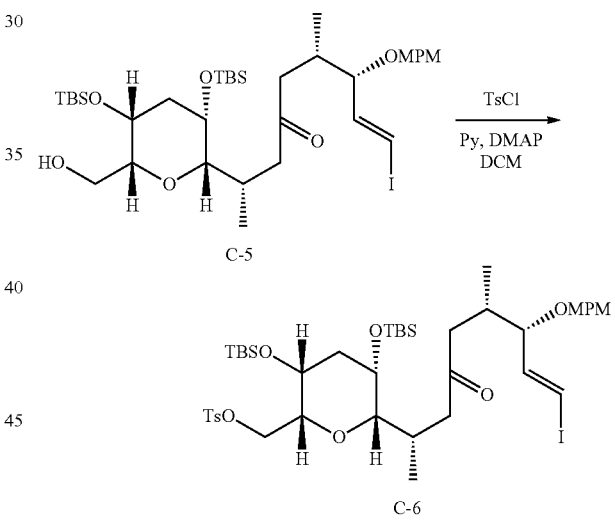

Under a nitrogen atmosphere, to a solution of Compound C-5: (2S,6S,7S,E)-2-((2S,3S,5R,6R)-3,5-bis((tert-butyldimethylsilyl)oxy)-6-(hydroxymethyl)tetrahydro-2H-pyran-2-yl)-9-iodo-7-((4-methoxybenzyl)oxy)-6-methylnon-8-en-4-one (500 mg, 0.63 mmol) described in Example 13 in DCM (10 mL) at 5° C. were added pyridine (2.54 mL, 31.6 mmol), p-toluenesulfonyl chloride (723 mg, 3.79 mmol) and 4-dimethylaminopyridine (77 mg, 0.63 mmol). The reaction mixture was stirred at room temperature for 24 hr. p-Toluenesulfonyl chloride (150 mg, 0.79 mmol) was added to the reaction mixture at room temperature. Then, the reaction mixture was stirred at room temperature for 8 hr. The reaction mixture was diluted with DCM and quenched with sat.NaHCO$_3$ aq, then the layers were separated. The aqueous layer was extracted with DCM. The combined organic extracts were washed with brine, dried over Na$_2$SO$_4$, filtered and concentrated under reduced pressure. Flash chromatography of the residue on silica gel using 0% to 25% EtOAc/Heptane gave the title compound (Compound C-6, 560 mg, 94% yield).

$^1$H NMR (500 MHz, CHLOROFORM-d) δ ppm 0.01 (s, 3H) 0.04 (s, 3H) 0.04 (s, 3H) 0.08 (s, 3H) 0.81 (d, J=6.8 Hz, 3H) 0.83 (s, 9H) 0.86 (d, J=6.8 Hz, 3H) 0.89 (s, 9H) 1.81 (dt, J=14.9, 4.5 Hz, 1H) 1.91-1.96 (m, 1H) 2.15-2.32 (m, 3H) 2.36-2.42 (m, 1H) 2.43 (s, 3H) 2.57 (d, J=12.7 Hz, 1H) 2.77 (dd, J=16.6, 3.4 Hz, 1H) 2.87 (dd, J=9.0, 1.7 Hz, 1H) 3.53-3.58 (m, 2H) 3.70-3.75 (m, 1H) 3.80-3.85 (m, 1H) 3.81 (s, 3H) 4.06 (dd, J=10.0, 5.0 Hz, 1H) 4.08-4.16 (m, 1H) 4.28 (d, J=11.2 Hz, 1H) 4.51 (d, J=11.2 Hz, 1H) 6.30 (d, J=14.6 Hz, 1H) 6.45 (dd, J=14.6, 7.8 Hz, 1H) 6.88 (d, J=8.8 Hz, 2H) 7.24 (d, J=8.8 Hz, 2H) 7.31 (d, J=8.3 Hz, 2H) 7.76 (d, J=8.3 Hz, 2H).

Example 15

(2S,6S,7S,E)-2-((2S,3S,5R,6R)-6-(azidomethyl)-3,5-bis((tert-butyldimethylsilyl)oxy)tetrahydro-2H-pyran-2-yl)-9-iodo-7-((4-methoxybenzyl)oxy)-6-methylnon-8-en-4-one (Compound C-7)

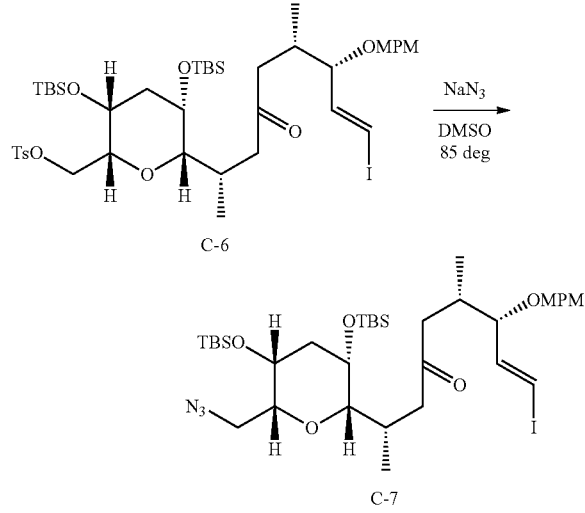

Under a nitrogen atmosphere, to a solution of Compound C-6: ((2R,3R,5S,6S)-3,5-bis((tert-butyldimethylsilyl)oxy)-6-((2S,6S,7S,E)-9-iodo-7-((4-methoxybenzyl)oxy)-6-methyl-4-oxonon-8-en-2-yl)tetrahydro-2H-pyran-2-yl) methyl 4-methylbenzenesulfonate (560 mg, 0.59 mmol) described in Example 14 in DMSO (5.6 mL) at 20° C. was added sodium azide (385 mg, 5.92 mmol). The reaction mixture was stirred at 85° C. After 2 hr, sodium azide (100 mg, 1.54 mmol) was added to the reaction mixture, then the reaction mixture was stirred at 85° C. for 14 hr. The reaction mixture was diluted with EtOAc and quenched with H$_2$O, then the layers were separated. The organic extracts were successively washed with water and brine. The combined organic layers were dried over Na$_2$SO$_4$, filtered and concentrated under reduced pressure to give a crude residue. Flash chromatography of the residue on silica gel using 0% to 15% EtOAc/Heptane gave the title compound (Compound C-7, 298 mg, 62% yield).

$^1$H NMR (500 MHz, CHLOROFORM-d) δ ppm 0.03 (s, 3H) 0.06 (s, 3H) 0.07 (s, 3H) 0.10 (s, 3H) 0.84 (d, J=6.8 Hz, 3H) 0.85 (d, J=6.8 Hz, 3H) 0.91 (s, 9H) 0.92 (s, 9H) 1.86 (dt, J=15.0, 4.7 Hz, 1H) 1.98 (dt, J=15.0, 2.9 Hz, 1H) 2.19-2.32 (m, 3H) 2.41-2.49 (m, 1H) 2.58 (d, J=12.7 Hz, 1H) 2.94 (dd, J=16.6, 2.9 Hz, 1H) 2.98 (dd, J=8.8, 2.0 Hz, 1H) 3.02 (dd, J=12.7, 2.9 Hz, 1H) 3.47 (dt, J=8.8, 2.7 Hz, 1H) 3.49-3.54 (m, 1H) 3.63 (dd, J=12.7, 8.8 Hz, 1H) 3.69-3.73 (m, 1H) 3.81 (s, 3H) 3.83-3.88 (m, 1H) 4.26 (d, J=11.7 Hz, 1H) 4.50 (d, J=11.7 Hz, 1H) 6.26 (d, J=14.6 Hz, 1H) 6.42 (dd, J=14.6, 7.8 Hz, 1H) 6.87 (d, J=8.8 Hz, 2H) 7.22 (d, J=8.8 Hz, 2H).

Example 16

(((2R,3R,5S,6S)-3,5-bis((tert-butyldimethylsilyl)oxy)-6-((2S,6S,7S,E)-9-iodo-7-((4-methoxybenzyl)oxy)-6-methyl-4-oxonon-8-en-2-yl)tetrahydro-2H-pyran-2-yl)methyl)carbamate (Compound C-8)

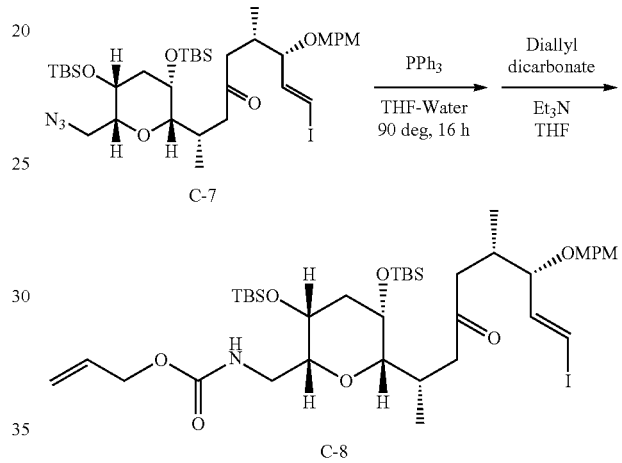

To a solution of Compound C-7: (2S,6S,7S,E)-2-((2S,3S,5R,6R)-6-(azidomethyl)-3,5-bis((tert-butyldimethylsilyl)oxy)tetrahydro-2H-pyran-2-yl)-9-iodo-7-((4-methoxybenzyl)oxy)-6-methylnon-8-en-4-one (298 mg, 0.37 mmol) described in Example 15 in THF (10 mL) and water (1.0 mL) at 20° C. was added triphenylphosphine (1437 mg, 5.478 mmol). The reaction mixture was stirred at 70° C. for 1.5 hr. The reaction mixture was concentrated under reduced pressure to give a crude amine. To a solution of the crude amine obtained above in THF (10 mL) at 5° C. were added Et$_3$N (0.51 mL, 3.66 mmol) and diallyl dicarbonate (341 mg, 1.83 mmol). The reaction mixture was stirred at room temperature for 60 min. The reaction mixture was concentrated under reduced pressure. Flash chromatography of the residue on silica gel using 0% to 25% EtOAc/Heptane gave the title compound (Compound C-8, 300 mg, 94% yield).

$^1$H NMR (500 MHz, CHLOROFORM-d) δ ppm 0.05-0.07 (m, 9H) 0.11 (s, 3H) 0.85 (d, J=6.3 Hz, 3H) 0.87 (d, J=6.3 Hz, 3H) 0.90 (s, 9H) 0.93 (s, 9H) 1.80 (dt, J=15.0, 4.4 Hz, 1H) 1.96 (dt, J=15.0, 2.8 Hz, 1H) 2.16-2.29 (m, 2H) 2.32-2.39 (m, 1H) 2.53-2.60 (m, 3H) 2.86 (d, J=7.3 Hz, 1H) 3.04-3.11 (m, 1H) 3.30-3.34 (m, 1H) 3.38-3.48 (m, 1H) 3.58 (t, J=7.1 Hz, 1H) 3.70-3.76 (m, 1H) 3.80 (s, 3H) 3.81-3.84 (m, 1H) 4.25 (d, J=11.2 Hz, 1H) 4.46 (d, J=11.2 Hz, 1H) 4.53-4.63 (m, 2H) 5.19 (dd, J=10.7, 1.5 Hz, 1H) 5.32 (d, J=17.1 Hz, 1H) 5.47 (d, J=6.8 Hz, 1H) 5.88-5.99 (m, 1H) 6.28 (d, J=14.6 Hz, 1H) 6.43 (dd, J=14.6, 7.8 Hz, 1H) 6.87 (d, J=8.8 Hz, 2H) 7.21 (d, J=8.8 Hz, 2H). ESI-MS (m/z): 896.34 [M+Na]$^+$ Scheme D; Preparation Compound D-7
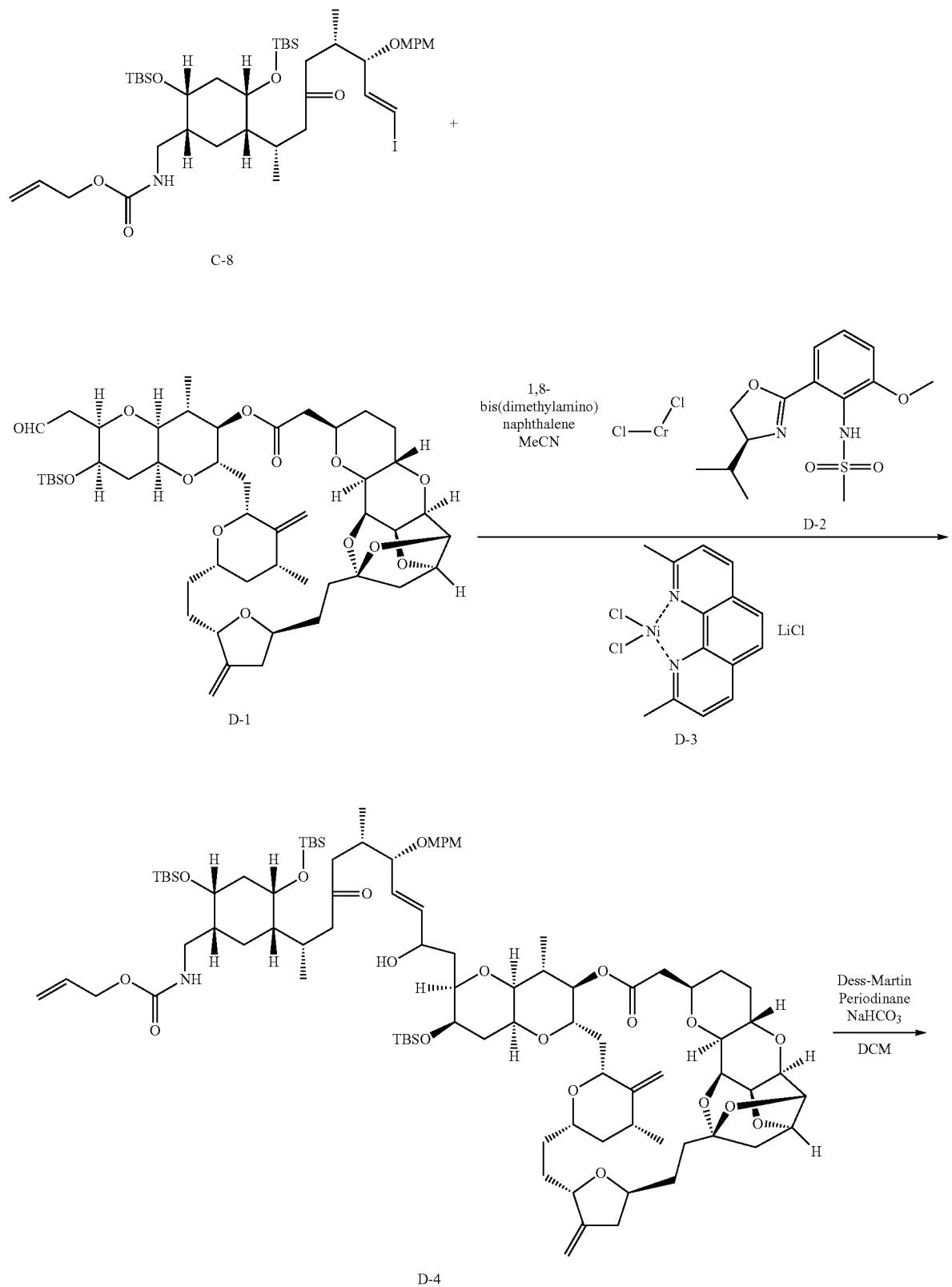

-continued
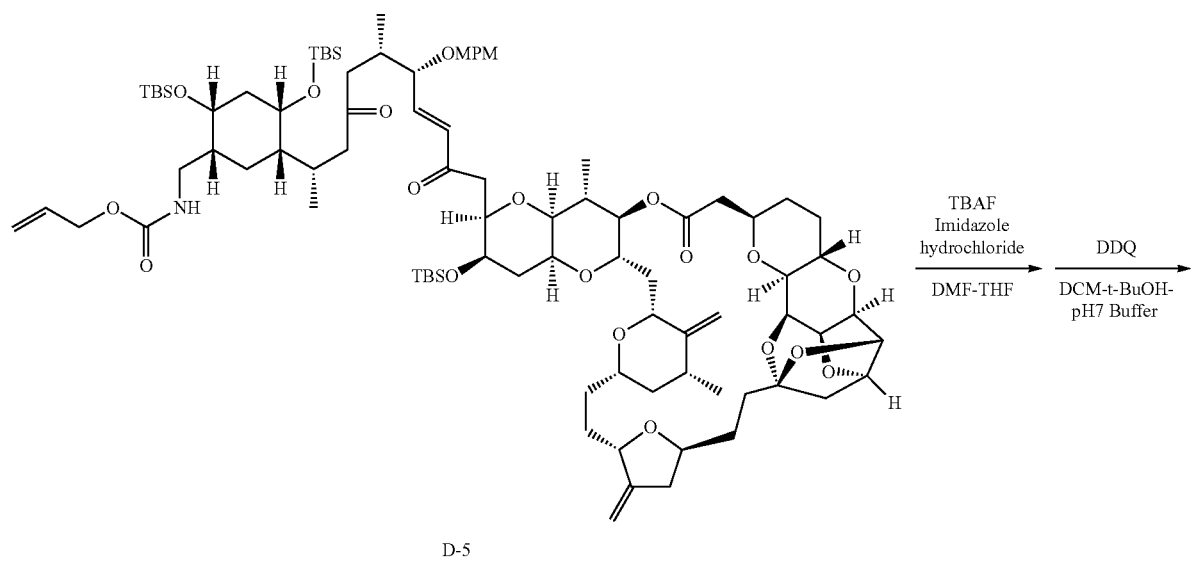
D-5
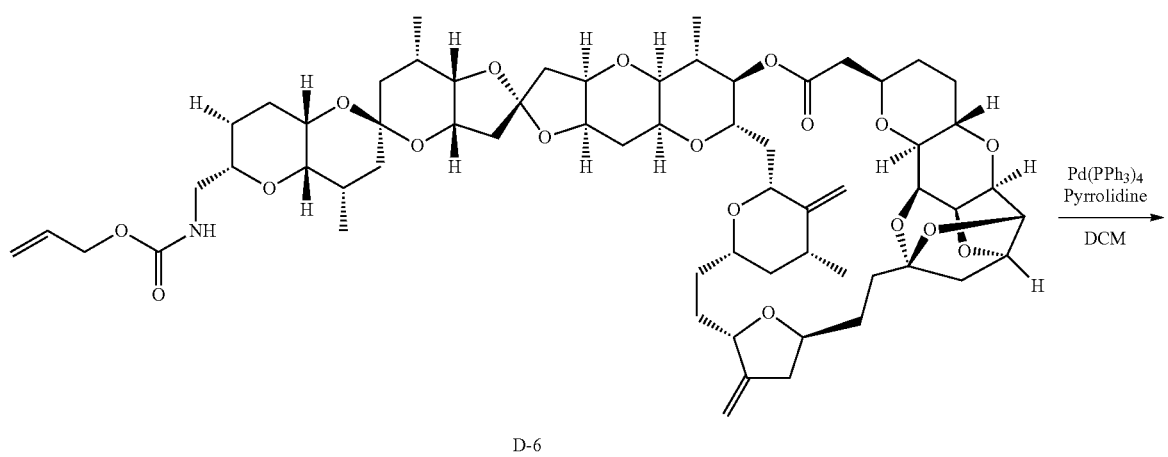
D-6
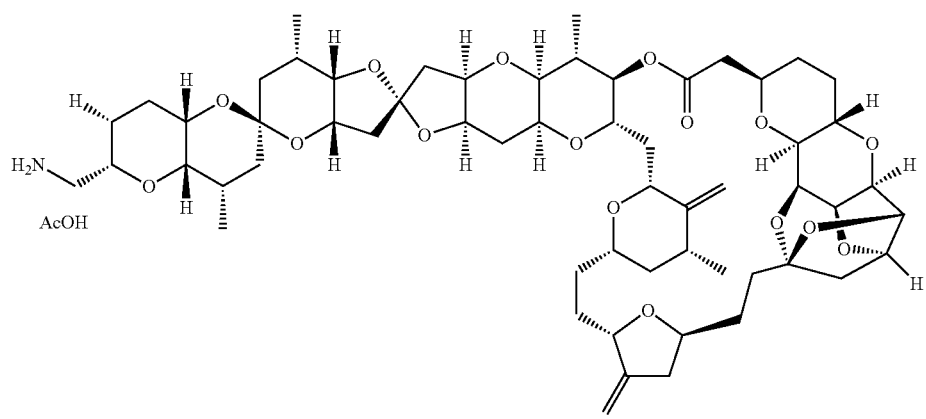
D-7

Example 17

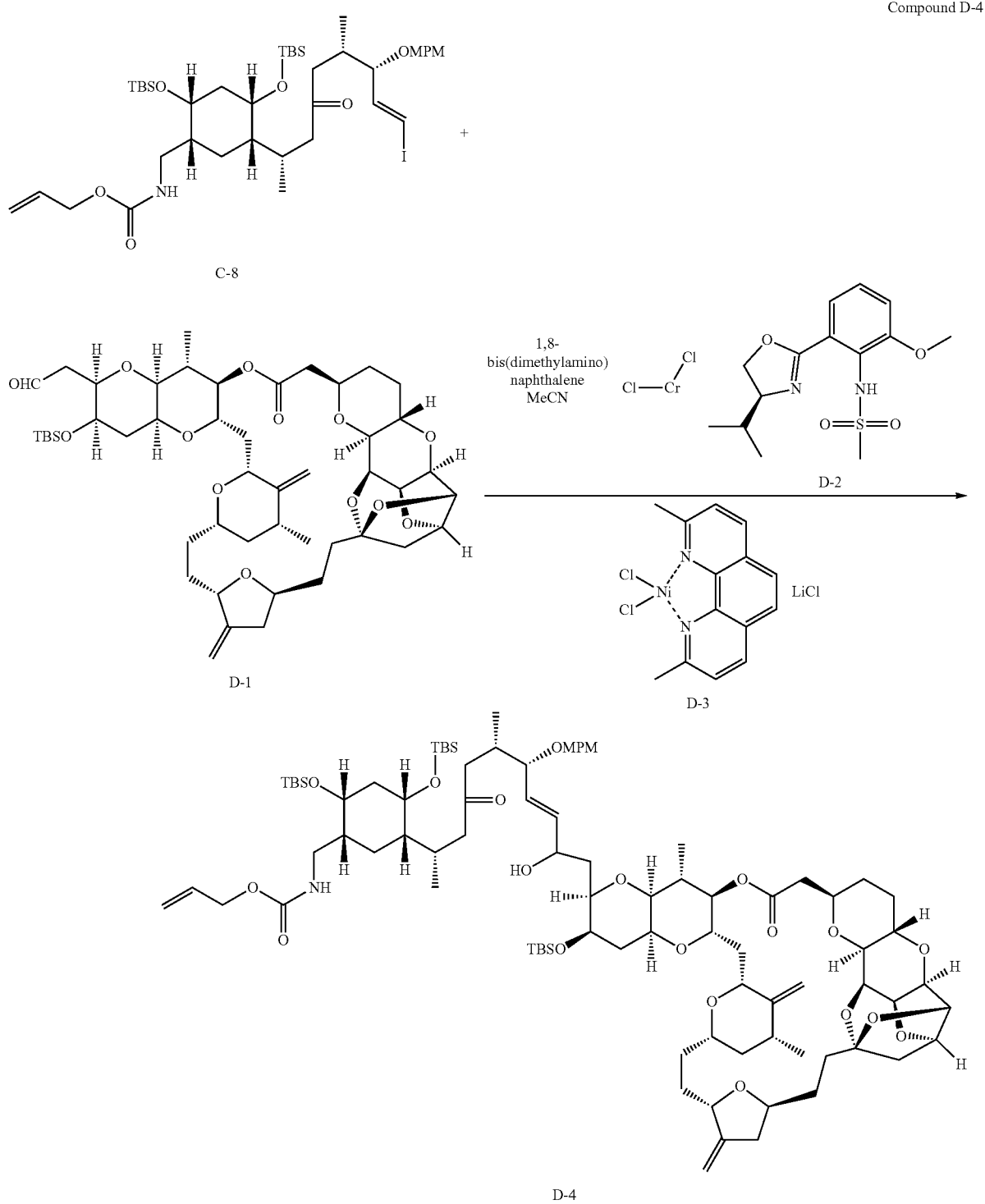

Under a nitrogen atmosphere (in a glove box), to a solution of Compound D-2: (S)—N-(2-(4-isopropyl-4,5-dihydrooxazol-2-yl)-6-methoxyphenyl)methanesulfonamide (155 mg, 0.497 mmol) obtained by the method written in Organic Letters (2002), 4 (25), 4431-4434 (CAS No; 546141-34-8) and 1,8-bis(dimethylamino)naphthalene (107 mg, 0.497 mmol) in MeCN (0.75 mL) was added chromium (II) chloride (55.5 mg, 0.452 mmol) and then the resulting mixture was stirred in the glove box at room temperature for 1 hr. The resulting green solution was added to a mixture of Compound C-8: allyl (((2R,3R,5S,6S)-3,5-bis((tert-butyldimethylsilyl)oxy)-6-((2S,6S,7S,E)-9-iodo-7-((4- methoxy benzyl)oxy)-6-methyl-4-oxonon-8-en-2-yl)tetrahydro-2H-pyran-2-yl)methyl)carbamate (99.0 mg, 0.113 mmol) described in Example 16, Compound D-1(80.0 mg, 0.09 mmol) obtained by the method written in *Journal of the American Chemical Society* (1992), 114 (8), 3162-3164 (CAS No; 157322-23-1), Compound D-3: dichloro(2,9-dimethyl-1,10-phenanthroline)nickel (0.46 mg, 1.36 μmol) obtained by the method written in *Journal of the American Chemical Society* (2009), 131(42), 15387-15393 (CAS No; 21361-04-6) and lithium chloride (3.83 mg, 0.09 mmol). The reaction mixture was stirred in the glove box at room temperature for 60 min. The reaction mixture was then taken out of the glove box, diluted with diethyl ether-EtOAc (5.0 mL-5.0 mL), then Florisil® (1600 mg, 15.94 mmol) (CAS No; 1343-88-0) was added to the mixture. Then mixture was stirred at room temperature for 30 min. The mixture was filtered (Celite®), washed with EtOAc/Heptane=2/1, then filtrate was concentrated under reduced pressure. Flash chromatography of the residue on silica gel using 3% to 55% EtOAc/Heptane gave the title compound (Compound D-4, 140 mg, 95% yield).

Example 18

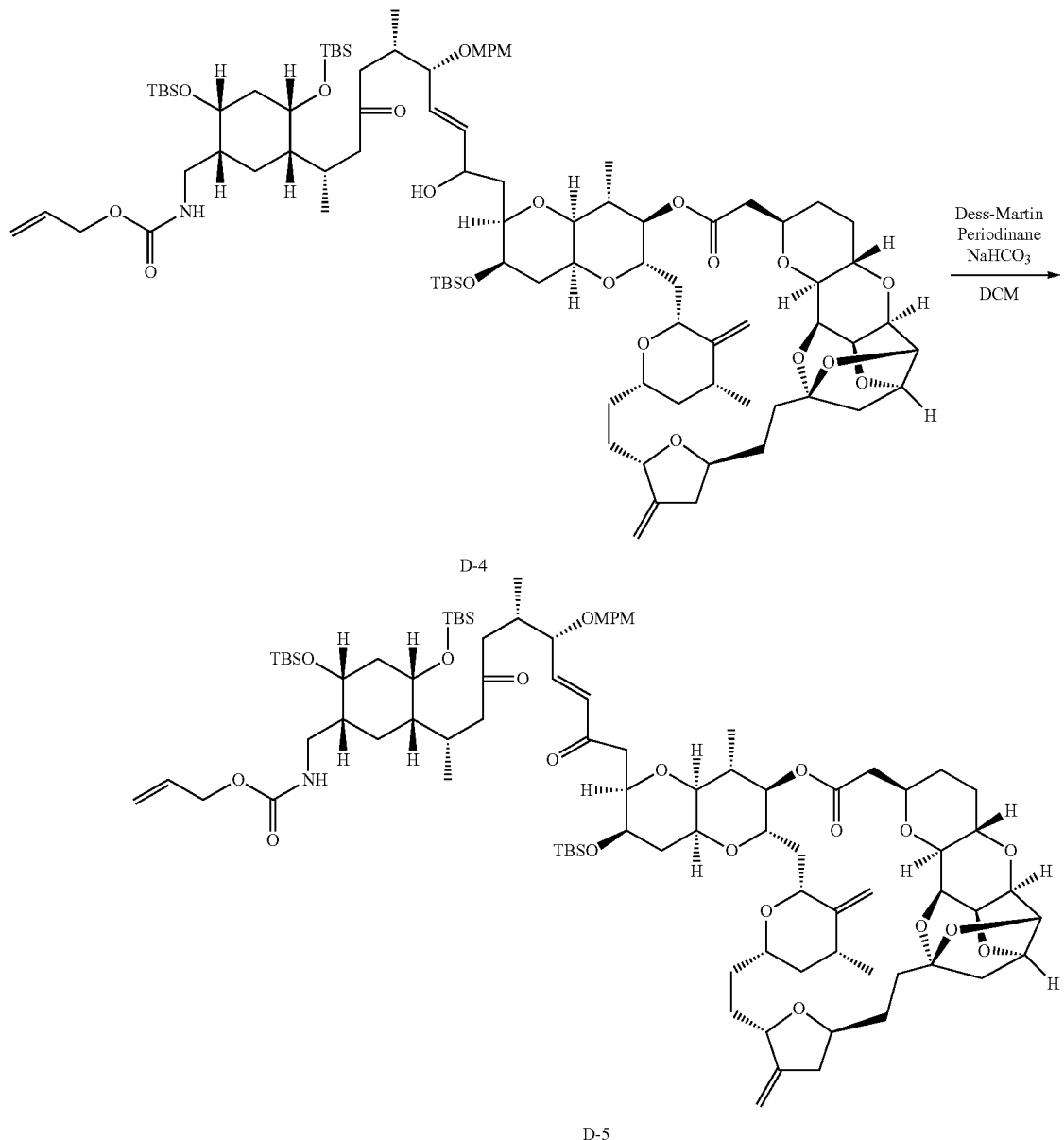

Under a nitrogen atmosphere, to a solution of Compound D-4 (140 mg, 0.09 mmol) described in Example 17 in DCM (5.0 mL) at 5° C. were added NaHCO₃ (28.8 mg, 0.34 mmol) and Dess-Martin periodinane (72.7 mg, 0.17 mmol). The reaction mixture was stirred at room temperature for 60 min. The reaction mixture was diluted with DCM and quenched with sat. NaHCO₃ aq and sat. Na₂SO₃ aq, and then the layers were separated. The aqueous layer was extracted with DCM. The combined organic extracts were washed with brine, dried over Na₂SO₄, filtered and concentrated under reduced pressure. Flash chromatography of the residue on silica gel using 2% to 60% EtOAc/Heptane gave the title compound (Compound D-5, 120 mg, 86%).

¹H NMR (500 MHz, BENZENE-d6) δ ppm 0.01-0.05 (m, 9H) 0.10-0.12 (m, 6H) 0.15 (s, 3H) 0.76 (d, J=6.1 Hz, 3H) 0.96 (s, 9H) 1.02 (s, 9H) 1.04 (s, 9H) 0.95-1.10 (m, 7H) 1.20 (d, J=7.3 Hz, 3H) 1.31-1.37 (m, 3H) 1.41 (dd, J=12.8, 4.9 Hz, 1H) 1.40-1.58 (m, 4H) 1.59-1.64 (m, 1H) 1.69-1.89 (m, 3H) 1.90-1.99 (m, 2H) 2.02-2.25 (m, 8H) 2.26-2.48 (m, 6H) 2.49-2.70 (m, 6H) 2.71-2.84 (m, 2H) 3.00-3.07 (m, 1H) 3.12-3.30 (m, 4H) 3.36 (s, 3H) 3.40 (br.s, 1H) 3.44-3.53 (m, 2H) 3.65 (dd, J=6.4, 4.0 Hz, 1H) 3.69-3.84 (m, 4H) 3.86-4.03 (m, 4H) 4.07-4.17 (m, 3H) 4.27-4.29 (m, 1H) 4.27 (d, J=11.0 Hz, 1H) 4.48-4.58 (m, 1H) 4.49 (d, J=11.0 Hz, 1H) 4.65-4.70 (m, 2H) 4.68 (d, J=5.5 Hz, 1H) 4.74-4.86 (m, 2H) 4.78 (s, 1H) 4.93 (s, 1H) 5.05 (d, J=10.4 Hz, 1H) 5.09 (br. s., 1H) 5.19 (br. s., 1H) 5.30 (dd, J=17.1, 1.2 Hz, 1H) 5.82 (d, J=8.0 Hz, 1H) 5.86-5.96 (m, 1H) 6.46 (d, J=15.9 Hz, 1H) 6.84-6.92 (m, 3H) 7.31 (d, J=8.6 Hz, 2H).

Example 19

Imidazole hydrochloride (155 mg, 1.48 mmol) was dissolved in DMF (2.9 mL) to give a 0.5 M imidazole hydrochloride solution in DMF. 1.0 mL of this solution was mixed with 1.0 mL of TBAF (1.0 M, THF solution) to give a premixed solution of 0.5 M TBAF and 0.25 M imidazole hydrochloride in THF-DMF (1:1). Under a nitrogen atmosphere, to a solution of Compound D-5 (80.0 mg, 0.05 mmol) described in Example 18 in DMF (7.0 mL) at 20° C. were added 0.588 mL of premixed solution of TBAF (0.5 M) and imidazole hydrochloride (0.25 M) in THF-DMF (1:1) prepared above. The reaction mixture was stirred at room temperature for 14 hr. 1.6 g of CaCO₃ and 4.0 g of Dowex® 50WX8 (hydrogen form, 200-400 mesh, SIGMA-ALDRICH) were added to the reaction mixture. The mixture was stirred at room temperature for 2 hr. Then mixture was diluted with EtOAc, then filtered (Celite®), washed with EtOAc. Filtrate was concentrated under reduced pressure to give a crude residue. 1000 mg of CaCO₃ and 2.25 g of Dowex® 50WX8 were added to the EtOAc (6.0 mL) solution of the crude residue. The mixture was stirred at room temperature for 2.5 hr. Then mixture was diluted with EtOAc, filtered (Celite®), washed with EtOAc. Filtrate was concentrated under reduced pressure to give a crude residue (63.0 mg). To a solution of the crude residue (63.0 mg)

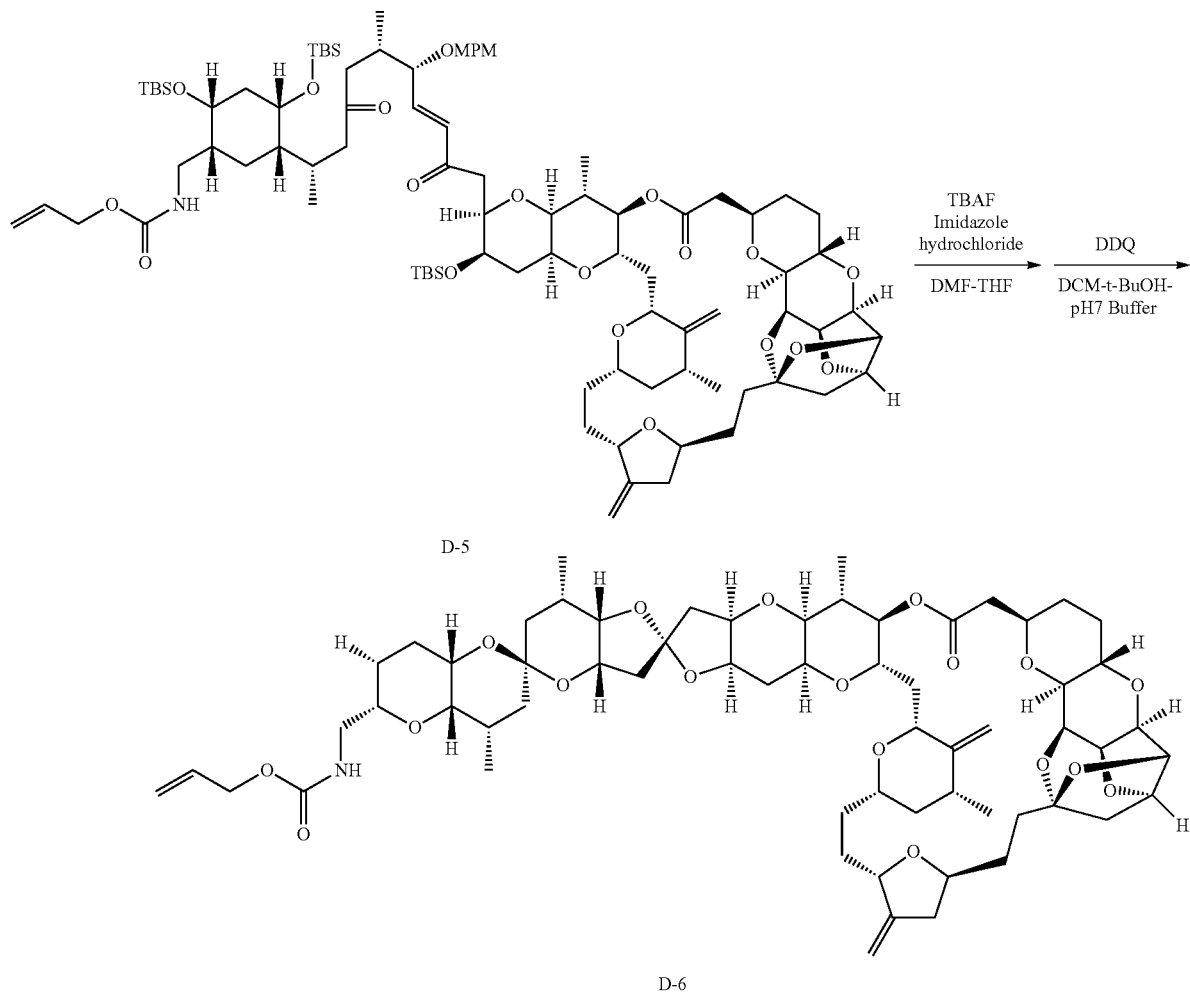

obtained above in DCM (6.0 mL), t-BuOH (0.6 mL) and pH 7 Phosphate Buffer (0.6 mL, 1/15 M) at room temperature was added DDQ (111 mg, 0.49 mmol). The reaction mixture was stirred at room temperature for 45 min. The reaction mixture was quenched with sat. NaHCO₃ aq, then diluted with DCM and the layers were separated. The aqueous layer was extracted with DCM (3 times). The combined organic extracts were dried over Na₂SO₄, filtered and concentrated under reduced pressure. Flash chromatography of the residue on NH silica gel using 10% to 100% EtOAc/Heptane, then 10% MeOH/EtOAc gave a roughly purified title compound (Compound D-6, 15.0 mg, 27%).

¹H NMR (500 MHz, METHANOL-d4) δ ppm 0.97 (d, J=7.0 Hz, 3H) 0.97 (d, J=7.0 Hz, 3H) 1.00-1.02 (m, 1H) 1.05 (d, J=7.3 Hz, 3H) 1.09 (d, J=6.3 Hz, 3H) 1.31-1.45 (m, 6H) 1.46-1.63 (m, 5H) 1.64-1.75 (m, 3H) 1.80-1.86 (m, 2H) 1.87-1.93 (m, 2H) 1.94-2.11 (m, 9H) 2.13-2.27 (m, 8H) 2.33 (d, J=2.4 Hz, 2H) 2.39 (dd, J=13.4, 6.1 Hz, 1H) 2.44 (dd, J=17.6, 2.0 Hz, 1H) 2.55 (dd, J=17.6, 9.3 Hz, 1H) 2.75-2.84 (m, 1H) 2.97 (dd, J=9.3, 2.0 Hz, 1H) 3.21 (dd, J=6.6, 4.6 Hz, 1H) 3.32 (m, 1H) 3.41-3.46 (m, 1H) 3.57 (br. s., 1H) 3.60 (d, J=11.7 Hz, 1H) 3.67-3.74 (m, 2H) 3.78 (br. s., 1H) 3.86-3.90 (m, 2H) 3.97 (d, J=2.4 Hz, 1H) 4.02-4.11 (m, 4H) 4.17 (dd, J=6.6, 4.6 Hz, 1H) 4.23 (dd, J=11.5, 2.2 Hz, 1H) 4.29 (br.s, 1H) 4.31 (td, J=9.3, 3.9 Hz, 1H) 4.44 (d, J=10.2 Hz, 1H) 4.51 (d, J=5.4 Hz, 2H) 4.59 (t, J=4.9 Hz, 1H) 4.61 (dd, J=7.3, 4.9 Hz, 1H) 4.69 (t, J=4.6 Hz, 1H) 4.80 (s, 1H) 4.85-4.87 (m, 1H) 5.01 (s, 1H) 5.05 (s, 1H) 5.16 (dd, J=10.7, 1.0 Hz, 1H) 5.28 (dd, J=17.1, 2.0 Hz, 1H) 5.92 (m, 1H). ESI-MS (m/z): 1172.57 [M+Na]⁺

Example 20

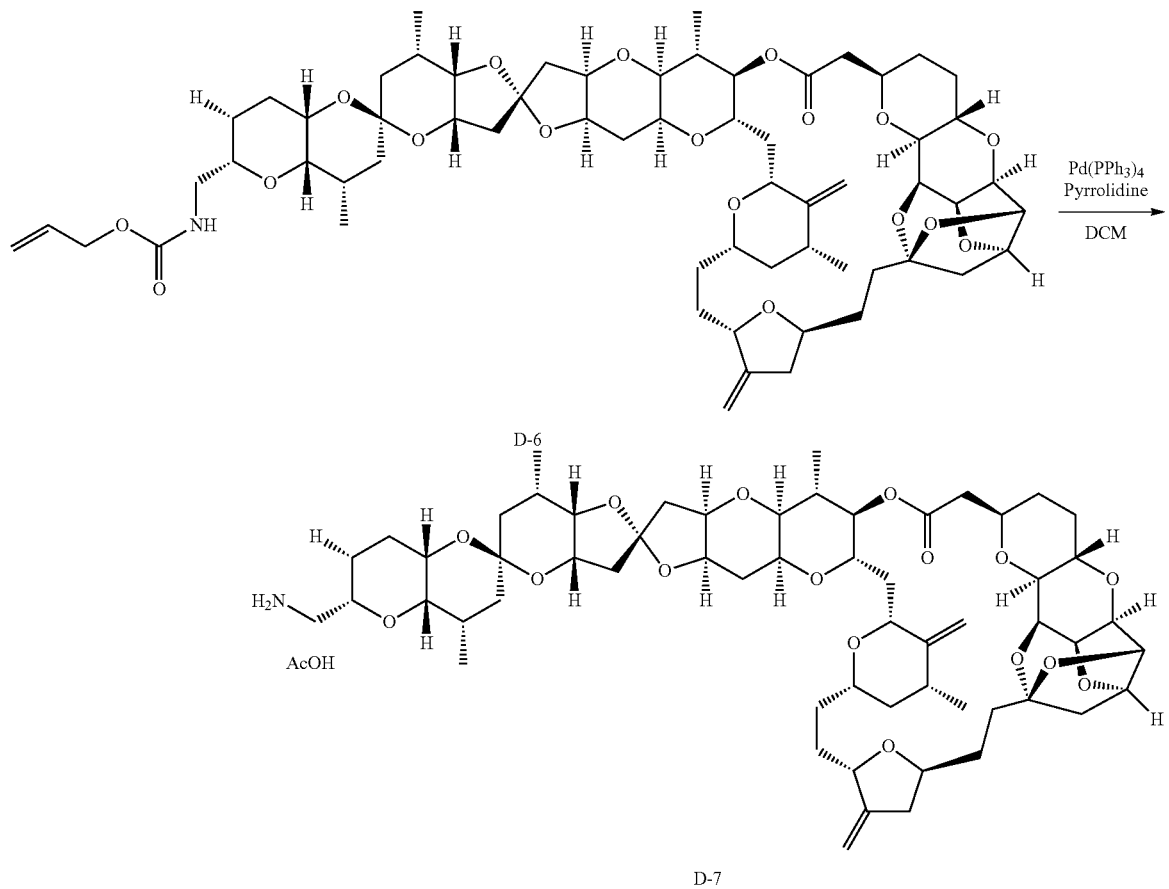

Compound D-7

Under a nitrogen atmosphere, to a solution of Compound D-6 (15.0 mg, 0.013 mmol) described in Example 19, pyrrolidine (10.8 μL, 0.13 mmol) in DCM (2.0 mL) at room temperature was added tetrakis(triphenylphosphine)palladium(0) (7.53 mg, 6.52 μmol). The reaction mixture was stirred at room temperature for 30 min. The reaction mixture was concentrated under reduced pressure. Flash chromatography of the residue on NH silica gel using 50% EtOAc/Heptane, then 0% to 20% MeOH/EtOAc to give a roughly purified product. Obtained roughly purified product was purified by HPLC to give the title compound (D-7, 7.0 mg, 47%, retention time=13.8 min).

HPLC conditions:
Column: YMC Pak Pro C18 (20 mm×250 mm)
Detection wavelength: 200 nm
Column temperature: room temperature
Mobile phase: MeCN-Water (0.05% AcOH)
Flow rate: 8 mL/min
Eluate:
MeCN/Water 25% (iso, 2 min), then
MeCN/Water 25% to 60% (Gradient, 20 min)

¹H NMR (500 MHz, METHANOL-d4) δ ppm 0.99 (d, J=6.7 Hz, 3H) 1.00-1.03 (m, 1H) 1.04 (d, J=7.3 Hz, 3H) 1.06

(d, J=7.3 Hz, 3H) 1.10 (d, J=6.1 Hz, 3H) 1.29-1.63 (m, 10H) 1.65-1.78 (m, 3H) 1.79-1.89 (m, 2H) 1.92-2.12 (m, 10H) 1.93 (s, 3H) 2.13-2.36 (m, 9H) 2.41 (dd, J=13.5, 6.1 Hz, 1H) 2.45 (dd, J=17.6, 2.2 Hz, 1H) 2.56 (dd, J=17.6, 9.8 Hz, 1H) 2.75-2.84 (m, 1H) 2.98 (dd, J=9.8, 1.8 Hz, 1H) 3.12 (dd, J=12.8, 3.7 Hz, 1H) 3.22 (dd, J=6.4, 4.6 Hz, 1H) 3.26 (dd, J=13.2, 7.8 Hz, 1H) 3.39 (d, J=1.8 Hz, 1H) 3.61 (d, J=12.8 Hz, 1H) 3.63-3.68 (m, 2H) 3.68-3.76 (m, 2H) 3.81-3.94 (m, 3H) 4.00 (d, J=2.5 Hz, 1H) 4.03-4.15 (m, 4H) 4.18 (dd, J=6.4, 4.6 Hz, 1H) 4.25 (ddd, J=11.0, 4.3, 1.8 Hz, 1H) 4.27-4.36 (m, 2H) 4.46 (d, J=11.0 Hz, 1H) 4.57-4.65 (m, 2H) 4.70 (t, J=4.6 Hz, 1H) 4.81 (d, J=1.2 Hz, 1H) 5.02 (br. s, 1H) 5.06 (d, J=1.8 Hz, 1H). ESI-MS (m/z): 1066.96 [M+H]$^+$, 1090.19 [M+Na]$^+$ Compound (1) (salt free form of Compound D-7): $^1$H NMR (600 MHz, METHANOL-d4) δ ppm 0.98 (d, J=7.2 Hz, 3H) 1.00 (d, J=6.8 Hz, 3H) 1.02 (m, 1H) 1.05 (d, J=6.8 Hz, 3H) 1.09 (d, J=6.4 Hz, 3H) 1.28-1.45 (m, 5H) 1.46-1.59 (m, 4H) 1.57-1.63 (m, 1H) 1.65-1.71 (m, 1H) 1.70-1.75 (m, 2H) 1.79-1.86 (m, 2H) 1.91 (dt, J=14.9, 3.1 Hz, 1H) 1.94-2.11 (m, 8H) 2.14-2.34 (m, 9H) 2.39 (dd, J=13.2, 6.0 Hz, 1H) 2.44 (dd, J=17.4, 1.9 Hz, 1H) 2.56 (dd, J=17.6, 9.6 Hz, 1H) 2.69 (dd, J=13.2, 4.2 Hz, 1H) 2.79 (ddq, J=15.9, 7.6, 2.0 Hz, 1H) 2.92 (dd, J=13.2, 8.3 Hz, 1H) 2.97 (dd, J=9.6, 1.7 Hz, 1H) 3.21 (dd, J=6.4, 4.9 Hz, 1H) 3.29 (m, 1H) 3.34 (dd, J=8.3, 4.15 Hz, 1H) 3.58 (br. s, 1H) 3.60 (br. d, J=11.3 Hz, 1H) 3.68-3.73 (m, 2H) 3.80 (br. s., 1H) 3.84-3.90 (m, 2H) 3.98 (d, J=2.3 Hz, 1H) 4.03-4.13 (m, 4H) 4.17 (dd, J=6.4, 4.9 Hz, 1H) 4.24 (ddd, J=11.3, 4.5, 1.5 Hz, 1H) 4.29 (dd, J=4.0, 1.9 Hz, 1H) 4.32 (td, J=10.2, 4.2 Hz, 1H) 4.44 (br. d, J=11.0 Hz, 1H) 4.59 (t, J=4.5 Hz, 1H) 4.62 (dd, J=7.4, 4.7 Hz, 1H) 4.69 (t, J=4.7 Hz, 1H) 4.80 (br. s., 1H) 4.87 (s, 1H) 5.00 (br. s., 1H) 5.05 (br. d, J=1.1 Hz, 1H)

ESI-MS (m/z): 1066.57 [M+H]$^+$, 1088.55 [M+Na]$^+$

Pharmacological Test Examples

General Information

Natural Halichondrin compounds and modified compounds thereof are known in the literature (See, e.g., D. Uemura et al. "Norhalichondrin A: An Antitumor Polyether Macrolide from a Marine Sponge" *J. Am. Chem. Soc.*, 107, 4796 (1985); Marc Litaudon et al. "Antitumor Polyether Macrolides: New and Hemisynthetic Halichondrins from the New Zealand Deep-Water Sponge Lissodendoryx sp." *J. Org. Chem.*, 1997, 62, 1868-1871). However, most of them are not easily available. For example, Dr. Uemura et. al. isolated 12.5 mg of Halichondrin B, 35.0 mg of Norhalichondrin A and 17.2 mg of Homohalichondrin A from as much as 600 kg of *Halichondria okadai* Kadota (See, e.g., D. Uemura et al. "Norhalichondrin A: An Antitumor Polyether Macrolide from a Marine Sponge" *J. Am. Chem. Soc.*, 107, 4796 (1985)). Among natural Halichondrin compounds, Halichondrin B shows the strongest anti-tumor activities against B-16 melanoma cells in vitro and is highly active against L-1210 Leukemia in vivo (See, e.g., D. Uemura et al. "Norhalichondrin A: An Antitumor Polyether Macrolide from a Marine Sponge" *J. Am. Chem. Soc.*, 107, 4796 (1985)). Halichondrin C is also active in various in vivo models but unstable in aqueous solution in comparison with Halichondrin B. Norhalichondrin B is much weaker than Halichondrin B not only in vitro but also in vivo See, e.g., D. Uemura et al. "Norhalichondrin A: An Antitumor Polyether Macrolide from a Marine Sponge" *J. Am. Chem. Soc.*, 107, 4796 (1985)). The following pharmacological tests use Halichondrin B (Hali-B) as reference compounds as needed.

Pharmacological Test Example 1. FaDu Growth Inhibition Assay

In this assay, the growth inhibitory activity of test compounds in a human squamous cell carcinoma of the head and neck (SCCHN) cell line FaDu was measured. FaDu cells were maintained in an RPMI-1640 (Wako Pure Chemical Industries, Ltd., 187-02021) medium containing 10% fetal bovine serum (FBS: Nichirei, 12D168), and penicillin and streptomycin in a 5% $CO_2$ incubator (37° C.). To each well of a 96 well plate (Becton, Dickinson and Company, 353219), 75 μL of FaDu cell suspension adjusted to a concentration of 4×10$^4$ cells/mL with the culture medium was added, and the cells were incubated overnight in a 5% $CO_2$ incubator (37° C.). On the next day, 25 μL of Compound (1) or Halichondrin B in three-fold dilution series suspended in the culture medium was added to each well, and the resultant was incubated for 3 days in a 5% $CO_2$ incubator (37° C.). Then, cell viability was determined by CellTiter-Glo® Luminescent Cell Viability Assay (Promega) with EnVision 2103 Multilabel Reader (Perkin-Elmer, Wellesley, Mass.). Value of the wells containing cells without adding the test compounds was defined as 100% and the value of the wells containing no cells was defined as 0%. The concentration of the test compound necessary for inhibiting the cell growth by 50% (i.e., an $IC_{50}$ value) was calculated, and shown in Table 1.

TABLE 1

| Test compound | FaDu ($IC_{50}$ (nM)) |
| --- | --- |
| Halichondrin B | 0.124 |
| Compound (1) | 0.0714 |

Pharmacological Test Example 2. MDA-MB231 Growth Inhibition Assay

In this assay, the growth inhibitory activity of test compounds in a human breast cancer cell line MDA-MB231 was measured. MDA-MB231 cells were maintained in Dulbecco's Modified Eagle's medium (Wako Pure Chemical Industries, Ltd., 044-29765) medium containing 10% fetal bovine serum (FBS: Nichirei, 12D168), and penicillin and streptomycin in a 5% $CO_2$ incubator (37° C.). To each well of a 96 well plate (Becton, Dickinson and Company, 353219), 75 μL of MDA-MB231 cell suspension adjusted to a concentration of 4×10$^4$ cells/mL with the culture medium was added, and the cells were incubated overnight in a 5% $CO_2$ incubator (37° C.). On the next day, 25 μL of Compound (1) or Halichondrin B in three-fold dilution series suspended in the culture medium was added to each well, and the resultant was incubated for 3 days in a 5% $CO_2$ incubator (37° C.). Then, cell viability was determined by CellTiter-Glo® Luminescent Cell Viability Assay (Promega) with EnVision 2103 Multilabel Reader (Perkin-Elmer, Wellesley, Mass.). Value of the wells containing cells without adding the test compounds was defined as 100% and the value of the wells containing no cells was defined as 0%. The concentration of the test compound necessary for inhibiting the cell growth by 50% (i.e., an $IC_{50}$ value) was calculated, and shown in Table 2.

TABLE 2

| Test compound | MDA-MB231 (IC$_{50}$ (nM)) |
|---|---|
| Halichondrin B | 1.000 |
| Compound (1) | 0.109 |

Pharmacological Test Example 3. HCC1954 Growth Inhibition Assay

In this assay, the growth inhibitory activity of test compounds in a human breast cancer cell line HCC1954 was measured. HCC1954 cells were maintained in an RPMI-1640 medium modified to contain 2 mM L-glutamine, 10 mM HEPES, 1 mM sodium pyruvate, 4500 mg/L glucose, and 1500 mg/L sodium bicarbonate (ATCC 30-2001) containing 10% fetal bovine serum (FBS: Nichirei, 12D168), and penicillin and streptomycin in a 5% $CO_2$ incubator (37° C.). To each well of a 96 well plate (Becton, Dickinson and Company, 353219), 75 μL of HCC1954 cell suspension adjusted to a concentration of 4×10$^4$ cells/mL with the culture medium was added, and the cells were incubated overnight in a 5% $CO_2$ incubator (37° C.). On the next day, 25 μL of Compound (1) or Halichondrin B in three-fold dilution series suspended in the culture medium was added to each well, and the resultant was incubated for 3 days in a 5% $CO_2$ incubator (37° C.). Then, cell viability was determined by CellTiter-Glo® Luminescent Cell Viability Assay (Promega) with EnVision 2103 Multilabel Reader (Perkin-Elmer, Wellesley, Mass.). Value of the wells containing cells without adding the test compounds was defined as 100% and the value of the wells containing no cells was defined as 0%. The concentration of the test compound necessary for inhibiting the cell growth by 50% (i.e., an IC$_{50}$ value) was calculated, and shown in Table 3.

TABLE 3

| Test compound | HCC1954 (IC$_{50}$ (nM)) |
|---|---|
| Halichondrin B | 0.154 |
| Compound (1) | 0.0668 |

Pharmacological Test Example 4. Antitumor Effects in FaDu Subcutaneous Xenograft Model in Mice as Monotherapy A human squamous cell carcinoma of the head and neck (SCCHN) cell line FaDu, which had been cultured in an RPMI-1640 medium containing 10% FBS, and penicillin and streptomycin, was adjusted to a concentration of 4.8×10$^7$ cells/mL with Hanks' Balanced Salt Solution to prepare a cell suspension. The cell suspension was inoculated in a volume of 100 μL into a subcutaneous part of a right flank of nude mice, 7 weeks of ages (CAnN.Cg-Foxn1nu/CrlCrlj, female, Charles River Laboratories Japan Inc.). Nine days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)× Shortest diameter (mm)×Shortest diameter (mm)/2

Relative tumor volume(RTV)=Tumor volume(day X)/Tumor volume(the first day)

Tumor Regression (%)=(1−minimum RTV)×100

On the basis of the volumes of tumors obtained on the first day of administration, the mice were grouped such that averages of the tumor volumes were substantially equal among the groups. Each test compound was dissolved in DMSO and a solution was stored at the freezer before use. Immediately before the administration, the stock solution was diluted in saline with 100 μM of hydroxypropyl-β-cyclodextrin. Each evaluation sample was intravenously administered at a maximum tolerable dose (MTD). Incidentally, the experiment was conducted on groups each consisting of 4 mice. Tumor regression (%) of each test compound was shown in Table 4.

TABLE 4

| Test compound | Dose (mg/kg) | Tumor Regression (%) |
|---|---|---|
| Halichondrin B | 0.05 | 0 |
| Compound (1) | 0.2 | 43 |

Pharmacological Test Example 5. Antitumor Activity Against OSC-19 in Subcutaneous Xenograft Model in Mice as Monotherapy A human squamous cell carcinoma of the head and neck (SCCHN) cell line OSC-19, which had been cultured in an DMEM/Ham's F-12 (1:1) medium containing 10% FBS, and penicillin and streptomycin, was adjusted to a concentration of 1×10$^8$ cells/ml with PBS to prepare a cell suspension, and the suspension was mixed with Matrigel™ (BD Bioscience, #366237) in a ratio of 1:1 to prepare a cell suspension in a concentration of 5×10$^7$ cell/mL. The cell suspension was inoculated in a volume of 100 μL into a subcutaneous part of a right flank of nude mice, 5 weeks of ages (CAnN.Cg-Foxn1nu/CrlCrlj, female, Charles River Laboratories Japan, Inc.). Six days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)× Shortest diameter (mm)×Shortest diameter (mm)/2

Relative tumor volume(RTV)=Tumor volume(day X)/Tumor volume(the first day)

Tumor Regression (%)=(1−minimum RTV)×100

On the basis of the volumes of tumors obtained on the first day of administration, the mice were grouped such that averages of the tumor volumes were substantially equal among the groups. The experiment was conducted on groups each consisting of 6 mice. Test compound was dissolved in saline and intravenously administered at doses from 0.06 mg/kg to 0.18 mg/kg once a week for 2 weeks (Q7D×2 schedule). Tumor regression (%) of each test dose is shown in Table 5.

TABLE 5

| Test compound | Dose (mg/kg) | Tumor Regression (%) |
|---|---|---|
| Compound (1) | 0.06 | 59 |
| Compound (1) | 0.18 | 90 |

Pharmacological Test Example 6. Antitumor Activity Against HCC1806 in Subcutaneous Xenograft Model in Mice as Monotherapy A human breast cancer cell line HCC1806, which had been cultured in an RPMI-1640 medium containing 10% FBS, and penicillin and streptomycin, was adjusted to a concentration of $1\times10^8$ cells/mL with PBS to prepare a cell suspension, and the suspension was mixed with Matrigel™ (BD Bioscience, #366237) in a ratio of 1:1 to prepare a cell suspension in a concentration of $5\times10^7$ cell/mL. The cell suspension was inoculated in a volume of 100 µL into a subcutaneous part of a right flank of nude mice, 5 weeks of ages (CAnN.Cg-Foxn1nu/CrlCrlj, female, Charles River Laboratories Japan, Inc.). Twelve days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)×
Shortest diameter (mm)×Shortest diameter
(mm)/2

Relative tumor volume(RTV)=Tumor volume(day
X)/Tumor volume(the first day)

Tumor Regression (%)=(1−minimum RTV)×100

On the basis of the volumes of tumors obtained on the first day of administration, the mice were grouped such that averages of the tumor volumes were substantially equal among the groups. The experiment was conducted on groups each consisting of 6 mice. Test compound was dissolved in saline and intravenously administered at 0.18 mg/kg once a week for 2 weeks (Q7D×2 schedule). Tumor regression (%) for Compound (1) is shown in Table 6.

TABLE 6

| Test compound | Dose (mg/kg) | Tumor Regression (%) |
|---|---|---|
| Compound (1) | 0.18 | 90 |

Pharmacological Test Example 7. Antitumor Effects in FaDu Subcutaneous Xenograft Model in Combination with Cetuximab in Mice A human squamous cell carcinoma of the head and neck (SCCHN) cell line FaDu, which had been cultured in an RPMI-1640 medium containing 10% FBS, and penicillin and streptomycin, was adjusted to a concentration of $5\times10^7$ cells/mL with Hanks' Balanced Salt Solution to prepare a cell suspension. The cell suspension was inoculated in a volume of 100 µL into a subcutaneous part of a right flank of nude mice, 7 weeks of ages (CAnN.Cg-Foxn1nu/CrlCrlj, female, Charles River Laboratories Japan Inc.). Ten days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)×
Shortest diameter (mm)×Shortest diameter
(mm)/2

Relative tumor volume(RTV)=Tumor volume(day
X)/Tumor volume(the first day)

Tumor Regression on day 35(%)=(1−RTV on day
35)×100

On the basis of the volumes of tumors obtained on the first day of administration, the mice were grouped such that averages of the tumor volumes were substantially equal among the groups. Each test compound was dissolved in DMSO and a solution was stored at the freezer before use. Immediately before the administration, the stock solution was diluted in saline with 100 µM of hydroxypropyl-β-cyclodextrin. Each test compound and was intravenously administered at doses from ¼ MTD to ½ MTD in combination with cetuximab (Erbitux, Merck Serono Co., Ltd.). Incidentally, the experiment was conducted on groups each consisting of 4 mice. Tumor regression on day 35(%) of each test compound are shown in Table 7.

TABLE 7

| Test compound | Dose (mg/kg) | Cetuximab (mg/kg) | Tumor Regression on day 35 (%) |
|---|---|---|---|
| — | — | 20 | −242 |
| Halichondrin B | 0.0125 | 20 | −38 |
|  | 0.025 | 20 | −2 |
| Compound (1) | 0.05 | 20 | 38 |
|  | 0.1 | 20 | 60 |

Pharmacological Test Example 8. Antitumor Activity in KPL-4 Subcutaneous Xenograft Model in Combination with Trastuzumab in Mice A human HER-2 positive breast cancer cell line KPL-4, which had been cultured in an RPMI-1640 medium containing 10% FBS, and penicillin and streptomycin, was adjusted to a concentration of $1\times10^8$ cells/mL with Hank's Balanced Salt Solution to prepare a cell suspension. The cell suspension was inoculated in a volume of 100 µL into a subcutaneous part of a right flank of nude mice, 7 weeks of ages (CAnN.Cg-Foxn1nu/CrlCrlj, female, Charles River Laboratories Japan, Inc.). Sixteen days after the cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)×
Shortest diameter (mm)×Shortest diameter
(mm)/2

Relative tumor volume(RTV)=Tumor volume(day
X)/Tumor volume(the first day)

Tumor Regression (%)=(1−minimum RTV)×100

On the basis of the volumes of tumors obtained on the first day of administration, the mice were grouped such that averages of the tumor volumes were substantially equal among the groups. The experiment was conducted on groups each consisting of 6 mice. Each test compound was dissolved in DMSO and a solution was stored at the freezer before use. Immediately before the administration, the stock solution was diluted in saline. The test compound was intravenously administered at 0.09 mg/kg or 0.18 mg/kg in combination with trastuzumab (Herceptin, Genentech, Inc.). Tumor regression for Compound (1) is shown in Table 8.

TABLE 8

| Test compound | Dose (mg/kg) | Trastuzumab (mg/kg) | Tumor Regression (%) |
|---|---|---|---|
| — | — | 10 | 0 |
| Compound (1) | 0.09 | — | 43 |
| | 0.09 | 10 | 83 |
| | 0.18 | — | 87 |
| | 0.18 | 10 | 100 |

Pharmacological Test Example 9. Effect on CD31-Positive Vessel in the FaDu Subcutaneous Model in Mice A human squamous cell carcinoma of the head and neck (SCCHN) cell line FaDu, which had been cultured in an RPMI-1640 medium containing 10% FBS, and penicillin and streptomycin, was adjusted to a concentration of $5 \times 10^7$ cells/mL with PBS to prepare a cell suspension. The cell suspension was inoculated in a volume of 100 μL into a subcutaneous part of a right flank of nude mice, 7 weeks of ages (CAnN.Cg-Foxn1nu/CrlCrlj, female, Charles River Laboratories Japan, Inc.). Ten days after cell inoculation, a test compound in saline with 100 μM of hydroxypropyl-β-cyclodextrin was intravenously administered at doses from ½ MTD to MTD. The experiment was conducted on groups each consisting of 3 mice. Five days after administration, tumor samples were collected and fixed with IHC Zinc Fixative (BD Pharmingen) at 4° C. for 24 hr. Paraffin-embedded tissues were sectioned (3 μm), mounted on positively charged slides, and air-dried. Immunohistochemical staining of CD31 was conducted using Ventana autostainer model Discover XT (Roche Diagnostics) according to the manufacture's protocol. Sections were deparaffinized, conditioned and the antigens were retrieved with CC1 (Ventana Medical Systems). Slides were blocked with Blocker A and Blocker B (Endogenous biotin blocking kit, Roche Diagnostics). Rat anti-mouse IgG CD31 antibody (Dianova GmbH) was applied at 2 μg/mL. Sections were incubated with the antibody for 6 hr, followed by 32 minutes incubation with biotinylated anti-rat IgG antibody (Jackson ImmunoResearch Laboratories) at 2.2 μg/mL. The detection was performed with Streptavidin-HRP D for 16 min, followed by incubation with DAB D and DAB H₂O₂ D (DABMap kit, Ventana Medical Systems, Inc) for 8 min. Slides were counterstained with Hematoxylin II (Roche Diagnostics) for 16 min, followed by incubation with Bluing reagent for 4 min. Sections were dehydrated in graded ethanols, defatted in xylene replacement and covered with DPX (Merck KGaA).

Immunostained slides were scanned using Vectra 2 Automated Slide Imaging System (Perkin Elmer Inc.). The number of blood vessels in the whole tumor was quantified by counting the CD31-positive objects using inForm 2 software (PerkinElmer Inc.) Area of the tumor region was measured by assessing the hematoxylin-staining area using inform 2 software (PerkinElmer Inc.) The number of blood vessels was normalized by the area of the tumor region. An increase rate of the blood vessel number of the test compound-dosing group was calculated with the below formula, and shown in Table 9.

Increase rate of blood vessel number (%)=((blood vessel number of the test compound-dosing group-blood vessel number of the control group)/blood vessel number of the control group)×100

TABLE 9

| Test compound | Dose (mg/kg) | Increase rate of blood vessel number (%) |
|---|---|---|
| Halichondrin B | 0.025 | 31 |
| | 0.05 | 39 |
| Compound (1) | 0.10 | 69 |
| | 0.20 | 154 |

Pharmacological Test Example 10. Effect on α-SMA Positive-CAFs in the FaDu Subcutaneous Model A human squamous cell carcinoma of the head and neck (SCCHN) cell line FaDu, which had been cultured in an RPMI-1640 medium containing 10% FBS, and penicillin and streptomycin, was adjusted to a concentration of $5 \times 10^7$ cells/mL with PBS to prepare a cell suspension. The cell suspension was inoculated in a volume of 100 μL into a subcutaneous part of a right flank of nude mice, 5 to 6 weeks of ages (CAnN.Cg-Foxn1nu/CrlCrlj, female, Charles River Laboratories Japan, Inc.). Ten days after cell inoculation, a test compound in saline with 100 μM of hydroxypropyl-β-cyclodextrin was intravenously administered at ½ MTD and MTD. The experiment was conducted on groups each consisting of 3 mice. Two days after administration, tumor samples were collected and fixed with IHC Zinc Fixative (BD Pharmingen) at 4° C. for 24 hr. Paraffin-embedded tissues were sectioned (3 m), mounted on positively charged slides, and air-dried for 6 hr. Immunohistochemical staining of α-SMA was conducted using Ventana autostainer model Discover XT (Roche Diagnostics). Sections were deparaffinized, conditioned and the antigens were retrieved with proprietary buffers, EZPrep and CC1 (Ventana Medical Systems). Mouse anti-α-SMA monoclonal antibody conjugated with alkaline phosphatase (clone 1A4, Sigma) was applied at 5 μg/mL. Sections were incubated with the antibody for 6 hr. The detection was performed with Red-Map kit (Ventana Medical Systems, Inc). Sections were dehydrated in graded ethanols, defatted in xylene replacement and covered with DPX (Merck KGaA). The serial tumor slices were deparaffinized and stained with Mayer's hematoxylin (Muto Pure Chemicals) for 1 min. Sections were dehydrated in graded ethanols, defatted in xylene replacement and covered with DPX (Merck KGaA).

Immunostained slides were scanned using Vectra 2 Automated Slide Imaging System (Perkin Elmer Inc.). The area of the α-SMA-positive region in the whole tumor was quantified by counting the α-SMA-positive objects using inForm 2 software (PerkinElmer Inc.). Area of the tumor region was measured by assessing the hematoxylin-staining area using inForm 2 software (PerkinElmer Inc.). The area of the α-SMA positive region was normalized by the area of the tumor region. A suppression rate of the α-SMA positive area of the test compound-dosing group was calculated with the below formula, and shown in Table 10.

TABLE 10

| Test compound | Dose (mg/kg) | Suppression rate of α-SMA positive area (%) |
|---|---|---|
| Halichondrin B | 0.025 | 7 |
|  | 0.05 | 3 |
| Compound (1) | 0.10 | 21 |
|  | 0.20 | 28 |

Suppression rate of α-SMA positive area (%) = − ((α-SMA positive area of the test compound-dosing group − α-SMA positive area of the control group)/α-SMA positive area of the control group) × 100

Pharmacological Test Example 11. HSC-2 Orthotopic Transplantation Mouse Model

Luciferase-transduced HSC-2-Luc cells were established by retrovirus-mediated gene transfer. First, the DNA fragment encoding firefly luciferase was obtained from pGL3-enhancer plasmid (GenBank#:U47297), and subcloned into the retroviral vector pCX4pur (GenBank#: AB086386). Then, helper-free recombinant retroviruses were produced by transfecting the above retroviral expression vector together with pGP and pE-Ampho plasmids (Takara Bio; Shiga, Japan), into 293T cells (ATCC; Manassas, USA). Next, HSC-2 cells were infected with the recombinant retroviruses, and were cultured for two weeks in the presence of puromycin (2 µg/mL). The infected cells were selected from a polyclonal proliferative population of the culture.

Under anesthesia, the human SCCHN cell line, HSC-2-Luc was inoculated into tongue of female nude mice ($1\times10^6$ cells in 50 µL of PBS), 6 weeks of ages (CAnN.Cg-Foxn1nu/CrlCrlj mice; Charles River, Inc.; Shizuoka, Japan). Seven days after transplantation, the tumor volume was analyzed using bioluminescence signal from HSC-2-Luc cells. For bioluminescence imaging, 0.1 mL of 15 mg/mL D-luciferin (Promega, Madison, Wis.) was injected intraperitoneally into nude mice under 1% to 2% inhaled isoflurane anesthesia. The bioluminescence signal was monitored using the IVIS SPECTRUM series (PerkinElmer, Waltham, Mass.), consisting of a highly sensitive, cooled chargecoupled device camera. Living Image software (PerkinElmer, Waltham, Mass.) was used to grid the imaging data and integrate the total bioluminescence signal in each region-of-interest (ROI). All bioluminescence images were acquired with a 1 second exposure. Data were analyzed using total photon flux emission (photons/second) in the ROIs.

On the basis of the total photon flux emission obtained on the first day of administration, the mice were grouped such that averages of the total photon flux emission were substantially equal among the groups. Compound (1) or cisplatin was intravenously administered with or without cetuximab (Erbitux, Merck Serono Co., Ltd.) once a week for 3 weeks (Q7D×3 schedule). Two experiments were conducted using the identical procedure and all data were collected from the experiments. Each group consisted of 16 mice.

Figure 6A:
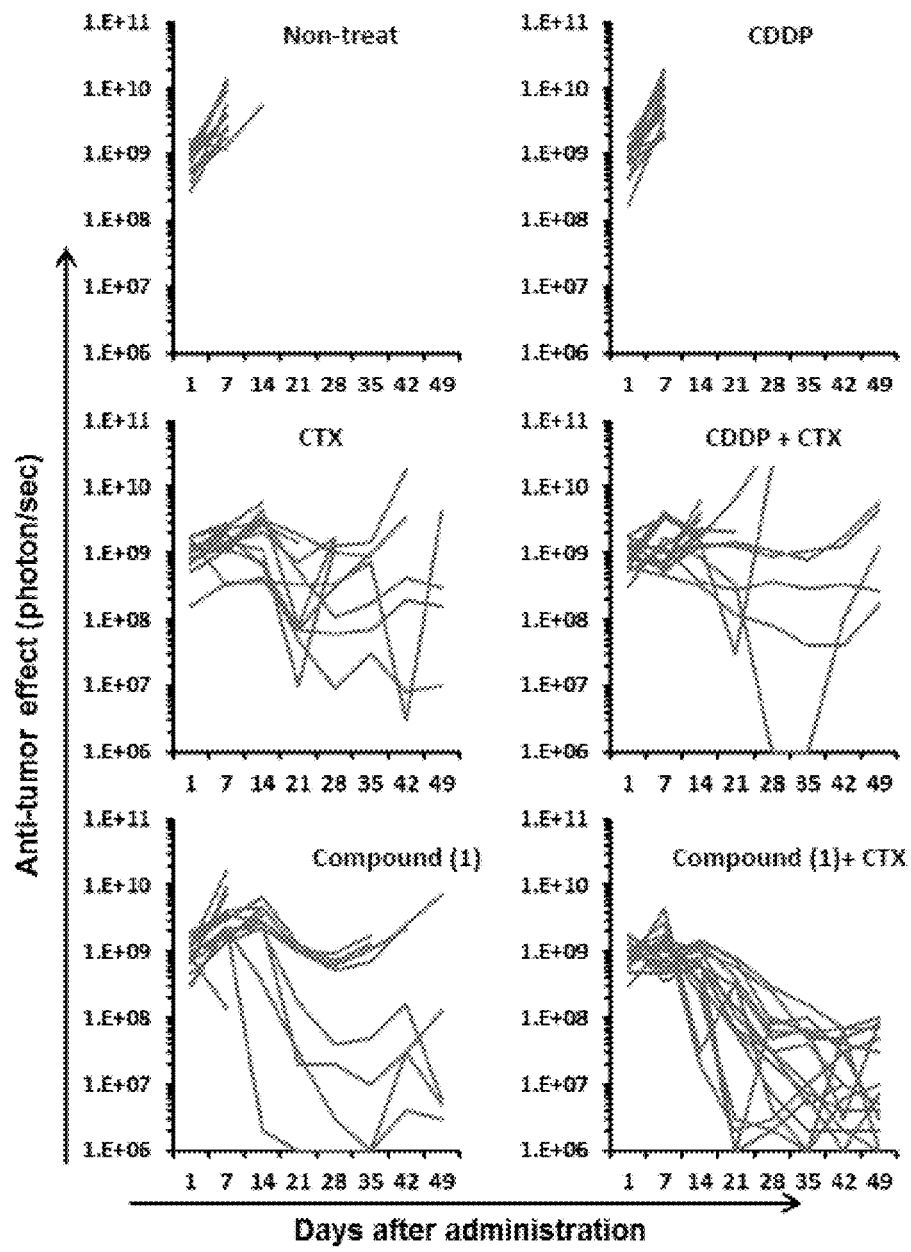
FIG. 6A-6B show anti-tumor effect of Compound (1) in HSC-2 orthotopic transplantation mouse model.
Figure 6B:
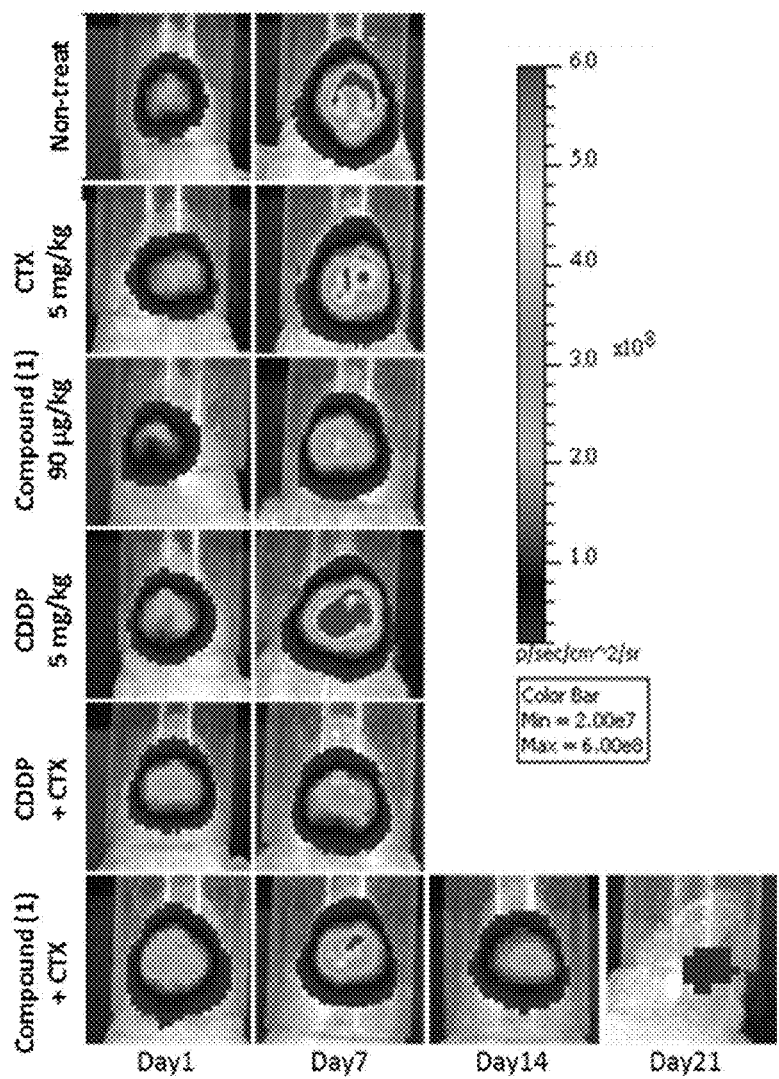
Figure 7A:
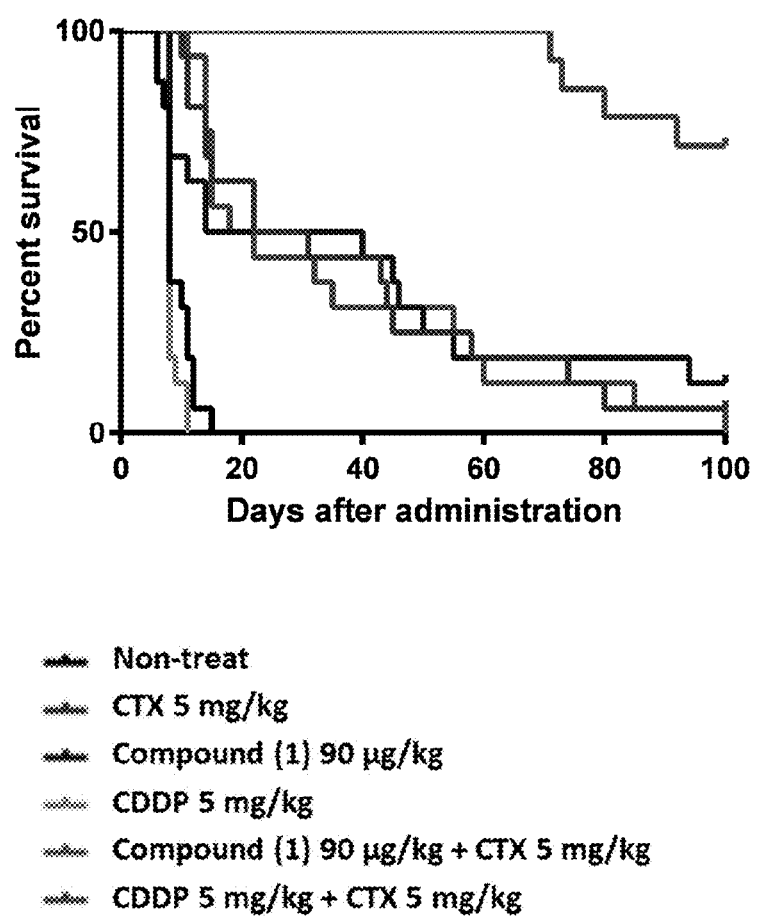
FIG. 7A-7B show survival advantage of Compound (1) in combination with cetuximab in HSC-2 orthotopic transplantation mouse model.
Figure 7B:
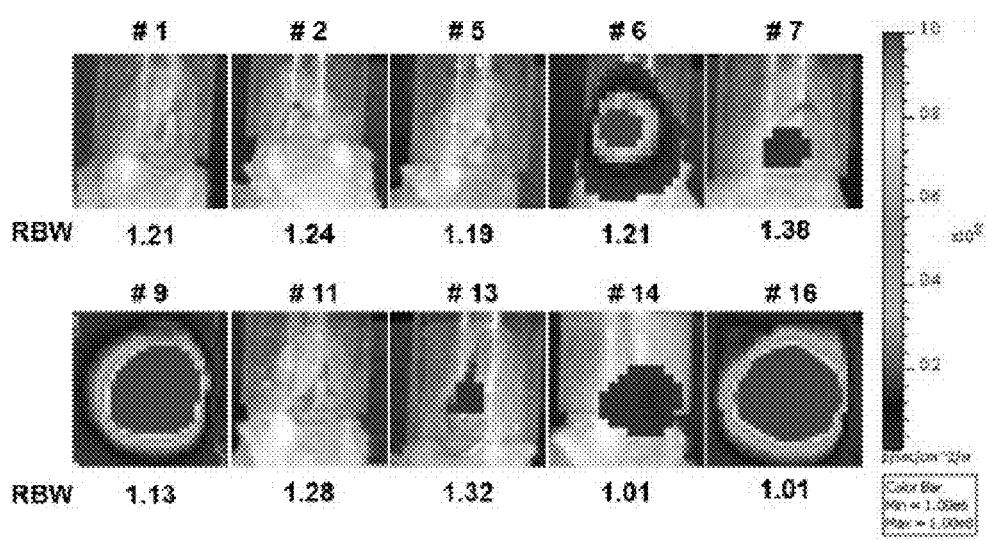
Figure 8A:
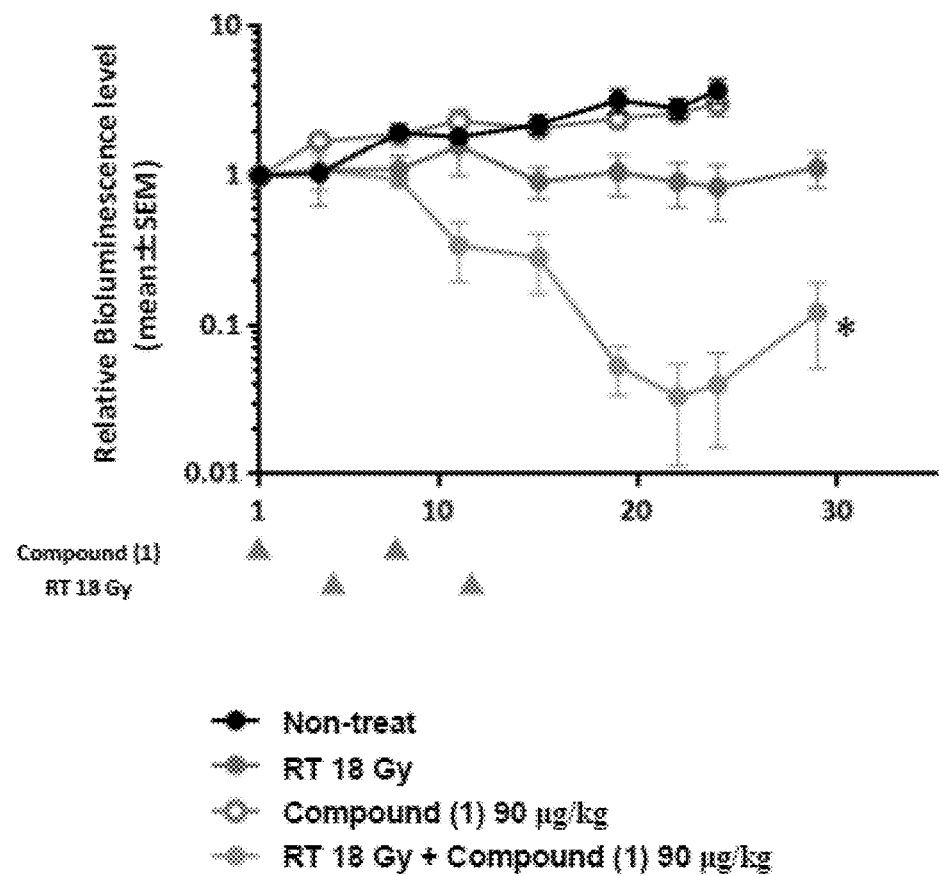
FIG. 8A-8B show anti-tumor effect of Compound (1) in combination with radiation therapy in FaDu mouse xenograft model.
Figure 8B:
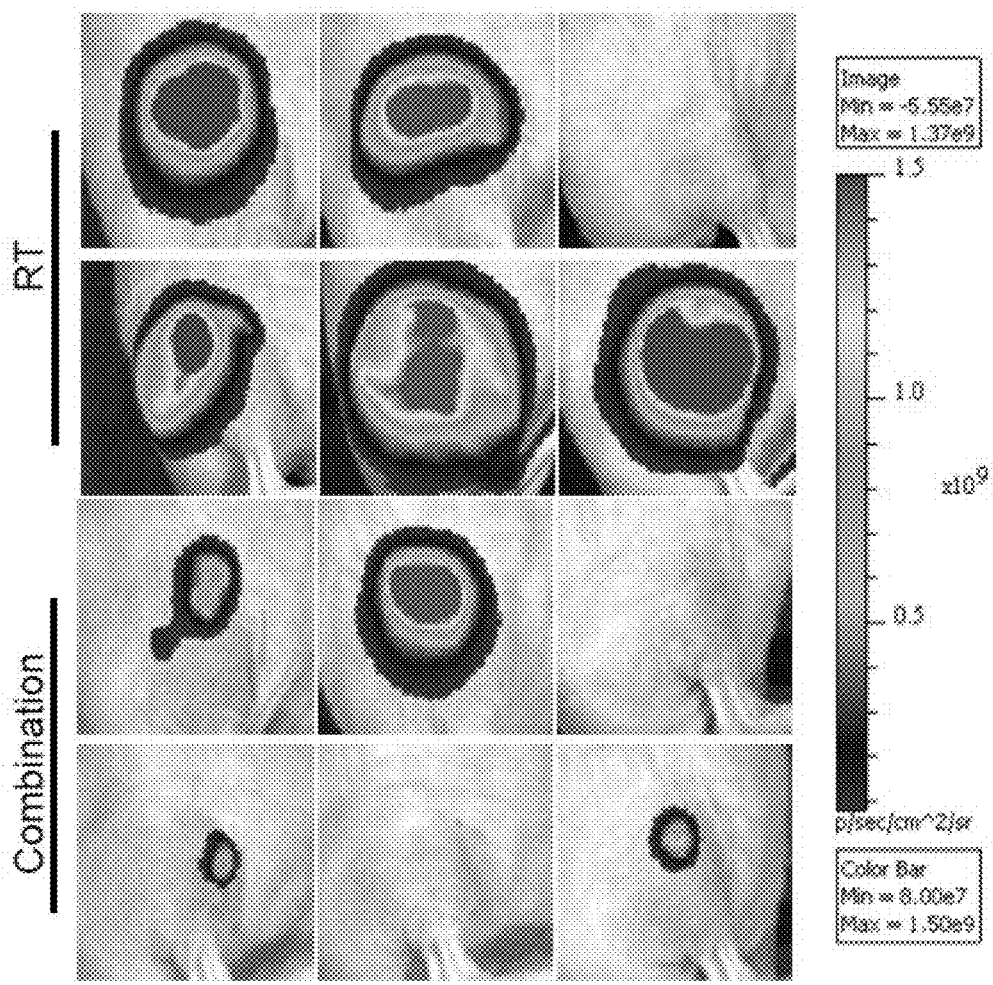
Figure 9:
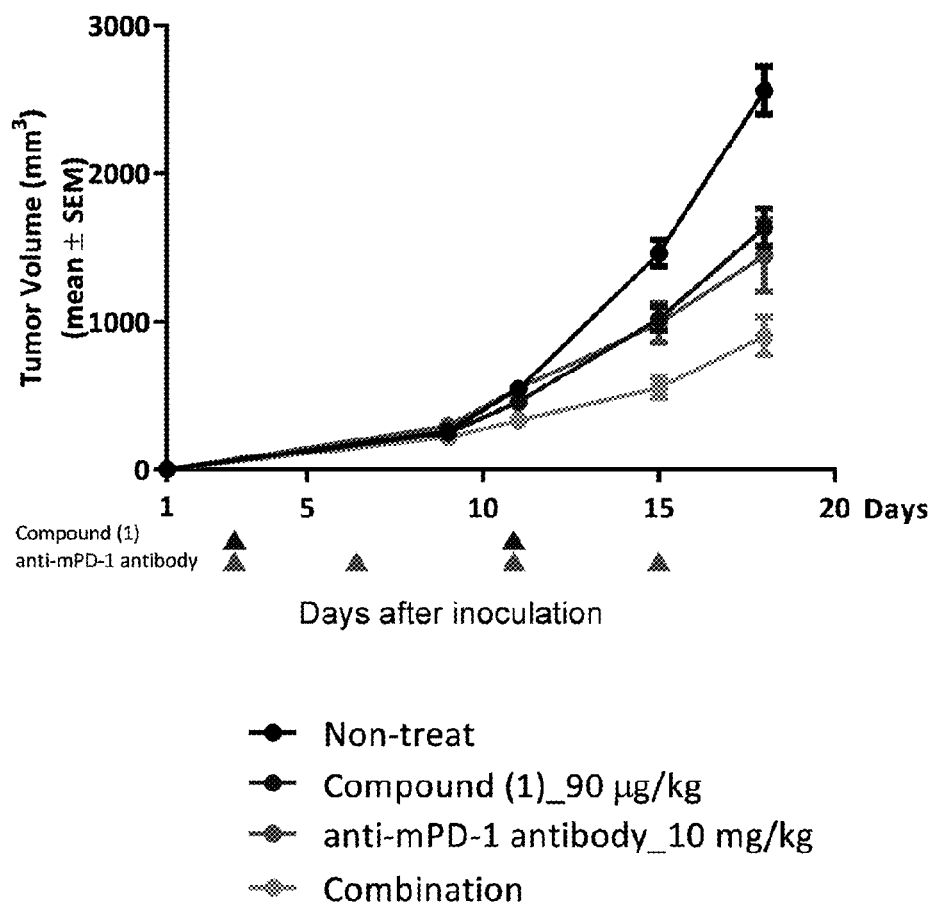
FIG. 9 shows anti-tumor activities of Compound (1) in combination with anti-mPD-1 antibody. CT26 s.c. syngeneic mouse model (colon carcinoma) was treated with Compound (1) and anti-mPD-1 antibody in Q7D schedule and twice a week schedule, respectively, for 3 weeks. Results show means±SEM of tumor volumes ($mm^3$) (n=8).

The imaging data showed that only the treatment of Compound (1) with cetuximab clearly reduced the bioluminescence signal in all mice after Day 14 (FIG. 6A-6B). Median survival time (MST) was calculated for each group of treatment as the median of the days of death. Increase Life Span (ILS) was calculated by the following formula: ILS (%)=(MST of animals treated with test compound−MST of control animals)/MST of control animals×100. ILS (%) of each test compound is shown in Table 11.

TABLE 11

| Test compound | Dose (mg/kg) | Cetuximab (mg/kg) | ILS (%) |
|---|---|---|---|
| — | — | 5 | 231 |
| Cisplatin | 5 | — | 0 |
|  | 5 | 5 | 150 |
| Compound (1) | 0.09 | — | 238 |
|  | 0.09 | 5 | >1150 |

Pharmacological Test Example 12. FaDu s.c. Xenograft Model in Combination with Radiation Luciferase-transduced FaDu-Luc cells were established by retrovirus-mediated gene transfer. First, the DNA fragment encoding firefly luciferase was obtained from pGL3-enhancer plasmid (GenBank#:U47297), and subcloned into the retroviral vector pCX4pur (GenBank#: AB086386). Then, helper-free recombinant retroviruses were produced by transfecting the above retroviral expression vector together with pGP and pE-Ampho plasmids (Takara Bio; Shiga, Japan), into 293T cells (ATCC; Manassas, USA). Next, FaDu cells were infected with the recombinant retroviruses, and were cultured for two weeks in the presence of puromycin (2 µg/mL). The infected cells were selected from a polyclonal proliferative population of the culture.

A luciferase-transduced human SCCHN cell line FaDu-Luc, which had been cultured in an RPMI-1640 medium containing 10% FBS, and penicillin and streptomycin, was adjusted to a concentration of $5\times10^7$ cells/mL with Hank's Balanced Salt Solution to prepare a cell suspension. The cell suspension was inoculated in a volume of 100 µL into a subcutaneous part of a right thigh of nude mice, 6 weeks of ages (CAnN.Cg-Foxn1nu/CrlCrlj, female, Charles River Laboratories Japan, Inc.). Thirteen days after the cell inoculation, the tumor volume was analyzed using bioluminescence signal from FaDu-Luc cells. For bioluminescence imaging, 0.1 mL of 15 mg/mL D-luciferin (Promega, Madison, Wis.) was injected intraperitoneally into nude mice under 1% to 2% inhaled isoflurane anesthesia. The bioluminescence signal was monitored using the IVIS SPECTRUM series (PerkinElmer, Waltham, Mass.), consisting of a highly sensitive, cooled chargecoupled device camera. Living Image software (PerkinElmer, Waltham, Mass.) was used to grid the imaging data and integrate the total bioluminescence signal in each region-of-interest (ROI). All bioluminescence images were acquired with a 1 second exposure. Data were analyzed using total photon flux emission (photons/second) in the ROIs. The total photon flux emission was calculated in accordance with the following calculation formulae:

Relative bioluminescence level=Total photon flux emission(day $X$)/Total photon flux emission(the first day)

Tumor Regression (%)=(1−minimum Relative bioluminescence level)×100

On the basis of the total photon flux emission obtained on the first day of administration, the mice were grouped such that averages of the total photon flux emission were substantially equal among the groups. The experiment was conducted on groups each consisting of 6 mice. Compound (1) was administered via tail vein injection on day 1 and 8. Irradiation was performed 18 Gy on day 4 and day 11. Tumor regression for Compound (1) is shown in Table 12.

TABLE 12

| Test compound | Dose (mg/kg) | Radiation (Gy) | Tumor Regression (%) |
|---|---|---|---|
| — | — | 18 | 16 |
| Compound (1) | 0.09 | — | 0 |
|  | 0.09 | 18 | 97 |

Pharmacological Test Example 13. Antitumor Activity in CT26 Subcutaneous Syngeneic Model in Combination with Anti-mPD-1 Antibody in Mice A murine undifferentiated colon carcinoma cell line CT26, which had been cultured in an RPMI-1640 medium containing 10% FBS, and penicillin and streptomycin, was adjusted to a concentration of $2\times10^7$ cells/mL with Hank's Balanced Salt Solution to prepare a cell suspension. On day 1, the cell suspension was inoculated in a volume of 100 µL into a subcutaneous part of a right flank of BALB/c mice, 6 weeks of ages (BALB/cAnNCrlCrlj, female, Charles River Laboratories Japan, Inc.). Two days after the cell inoculation, the mice were randomly divided into four groups and each group consists of 8 mice. The shortest diameter and the longest diameter of a tumor in each mouse were measured by using an electronic digital caliper (Digimatic™ caliper, Mitutoyo Corporation), so as to calculate the volume of the tumor in accordance with the following calculation formula:

Tumor volume (mm³)=Longest diameter (mm)× Shortest diameter (mm)×Shortest diameter (mm)/2

T/C=(mean tumor volume of treated group)/(mean tumor volume of control group)

Inhibition of tumor growth (%)=(1−T/C)×100

The test compound was intravenously administered at 0.09 mg/kg on days 3 and 11. Anti-mPD-1 antibody (BE0146, Bio X Cell) was intravenously administered at 10 mg/kg on days 3, 7, 11, and 15. Inhibition of tumor growth on day 15(%) of each test compound is shown in Table 13.

TABLE 13

| Test compound | Dose (mg/kg) | Anti-mPD-1 antibody (mg/kg) | Inhibition of tumor growth on day 15 (%) |
|---|---|---|---|
| — | — | 10 | 32 |
| Compound (1) | 0.09 | — | 30 |
|  | 0.09 | 10 | 62 |

Figure 10A:
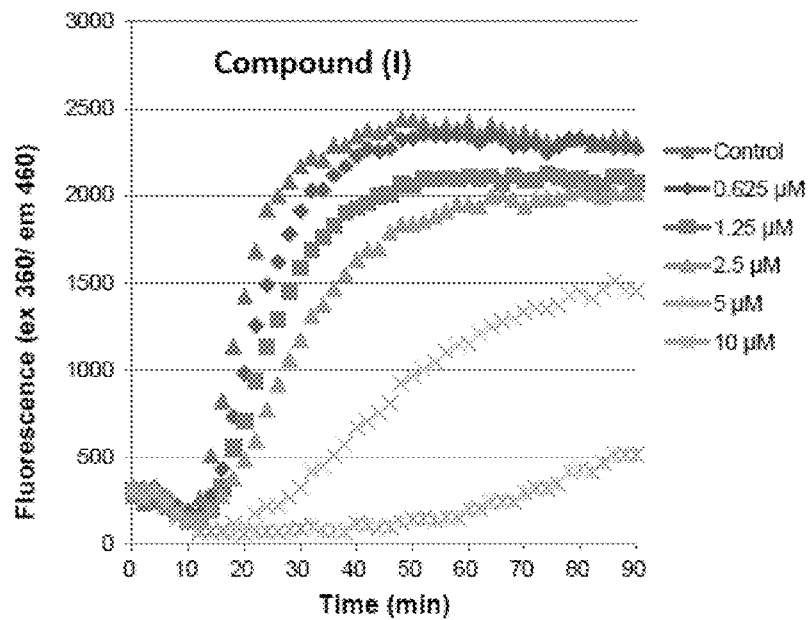
FIG. 10A shows a cell-free tubulin polymerization assay. Compound (1) has inhibitory activity on tubulin polymerization.

Pharmacological Test Example 14. Effect on Tubulin Polymerization In Vitro (FIG. 10A)

Tubulin Polymerization Assay kit was purchased from Cytoskeleton, Inc. (Cat.#BK011P). The kit contained 1 bottle of lyophilized tubulin protein purified from porcine brain, 3 tubes of lyophilized GTP, 2 bottles of lyophilized assay buffer, and 1 bottle of tubulin glycerol buffer. Assay buffer was prepared by dissolving the contents in 10 mL of deionized and sterilized water. This solution contained 80 mmol/L piperazine-N,N'-bis[2-ethanesulfonic acid] sesquisodium salt, 2.0 mmol/L magnesium chloride, 0.5 mmol/L ethylene glycol-bis(2-amino-ethyl ether) N,N,N',N'-tetra-acetic acid, pH 6.9, and 10 µmol/L fluorescent reporter. The buffer was stored at −70° C. until use. Tubulin glycerol buffer consisted of 80 mmol/L piperazine-N,N'-bis[2-ethanesulfonic acid] sesquisodium salt, 2.0 mmol/L magnesium chloride, 0.5 mmol/L ethylene glycol-bis(2-amino-ethyl ether) N,N,N',N'-tetra-acetic acid, and 60% v/v glycerol, pH 6.9. It was stored at 4° C. until use. GTP stock solution was prepared by dissolving the contents of each tube in 100 µL of deionized and sterilized water to achieve a concentration of 100 mmol/L GTP. Aliquots of this stock were stored at −70° C. until use. Tubulin stock solution (10 mg/mL) was prepared by dissolving the tubulin powder adding 1.1 mL of the mixture of assay buffer and GTP stock solution (100:1, v/v). Aliquots were frozen in liquid nitrogen, and then stored at −70° C. until use.

In the tubulin polymerization assay, reaction mixture was prepared by mixing 820 µL of assay buffer, 17.6 µL of GTP stock solution, and 600 µL of tubulin glycerol buffer. Reaction mixture (1015 µL) was combined with 240 µL of the tubulin stock solution. This solution was called as tubulin reaction mixture and used for the measurement of test and control wells. No tubulin reaction mixture was prepared by mixing 89.85 µL of reaction mixture and 21.25 µL of assay buffer for the measurement of blank wells. The Compound (1) solution (6.25-100 µmol/L; final concentrations 0.625-10 µmol/L), or vehicle was added at 5 µL to individual wells of a 96-well half-area microtiter plate. Tubulin reaction mixture or no tubulin reaction mixture was added at 45 µL to each well of the plate. Fluorescence emission at 460 nm (excitation wavelength at 360 nm) was measured every 2 minutes for 90 minutes using the SpectraMax® M5e microplate reader (Molecular Devices). Tubulin polymerization was followed by fluorescence enhancement due to the incorporation of a fluorescence reporter into microtubules as polymerization occurred. The assay was performed in duplicate. The assay demonstrated that Compound (1) inhibited tubulin polymerization in a concentration-dependent manner. The fluorescence intensity in each time point was calculated by the following formulas:

Fluorescence intensity=mean fluorescence measurement of test wells or control wells−mean fluorescence measurement of blank wells;blank well:with vehicle without tubulin;control well: with vehicle and tubulin;test well:with compounds and tubulin.

Figure 10B:
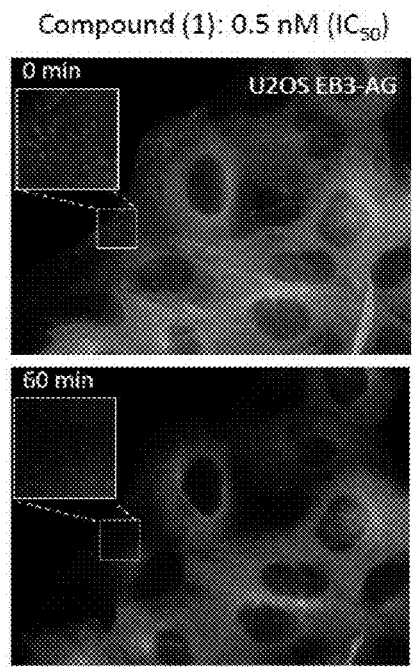
FIG. 10B shows a microtubule dynamics assay. Compound (1) also has inhibitory activity on microtubule dynamics.

Pharmacological Test Example 15. Cell-Based Microtubule Dynamics Assay (FIG. 10B)

A cell-based microtubule (MT) dynamics assay was conducted with the U2OS-EB3-AG osteosarcoma cell line, in which the fusion protein of EB3 (a microtubule plus end binding protein) and Azami-Green (EB3-AG) was stably expressed. U2OS-EB3-AG cells were culture in RPMI-1640 medium containing 10% FBS, and penicillin-streptomycin, at 37° C. in a humidified 5% $CO_2$ atmosphere. The MT dynamics in the live cells can be visualized as the movement of the comet-like structure of EB3-AG. U2OS-EB3-AG cells plated on glass-base culture plates (EZVIEW plate, AGC Techno Glass, Japan) were treated with Compound (1) at the indicated concentration and the microtubule dynamics were monitored by time-lapse imaging using fluorescent microscope with 60-fold magnification oil-immersed objective lens (BZ-X710, KEYENCE, Japan). The still images at the indicated time points were presented in FIG. 10B. Higher magnification views of the boxed areas were shown in inlets. When treated with Compound (1) at 0.5 nM ($IC_{50}$ value for antiproliferative activity in U2OS-EB3-AG cells), the comet-like structures became hard to observe at around 60 minutes after the addition of the compound. These results clearly demonstrated that Compound (1) had the ability to suppress the MT dynamics.

Figures 11, 12:
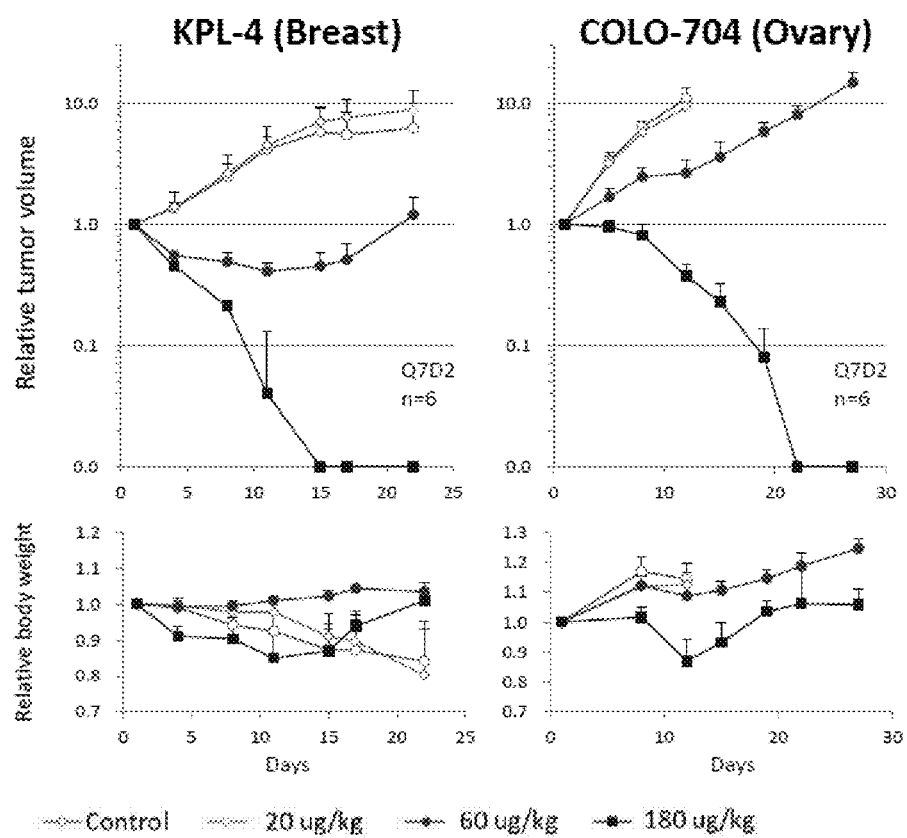
FIG. 11 shows that Compound (1) is a potent antiproliferative agent in esophageal cancer (OE21, OE33, and TE-8) and uterine cancer (MES-SA, MES-SA/Dx5-Rx1) cell lines.
FIG. 12 shows that Compound (1) has potent anti-tumor activity in subcutaneous xenograft models of breast and ovarian cancer (KPL-4 and COLO-704, respectively) as a monotherapy.

Pharmacological Test Example 16. In Vitro Antiproliferative Activity (FIG. 11)

The in vitro antiproliferative assays for Compound (1) were conducted using a small panel of cancer cell lines including human squamous cell carcinoma of the esophagus (OE21, TE-8), human adenocarcinoma of the esophagus (OE33), and human uterine sarcoma (MES-SA, MES-SA-Dx5-Rx1). All cell lines were cultured in RPMI-1640 medium containing 10% FBS, and penicillin-streptomycin (culture medium), in a 5% $CO_2$ incubator (37° C.). To each well of a 96 well plate (Becton, Dickinson and Company, 353219), 75 µL of cell suspension adjusted to a concentration of $4 \times 10^4$ cells/mL with the culture medium was added, and the cells were incubated overnight in a 5% $CO_2$ incubator (37° C.). On the next day, 25 µL of Compound (1) in three-fold dilution series suspended in the culture medium was added to each well, and the resultant was incubated for 72 hours in a 5% $CO_2$ incubator (37° C.). Then, cell viability was determined by CellTiter-Glo® Luminescent Cell Viability Assay (Promega) with 2013 EnVision™ Multilabel Reader (Perkin-Elmer, Wellesley, Mass.). Value of the wells containing cells without adding the test compounds was defined as 100% and the value of the wells containing no cells was defined as 0%. The concentration of Compound (1) necessary for inhibiting the cell growth by 50% (i.e., an $IC_{50}$ value) was calculate, and is shown in FIG. 11. The P-gp susceptibility was calculated as the ratio of the $IC_{50}$ value in MES-SA-Dx5-Rx1 cells, which overexpress P-gp, to the $IC_{50}$ value in MES-SA cells.

Pharmacological Test Example 17. Antitumor Effects in the KPL-4 Xenograft Models in Mice as Monotherapy; Antitumor Effects in the COLO-704 Xenograft Models in Mice as Monotherapy (FIG. 12)

A human HER-2 positive breast cancer cell line KPL-4, which had been cultured in a DMEM containing 10% FBS, and penicillin-streptomycin, was adjusted to a concentration of $1 \times 10^8$ cells/mL with Hanks' Balanced Salt Solution to prepare a cell suspension. The cell suspension was inoculated in a volume of 100 µL into a subcutaneous part of a right flank of nude mice, 8 weeks of ages (CAnN.Cg-Foxn1nu/CrlCrlj, female, Charles River Laboratories Japan Inc.). Eleven days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume ($mm^3$)=Longest diameter (mm)× Shortest diameter (mm)×Shortest diameter (mm)/2

Relative tumor volume(RTV)=Tumor volume(day X)/Tumor volume(the first day)

Relative body weight(RBW)=Body weight(day X)/Body weight(the first day)

On the basis of the volumes of tumors obtained on Day 1, the mice were grouped such that averages of the tumor volumes were substantially equal among the groups. The experiment was conducted on groups each consisting of six mice. The test compound was dissolved in DMSO and a solution was stored in the freezer before use. Immediately before the administration, the stock solution was diluted with saline. The test compound in saline was intravenously once-weekly administered at 20 µg/kg, 60 µg/kg, or 180 µg/kg for 2 weeks (on Day 1 and Day 8). The tumor regression was observed in 60 µg/kg- and 180 µg/kg-treated groups, and the administration at 180 µg/kg completely eradicated the xenograft tumors in all mice on Day 15.

A human ovarian cancer cell line COLO-704, which had been cultured in a RPMI-1640 containing 10% FBS, and penicillin-streptomycin, was adjusted to a concentration of $1 \times 10^8$ cells/mL with Hanks' Balanced Salt Solution to prepare a cell suspension. The cell suspension was inoculated in a volume of 100 µL into a subcutaneous part of a right flank of nude mice, 5 weeks of ages (CAnN.Cg-Foxn1nu/CrlCrlj, female, Charles River Laboratories Japan Inc.). Nine days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume ($mm^3$)=Longest diameter (mm)× Shortest diameter (mm)×Shortest diameter (mm)/2

Relative tumor volume(RTV)=Tumor volume(day X)/Tumor volume(the first day)

Relative body weight(RBW)=Body weight(day X)/Body weight(the first day)

On the basis of the volumes of tumors obtained on Day 1, the mice were grouped such that averages of the tumor volumes were substantially equal among the groups. The experiment was conducted on groups each consisting of six mice. The test compound was dissolved in DMSO and a solution was stored in the freezer before use. Immediately before the administration, the stock solution was diluted with saline. The test compound in saline was intravenously once-weekly administered at 20 µg/kg, 60 µg/kg, or 180 µg/kg for 2 weeks (on Day 1 and Day 8). The compound treatment induced tumor regression at 180 µg/kg and tumor growth delay at 60 µg/kg. The administration at 180 µg/kg completely eradicated the xenograft tumors in all mice on Day 22.

Figure 13:
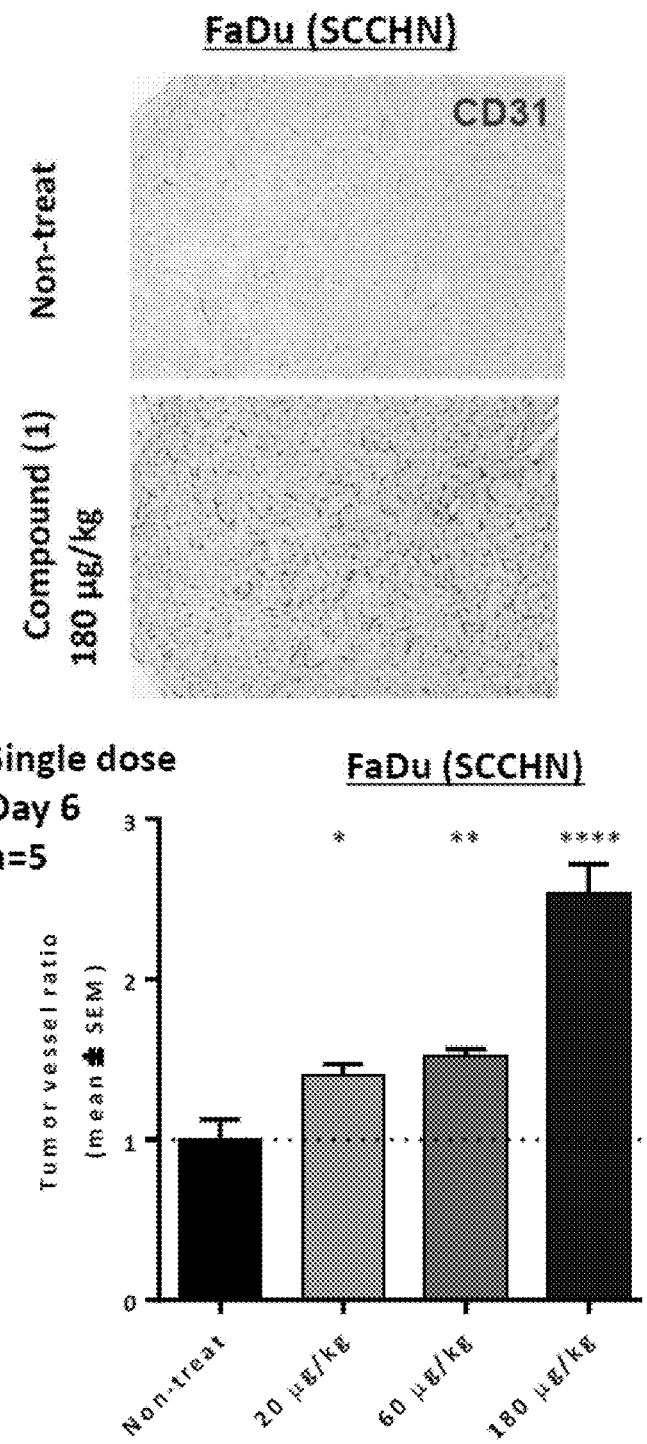
FIG. 13 shows the effect of Compound (1) on tumor microenvironments. As shown, Compound (1) increases microvessel density. *P<0.05, P<0.01, **P<0.0001 versus non-treat (Dunnett multiple comparison test).

Pharmacological Test Example 18. Effect on CD31-Positive Vessel in the FaDu Subcutaneous Model in Mice (FIG. 13)

A human squamous cell carcinoma of the head and neck (SCCHN) cell line FaDu, which had been cultured in an RPMI-1640 medium containing 10% FBS, and penicillin-streptomycin (culture medium), was adjusted to a concentration of $5 \times 10^7$ cells/mL with culture medium to prepare a cell suspension. The cell suspension was inoculated in a volume of 100 µL into a subcutaneous part of a right flank of nude mice, 6 weeks of ages (CAnN.Cg-Foxn1nu/CrlCrlj, female, Charles River Laboratories Japan, Inc.). Ten days after cell inoculation, the mice were grouped such that averages of the tumor volumes were substantially equal among the groups. The experiment was conducted on groups each consisting of 6 mice. Each test compound was dissolved in DMSO and a solution was stored in the freezer before use. Immediately before the administration, the stock solution was diluted with saline. The test compound in saline was intravenously administered at 20 μg/kg, 60 μg/kg, or 180 μg/kg. Five days after the single administration, tumor samples were collected and fixed with IHC Zinc Fixative (BD Pharmingen) at 4° C. for 24 hours. Paraffin-embedded tissues were sectioned (3 am), mounted on positively charged slides, and air-dried. Immunohistochemical staining of CD31 was conducted using Ventana autostainer model Discover XT (Roche Diagnostics) according to the manufacture's protocol. Sections were deparaffinized, conditioned and the antigens were retrieved with CC1 (Ventana Medical Systems). Slides were blocked with Blocker A and Blocker B (Endogenous biotin blocking kit, Roche Diagnostics). Rat anti-mouse IgG CD31 antibody (Dianova GmbH) was applied at 2 μg/mL. Sections were incubated with the antibody for 6 hours, followed by 32 minutes incubation with biotinylated anti-rat IgG antibody (Jackson ImmunoResearch Laboratories) at 2.2 μg/mL. The detection was performed with Streptavidin-HRP D for 16 minutes, followed by incubation with DAB D and DAB $H_2O_2$ D (DABMap kit, Ventana Medical Systems, Inc.) for 8 minutes. Slides were counterstained with Hematoxylin II (Roche Diagnostics) for 16 min, followed by incubation with Bluing reagent for 4 minutes. Sections were dehydrated in graded ethanols, defatted in xylene replacement and covered with DPX® (Merck KGaA). Immunostained slides were scanned using Vectra® 2 Automated Slide Imaging System (Perkin Elmer Inc.). The number of blood vessels in the whole tumor was quantified by counting the CD31-positive objects using inform 2 software (PerkinElmer Inc.) Area of the tumor region was measured by assessing the hematoxylin-staining area using inform 2 software (PerkinElmer Inc.) The number of blood vessels was normalized by the area of the tumor region. The single administration of test compound at doses of 20, 60, and 180 μg/kg increased the tumor blood vessel number. The ratios of blood vessel number in the test compound-dosing groups compared to non-treat group were calculated with the below formula:

Tumor vessel ratio=blood vessel number of the test compound-dosing group/blood vessel number of the non-treat group)

Figure 14:
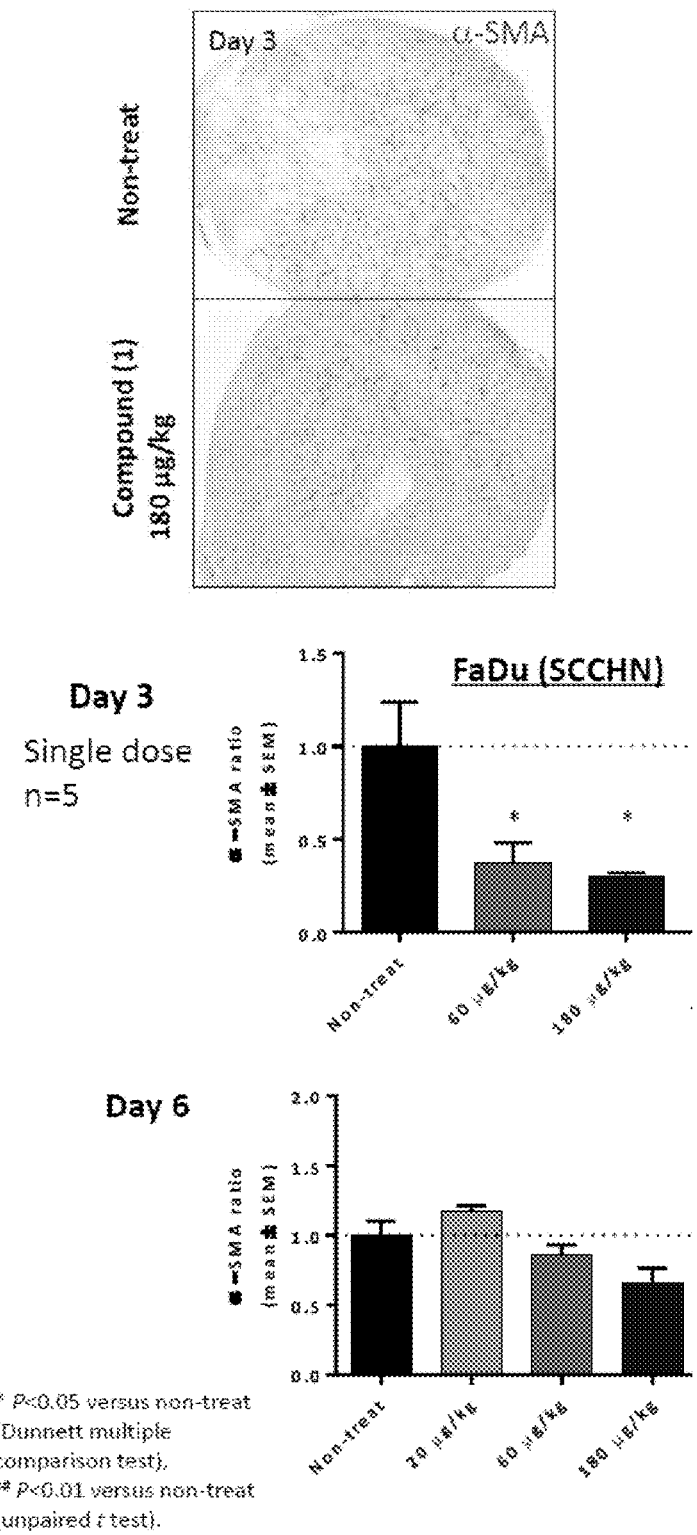
FIG. 14 shows the effect of Compound (1) on tumor microenvironments. As shown, Compound (1) reduces α-SMA positive CAFs.

Pharmacological Test Example 19. Effect on α-SMA-Positive CAFs in the FaDu Subcutaneous Model in Mice (FIG. 14)

Figure 15:
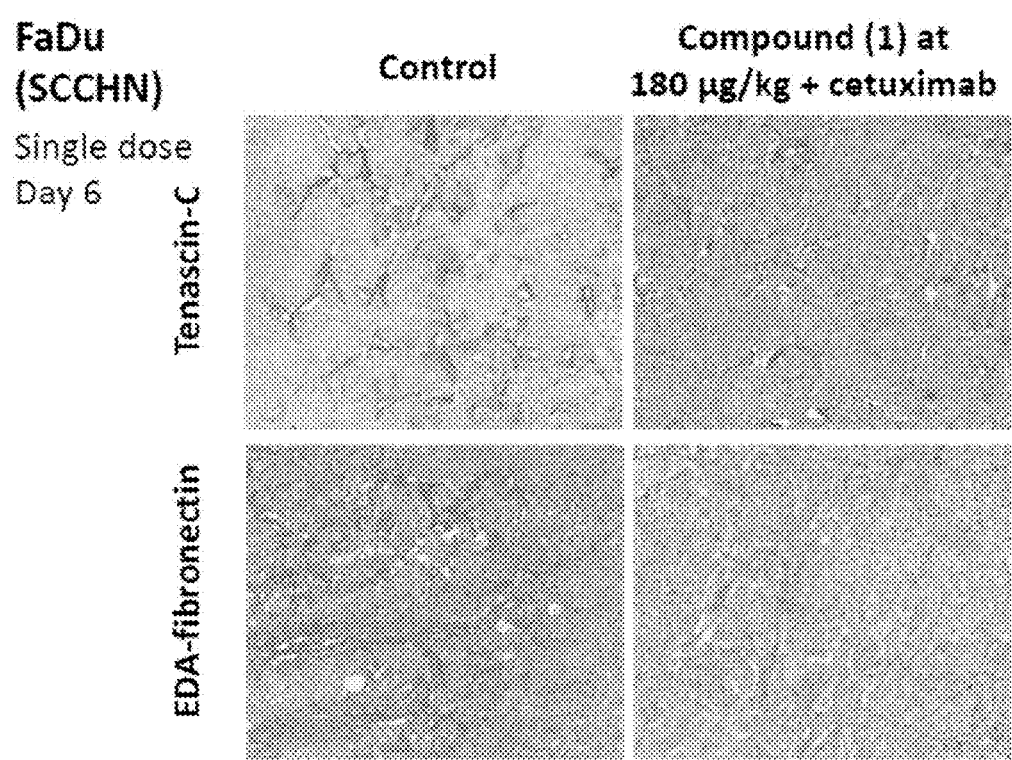
FIG. 15 shows that Compound (1) decreases ECM proteins from CAFs in FaDu subcutaneous xenograft model. FaDu xenograft tumors were collected on Day 6 after single administration of Compound (1) 180 μg/kg+cetuximab on Day 1.

A human squamous cell carcinoma of the head and neck (SCCHN) cell line FaDu, which had been cultured in an RPMI-1640 medium containing 10% FBS, and penicillin-streptomycin (culture medium), was adjusted to a concentration of $5 \times 10^7$ cells/mL with culture medium to prepare a cell suspension. The cell suspension was inoculated in a volume of 100 μL into a subcutaneous part of a right flank of nude mice, 6 weeks of ages (CAnN.Cg-Foxn1nu/CrlCrlj, female, Charles River Laboratories Japan, Inc.). Ten days after cell inoculation, the mice were grouped such that averages of the tumor volumes were substantially equal among the groups. The experiment was conducted on groups each consisting of 5 mice. Each test compound was dissolved in DMSO and a solution was stored in the freezer before use. Immediately before the administration, the stock solution was diluted with saline. The test compound in saline was intravenously administered at 20 μg/kg, 60 μg/kg, or 180 μg/kg. Two days or 5 days after the single administration, tumor samples were collected and fixed with IHC Zinc Fixative (BD Pharmingen) at 4° C. for 24 hours. Paraffin-embedded tissues were sectioned (3 am), mounted on positively charged slides, and air-dried. Sections were deparaffinized, conditioned and the antigens were retrieved using microwave with 1 mM EDTA at pH 6.0. Sections were blocked with 1% of BSA in TBS. Mouse anti-α-SMA monoclonal antibody conjugated with alkaline phosphatase (clone 1A4, Sigma) was applied at 5 μg/mL. Sections were incubated with the antibody for 2.5 hr. The detection was performed with Fast red II substrate kit (Nichirei Bioscience Inc.). Sections were counterstained with Mayer's Hematoxylin (Muto Pure Chemicals) for 50 seconds. Sections were dehydrated in graded ethanols, defatted in xylene replacement and covered with DPX (Merck KGaA). Immunostained slides were scanned using Vectra 2 Automated Slide Imaging System (Perkin Elmer Inc.). The area of α-SMA-positive region in the whole tumor was quantified by counting the α-SMA-positive objects using inform 2 software (PerkinElmer Inc.) Area of the tumor region was measured by assessing the hematoxylin-staining area using inform 2 software (PerkinElmer Inc.). The area of the α-SMA-positive region was normalized by the area of the tumor region. The single administration of test compound significantly reduced the α-SMA positive area at doses of 60 and 180 μg/kg on Day 3 and at a dose of 180 μg/kg on Day 6. A suppression rate of the α-SMA-positive area of the test compound-dosing group was calculated with the below formula:

α-SMA ratio=α-SMA area of the test compound-dosing group/α-SMA area of the non-treat group Pharmacological Test Example 20. Effects on Tenascin-C and EDA-Fibronectin in the FaDu Subcutaneous Model in Mice (FIG. 15)

A human squamous cell carcinoma of the head and neck (SCCHN) cell line FaDu, which had been cultured in an RPMI-1640 medium containing 10% FBS, and penicillin-streptomycin (culture medium), was adjusted to a concentration of $5 \times 10^7$ cells/mL with culture medium to prepare a cell suspension. The cell suspension was inoculated in a volume of 100 μL into a subcutaneous part of a right flank of nude mice, 6 weeks of ages (CAnN.Cg-Foxn1nu/CrlCrlj, female, Charles River Laboratories Japan, Inc.). Ten days after cell inoculation, the mice were grouped such that averages of the tumor volumes were substantially equal among the groups. The experiment was conducted on groups each consisting of 5 mice. Compound (1) was dissolved in DMSO and a solution was stored in the freezer before use. Compound (1) (180 μg/kg) and Cetuximab (CTX, Erbitux®, Merck Serono Co. Ltd.) (10 mg/kg) was diluted with saline and intravenously injected on Day 1. Five days after the single administration, tumor samples were collected and fixed with IHC Zinc Fixative (BD Pharmingen) at 4° C. for 24 hr. Paraffin-embedded tissues were sectioned (3 am), mounted on positively charged slides, and air-dried. Sections were deparaffinized, conditioned and the antigens were retrieved using microwave with 1 mM EDTA at pH 6.0 for Tenascin-C. For EDA-fibronectin, the antigens retrieval procedure was not necessary. Sections were incubated with BLOXALL Blocking Solution (Vector Labs) for 10 min to block endogenous peroxidase, and with Mouse on Mouse Ig Blocking Reagent (Vector Labs) for 1 hour, and then with 2.5% normal horse serum for 30 minutes. For immunohistochemical staining of Tenascin-C, mouse anti-Tenascin-C monoclonal antibody (clone 4C8MS, IBL) was applied at 5 µg/mL. Sections were incubated with the antibody overnight at 4° C. For immunohistochemical staining of EDA-fibronectin, mouse anti-EDA-fibronectin monoclonal antibody (clone IST-9, Abcam) was applied at 1.5 µg/mL. Sections were incubated with the antibody for 1 hour at room temperature. The detection was performed with Mouse On Mouse ImmPRESS™ Peroxidase Polymer Kit (Vector Labs). Sections were counterstained with Mayer's Hematoxylin (Muto Pure Chemicals) for 50 sec. Sections were dehydrated in graded ethanols, defatted in xylene replacement and covered with DPX (Merck KGaA). Immunostained slides were scanned using Vectra 2 Automated Slide Imaging System (Perkin Elmer Inc.). The expression levels of both Tenascin-C and ED-A fibronectin were reduced in the Compound (1) and CTX treated tumors compared with control tumors.

Figure 16:
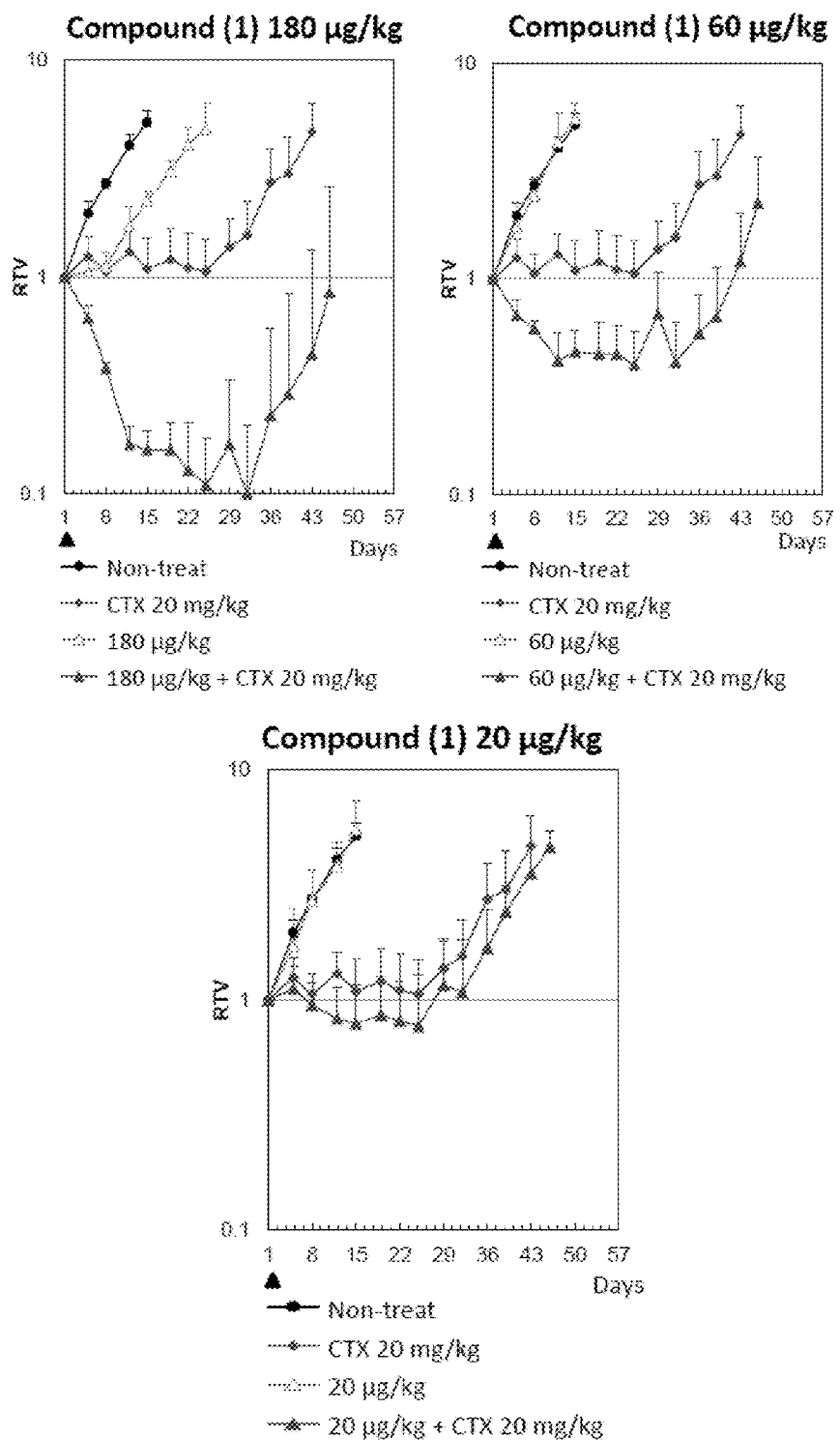
FIG. 16 shows that Compound (1) exhibits a dose-dependent combinational effect with cetuximab in a FaDu subcutaneous xenograft model. Single dose, n=6. Compound (1) and cetuximab (CTX) were administered on Day 1 in the FaDu xenograft model.

Pharmacological Test Example 21. Antitumor Effects in FaDu Subcutaneous Xenograft Model in Combination with Cetuximab in Mice (FIG. 16)

A human squamous cell carcinoma of the head and neck (SCCHN) cell line FaDu, which had been cultured in an RPMI-1640 medium containing 10% FBS, and penicillin-streptomycin, was adjusted to a concentration of $5 \times 10^7$ cells/mL with Hanks' Balanced Salt Solution to prepare a cell suspension. The cell suspension was inoculated in a volume of 100 µL into a subcutaneous part of a right flank of athymic mice (CAnN.Cg-Foxn1nu/CrlCrlj, female, 7 weeks old, Charles River Japan Inc.). Ten days after cell inoculation (Day 1), the length and the width of a tumor in each mouse were measured by using an electronic digital caliper (Mitutoyo Corporation), so as to calculate the volume of the tumor in accordance with the following calculation formula:

Tumor volume (mm$^3$)=Longest diameter (mm)×Shortest diameter (mm)×Shortest diameter (mm)/2

Relative tumor volume(RTV)=Tumor volume(day X)/Tumor volume(the first day)

On the basis of TV, the mice were randomly grouped (Day 1). Each group was consisted in six mice. Compound (1) was dissolved in DMSO and a solution was stored in the freezer before use. Compound (1) (20, 60, or 180 µg/kg) and Cetuximab (CTX, Erbitux®, Merck Serono Co., Ltd.) (10 mg/kg) was diluted with saline and intravenously injected on Day 1. Changes of RTV of each group were shown in FIG. 16. At doses of 180 µg/kg and 60 µg/kg, antitumor efficacies of Compound (1) with CTX were stronger than that of CTX monotherapy with tumor regression. The antitumor efficacy of Compound (1) at doses of 20 mg/kg in combination with CTX tended to be stronger than that of CTX monotherapy.

Figure 17:
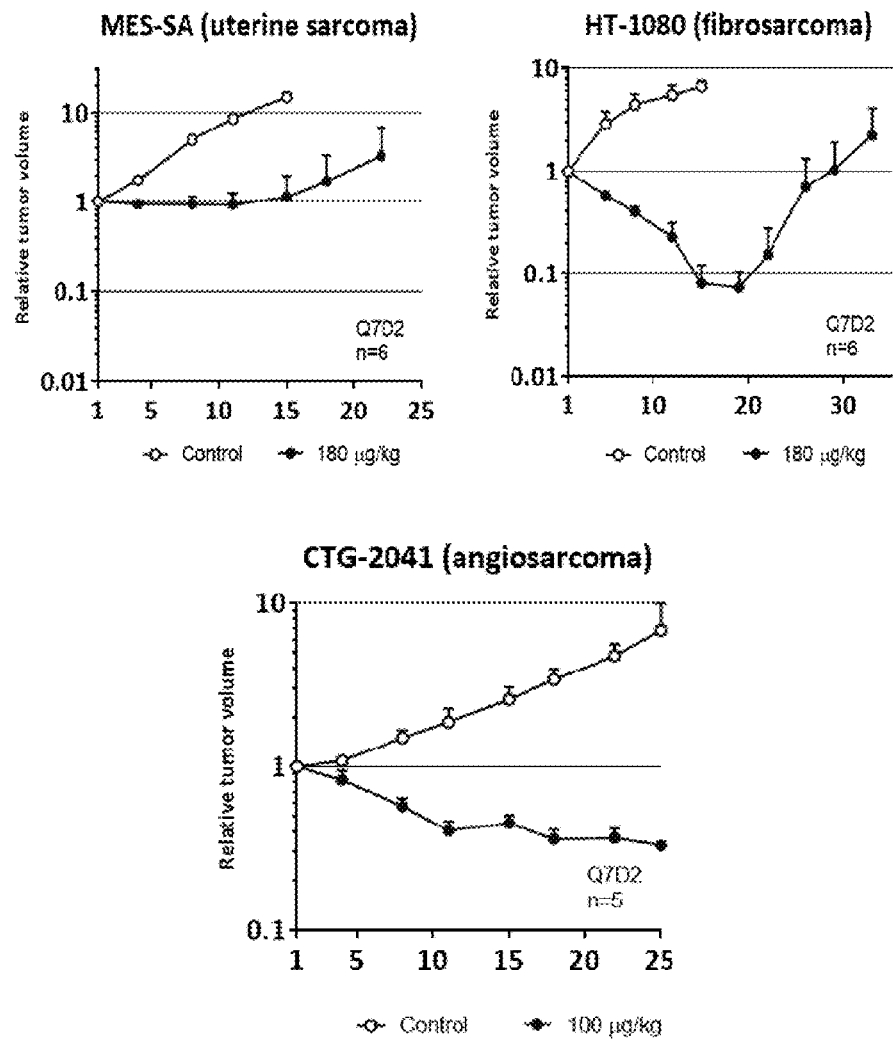
FIG. 17 shows antitumor effects in the soft tissue sarcoma xenograft models in mice as monotherapy. MES-SA (human uterine sarcoma), HT-1080 (human fibrosarcoma), and CTG-2041 (human angiosarcoma) are shown.

Pharmacological Test Example 22. Antitumor Effects in the Soft Tissue Sarcoma Xenograft Models in Mice as Monotherapy (FIG. 17)

MES-SA

A human uterine sarcoma cell line MES-SA, which had been cultured in an RPMI-1640 containing 10% FBS, and penicillin-streptomycin, was adjusted to a concentration of $2 \times 10^8$ cells/mL with Hanks' Balanced Salt Solution to prepare a cell suspension, and the suspension was mixed with Geltrex® (Thermo Fisher Scientific Inc., #A1413202) in a ratio of 1:1 to prepare a cell suspension in a concentration of $1 \times 10^8$ cells/mL. The cell suspension was inoculated in a volume of 100 µL into a subcutaneous part of a right flank of nude mice, 6 weeks of ages (CAnN.Cg-Foxn1nu/CrlCrlj, female, Charles River Laboratories Japan Inc.). Six days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm$^3$)=Longest diameter (mm)×Shortest diameter (mm)×Shortest diameter (mm)/2

Relative tumor volume(RTV)=Tumor volume(day X)/Tumor volume(the first day)

On the basis of the volumes of tumors obtained on Day 1, the mice were grouped such that averages of the tumor volumes were substantially equal among the groups. The experiment was conducted on groups each consisting of 6 mice. The test compound was dissolved in DMSO and a solution was stored in the freezer before use. Immediately before the administration, the stock solution was diluted with saline. The test compound in saline was intravenously once-weekly administered at 180 µg/kg for 2 weeks (on Day 1 and Day 8). The antitumor activity was observed with tumor growth delay in the treated group.

HT-1080

A human fibrosarcoma cell line HT-1080, which had been cultured in an E-MEM containing 10% FBS, NEAA and antibiotics was adjusted to a concentration of $3 \times 10^7$ cells/mL with medium to prepare a cell suspension. The cell suspension was inoculated in a volume of 100 µL into a subcutaneous part of a right flank of athymic mice (CAnN.Cg-Foxn1nu/CrlCrlj, female, 6 weeks old, Charles River Japan Inc.). Six days after cell inoculation (Day 1), the length and the width of a tumor in each mouse were measured by using an electronic digital caliper (Mitutoyo Corporation), so as to calculate the volume of the tumor in accordance with the following calculation formula:

Tumor volume (mm$^3$)=Longest diameter (mm)×Shortest diameter (mm)×Shortest diameter (mm)/2

Relative tumor volume(RTV)=Tumor volume(day X)/Tumor volume(the first day)

On the basis of TV, the mice were randomly grouped (Day 1). Each group was consisted in six mice. Compound (1) was dissolved in DMSO and a solution was stored in the freezer before use. Compound (1) (180 µg/kg) was diluted with saline and intravenously injected on Day 1 and Day 8. Changes of RTV of each group was shown in FIG. 17. The antitumor activity was observed with tumor regression in the treated group.

CTG-2041

Tumor fragments of human angiosarcoma CTG-2041 were implanted s.c. in the left flank of female mice. Tumor growth was monitored twice a week using digital caliper, so as to calculate the volume of the tumor in accordance with the following calculation formula:

Tumor volume (mm$^3$)=Longest diameter (mm)×Shortest diameter (mm)×Shortest diameter (mm)/2

Relative tumor volume(RTV)=Tumor volume(day X)/Tumor volume(the first day)

When the volume of tumors reached approximately 200 mm³, animals are matched by tumor volume into treatment or control groups and dosing initiated on Day 1. Each group was consisted with five mice. Compound (1) was dissolved in DMSO and a solution was stored in the freezer before use. Compound (1) (100 µg/kg) diluted in saline and intravenously injected on Day 1 and Day 8. Changes of RTV of each group were shown in FIG. 17. The antitumor activity was observed with tumor regression in the treated group.

Figure 18:
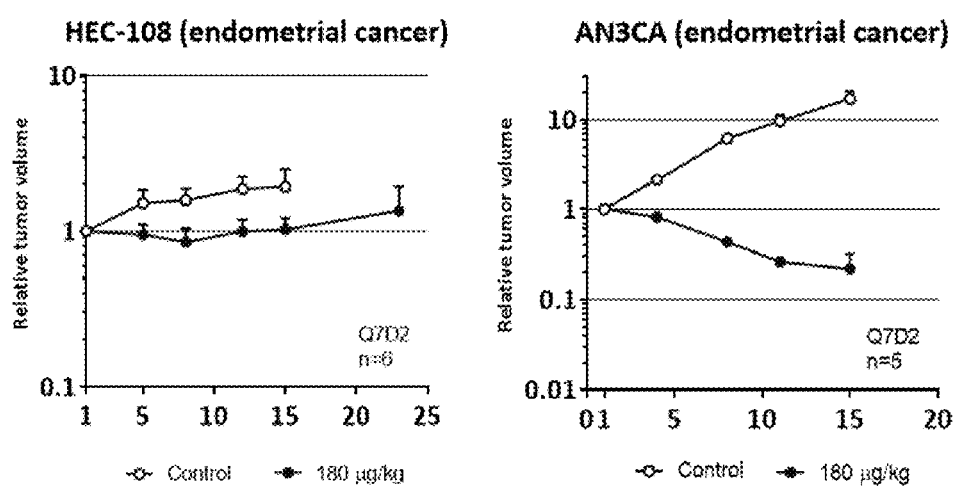
FIG. 18 shows antitumor effects in endometrial cancer xenograft models in mice as monotherapy. HEC-108 and AN3CA (endometrial cancer) are shown.

Pharmacological Test Example 23. Antitumor Effects in the Endometrial Cancer Sarcoma Xenograft Models in Mice as Monotherapy (FIG. 18)

HEC-108

A human endometrial cancer cell line HEC-108, which had been cultured in an E-MEM containing 15% FBS and antibiotics were adjusted to a concentration of $7.14 \times 10^7$ cells/mL with medium to prepare a cell suspension. The cell suspension was inoculated in a volume of 150 µL into a subcutaneous part of a right flank of athymic mice (CAnN.Cg-Foxn1nu/CrlCrlj, female, 6 weeks old, Charles River Japan Inc.). Thirteen days after cell inoculation (Day 1), the length and the width of a tumor in each mouse were measured by using an electronic digital caliper (Mitutoyo Corporation), so as to calculate the volume of the tumor in accordance with the following calculation formula:

Tumor volume (mm³)=Longest diameter (mm)× Shortest diameter (mm)×Shortest diameter (mm)/2

Relative tumor volume(RTV)=Tumor volume(day X)/Tumor volume(the first day)

On the basis of TV, the mice were randomly grouped (Day 1). Each group was consisted in six mice. Compound (1) was dissolved in DMSO and a solution was stored in the freezer before use. Compound (1) (180 µg/kg) was diluted in saline and intravenously injected on Day 1 and Day 8. Changes of RTV of each group was shown in FIG. 18. The antitumor activity was observed with tumor growth delay in the treated group.

AN3CA

A human endometrial cancer cell line AN3CA, which had been cultured in an E-MEM containing 10% FBS, and penicillin-streptomycin, was adjusted to a concentration of $1.4 \times 10^8$ cells/mL with Hanks' Balanced Salt Solution to prepare a cell suspension, and the suspension was mixed with Geltrex® (Thermo Fisher Scientific Inc., #A1413202) in a ratio of 1:1 to prepare a cell suspension in a concentration of $7 \times 10^7$ cells/mL. The cell suspension was inoculated in a volume of 100 µL into a subcutaneous part of a right flank of nude mice, 6 weeks of ages (CAnN.Cg-Foxn1nu/CrlCrlj, female, Charles River Laboratories Japan Inc.). Twelve days after cell inoculation (Day 1), the shortest diameter and the longest diameter of a tumor in each mouse were measured by using an electronic digital caliper (Digimatic™ caliper, Mitutoyo Corporation), so as to calculate the volume of the tumor in accordance with the following calculation formulae:

Tumor volume (mm³)=Longest diameter (mm)× Shortest diameter (mm)×Shortest diameter (mm)/2

Relative tumor volume (RTV)=Tumor volume (day X)/Tumor volume (the first day)

On the basis of the volumes of tumors obtained on Day 1, the mice were grouped such that averages of the tumor volumes were substantially equal among the groups. The experiment was conducted on groups each consisting of five mice. The test compound was dissolved in DMSO and a solution was stored in the freezer before use. Immediately before the administration, the stock solution was diluted with saline. The test compound in saline was intravenously once-weekly administered at 180 µg/kg for 2 weeks (on Day 1 and Day 8). The antitumor activity was observed with tumor regression in the treated group.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

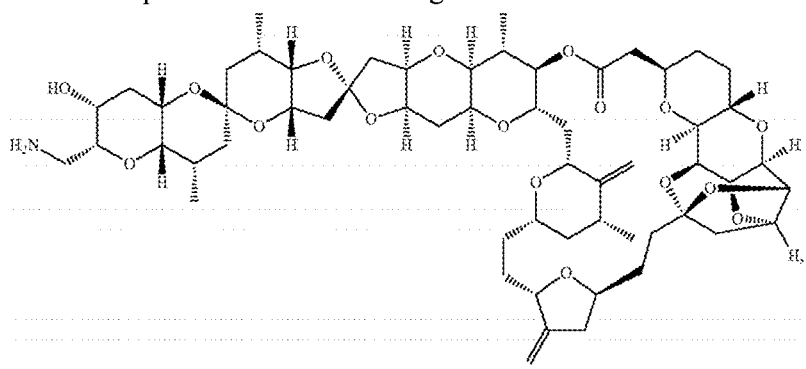

What is claimed is:

1. A compound of the following structure:

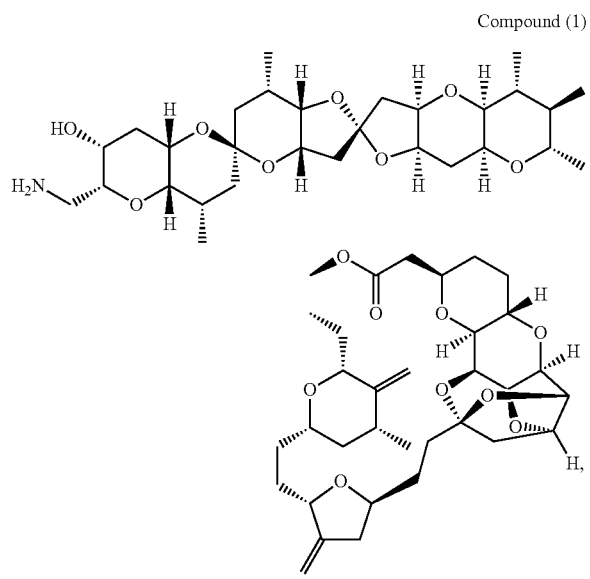

Compound (1)

or a pharmaceutically acceptable salt thereof.

2. The compound or pharmaceutically acceptable salt thereof according to claim 1 for use in inhibiting growth of tumor or cancer characterized by angiogenesis, invasion, or metastasis.

3. The compound or pharmaceutically acceptable salt thereof according to claim 1 for use in the treatment of tumor or cancer characterized by angiogenesis, invasion, or metastasis.

4. A pharmaceutical composition comprising the compound of claim 1, or pharmaceutically acceptable salt thereof, in a pharmaceutically acceptable carrier.

5. A method for treating a tumor or cancer characterized by angiogenesis, invasion or metastasis in a subject comprising administering to the subject the compound of claim 1, or a pharmaceutically acceptable salt thereof, optionally in a pharmaceutically acceptable carrier.

6. The method of claim 5, wherein the cancer or tumor is head and neck cancer, breast cancer, esophageal cancer, uterine cancer, ovarian cancer, colorectal cancer, endometrial cancer, or a sarcoma.

7. The method of claim 6, wherein the cancer or tumor is head and neck cancer.

8. The method of claim 7, wherein the cancer or tumor is squamous cell carcinoma of the head and neck (SCCHN).

9. The method of claim 6, wherein the cancer or tumor is breast cancer.

10. The method of claim 9, wherein the cancer or tumor is HER2-positive breast cancer.

11. The method of claim 9, wherein the cancer or tumor is HER2-negative breast cancer.

12. The method of claim 9, wherein the cancer or tumor is triple negative breast cancer.

13. The method of claim 6, wherein the cancer or tumor is colorectal cancer.

14. The method of claim 6, wherein the cancer or tumor is esophageal cancer.

15. The method of claim 14, wherein the cancer or tumor is esophageal adenocarcinoma.

16. The method of claim 6, wherein the cancer or tumor is uterine cancer.

17. The method of claim 6, wherein the cancer or tumor is ovarian cancer.

18. The method of claim 6, wherein the cancer or tumor is a sarcoma.

19. The method of claim 18, wherein the cancer or tumor is uterine sarcoma, fibrosarcoma, or angiosarcoma.

20. The method of claim 5 comprising further treating the subject with radiation therapy.

21. The method of claim 5 comprising further treating the subject with a Programmed Death 1 protein (PD-1) antibody.

22. The method of claim 5 comprising further treating the subject with an anti-EGFR (epidermal growth factor receptor) mAb.

23. The method of claim 22, wherein the cancer or tumor is head and neck cancer.

24. The method of claim 23, wherein the cancer or tumor is squamous cell carcinoma of the head and neck (SCCHN).

25. The method of claim 22, wherein the anti-EGFR (epidermal growth factor receptor) mAb is cetuximab.

26. The method of claim 5 comprising further treating the subject with an HER2 (human epidermal growth factor receptor) mAb.

27. The method of claim 26, wherein the cancer is breast cancer.

28. The method of according to claim 26, wherein the HER2 (human epidermal growth factor receptor) mAb is trastuzumab.

29. A method for treating HER2-negative breast cancer or squamous cell carcinoma of the head and neck (SCCHN) in a subject comprising administering to the subject the compound of claim 1, or a pharmaceutically acceptable salt thereof.

* * * * *

UNITED STATES PATENT AND TRADEMARK OFFICE
CERTIFICATE OF CORRECTION

PATENT NO.         : 9,938,288 B1
APPLICATION NO.    : 15/814105
DATED              : April 10, 2018
INVENTOR(S)        : Yoshito Kishi et al.

It is certified that error appears in the above-identified patent and that said Letters Patent is hereby corrected as shown below:

On the Title Page

Item (57) in the Abstract, the following divided structure:

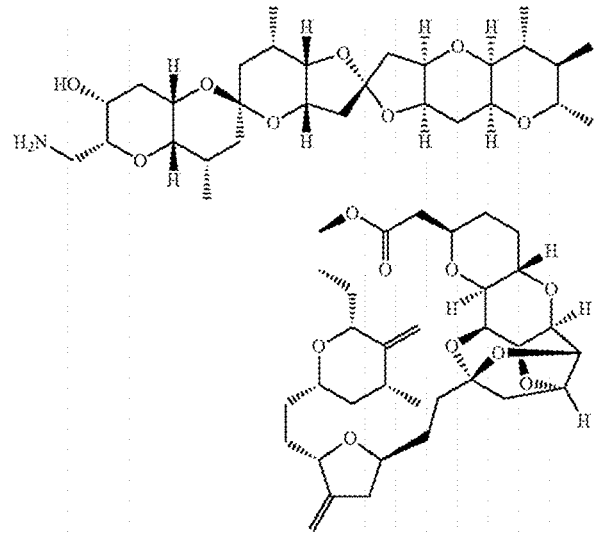

Should be replaced with the following structure:

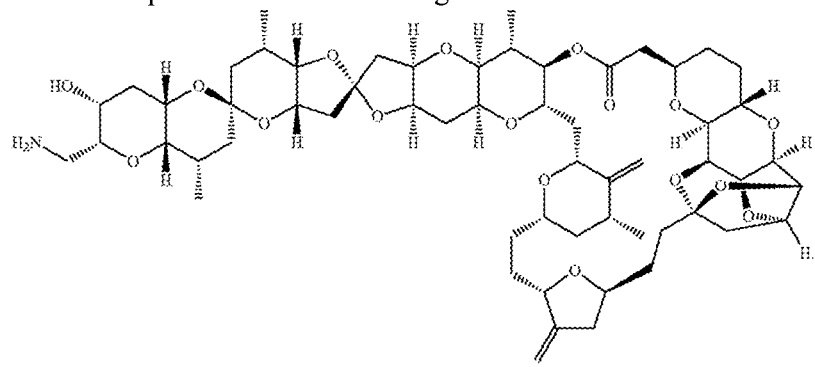

In the Claims

Signed and Sealed this
Twenty-second Day of May, 2018

Andrei Iancu
*Director of the United States Patent and Trademark Office*

CERTIFICATE OF CORRECTION (continued)

In Claim 1, at Column 65, Lines 5-25, the following divided structure:

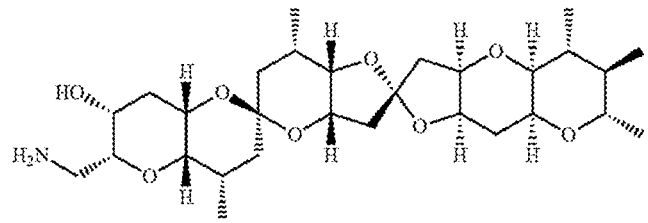

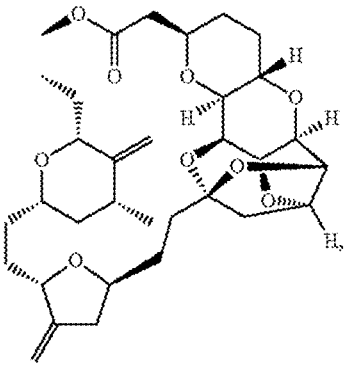

Should be replaced with the following structure: